United States Patent
Sherrah et al.

(10) Patent No.: US 11,432,619 B2
(45) Date of Patent: Sep. 6, 2022

(54) SYSTEM, METHOD, AND APPARATUS FOR MODELLING FEET AND SELECTING FOOTWEAR

(71) Applicant: DIGITAL ANIMAL INTERACTIVE INC., Vancouver (CA)

(72) Inventors: Jamie Roy Sherrah, Athelstone (AU); Michael Henson, Vancouver (CA); William Ryan Smith, Vancouver (CA)

(73) Assignee: DIGITAL ANIMAL INTERACTIVE INC., Vancouver (CA)

(*) Notice: Subject to any disclaimer, the term of this patent is extended or adjusted under 35 U.S.C. 154(b) by 574 days.

(21) Appl. No.: 16/486,605

(22) PCT Filed: Feb. 16, 2018

(86) PCT No.: PCT/CA2018/050180
§ 371 (c)(1),
(2) Date: Aug. 16, 2019

(87) PCT Pub. No.: WO2018/148841
PCT Pub. Date: Aug. 23, 2018

(65) Prior Publication Data
US 2020/0000180 A1    Jan. 2, 2020

(30) Foreign Application Priority Data

Feb. 18, 2017   (GB) ..................................... 1702681
Feb. 18, 2017   (GB) ..................................... 1702683
(Continued)

(51) Int. Cl.
*A43D 1/02*    (2006.01)
*G01B 11/00*   (2006.01)
(Continued)

(52) U.S. Cl.
CPC ................ *A43D 1/025* (2013.01); *A43B 3/34* (2022.01); *G01B 11/002* (2013.01); *G06T 7/60* (2013.01);
(Continued)

(58) Field of Classification Search
CPC .......... A43B 13/04; A43B 3/34; A43D 1/025; A43D 2200/60; A61B 5/107; A61B 5/1074; A61B 5/6807; G01B 11/002; H04N 7/18
(Continued)

(56) References Cited

U.S. PATENT DOCUMENTS 9,311,550 B2 * 4/2016 Sun ......................... G06T 7/248
9,460,557 B1 * 10/2016 Tran ...................... G06T 15/205
(Continued)

FOREIGN PATENT DOCUMENTS

WO    2016051416 A1    4/2016
WO    WO-2016051416 A1 *  4/2016 ............. A43D 1/025
WO    WO-2018007384 A1 *  1/2018 ............. A43D 1/025

OTHER PUBLICATIONS

The International Search Report received in the corresponding International Application No. PCT/CA2017/050180, dated May 22, 2018.

*Primary Examiner* — Kathleen M Walsh
(74) *Attorney, Agent, or Firm* — Kilpatrick Townsend & Stockton LLP

(57) ABSTRACT

One aspect of this disclosure is a method comprising: receiving, from a camera, a video feed depicting a pair of feet and a scaling object; capturing, with the camera, images of the feet and the scaling object based on the video feed; identifying foot features in each captured image; determining camera positions for each captured image by triangulating the foot features; generating a point cloud in a three-
(Continued)

dimensional space by positioning each foot feature in the three-dimensional space based on the camera positions; scaling the point cloud based on the scaling object; segmenting the point cloud into at least a right-foot cluster and a left-foot cluster; fitting a first three-dimensional morphable model to the right-foot cluster according to first foot parameters; and fitting a second three-dimensional morphable model to the left-foot cluster according to second foot parameters. Related systems, apparatus, and methods also are described.

15 Claims, 68 Drawing Sheets

(30) Foreign Application Priority Data

| Feb. 18, 2017 | (GB) | 1702684 |
|---|---|---|
| Feb. 18, 2017 | (GB) | 1702687 |
| Feb. 18, 2017 | (GB) | 1702689 |
| Feb. 18, 2017 | (GB) | 1702691 |
| Feb. 18, 2017 | (GB) | 1702692 |
| Feb. 18, 2017 | (GB) | 1702694 |
| Feb. 18, 2017 | (GB) | 1702696 |
| Feb. 18, 2017 | (GB) | 1702699 |

(51) Int. Cl.
| | |
|---|---|
| *G06T 7/60* | (2017.01) |
| *A43B 3/34* | (2022.01) |
| *H04N 7/18* | (2006.01) |
| *A61B 5/107* | (2006.01) |
| *A43B 13/04* | (2006.01) |
| *A61B 5/00* | (2006.01) |

(52) U.S. Cl.
CPC ............ *H04N 7/18* (2013.01); *A43B 13/04* (2013.01); *A43D 2200/60* (2013.01); *A61B 5/1074* (2013.01); *A61B 5/6807* (2013.01)

(58) Field of Classification Search
USPC .................................................. 33/6
See application file for complete search history.

(56) References Cited

U.S. PATENT DOCUMENTS

2014/0104395 A1\* 4/2014 Rohaly .............. G01B 11/165
348/47
2017/0270709 A1\* 9/2017 Tran .................. A43B 13/183

\* cited by examiner

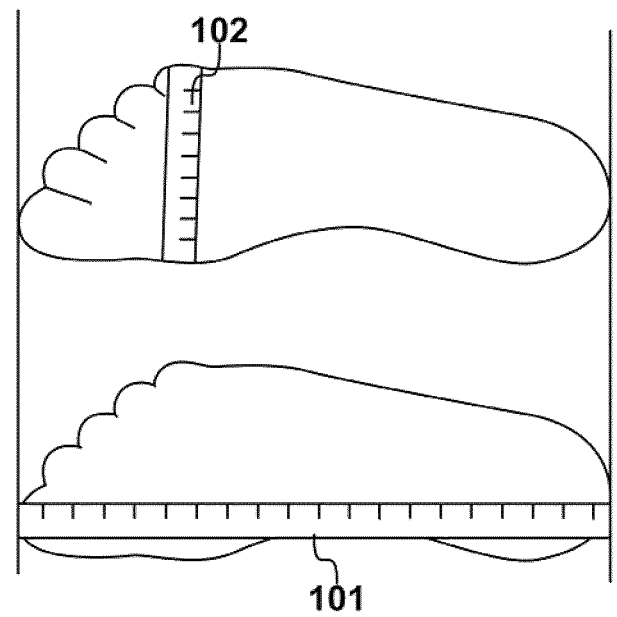
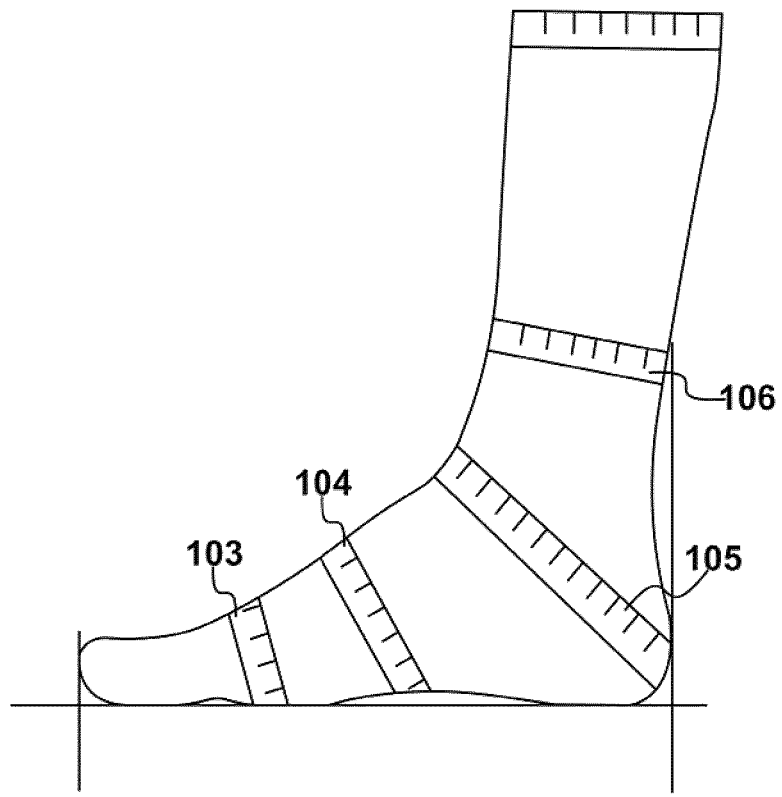
Fig. 1

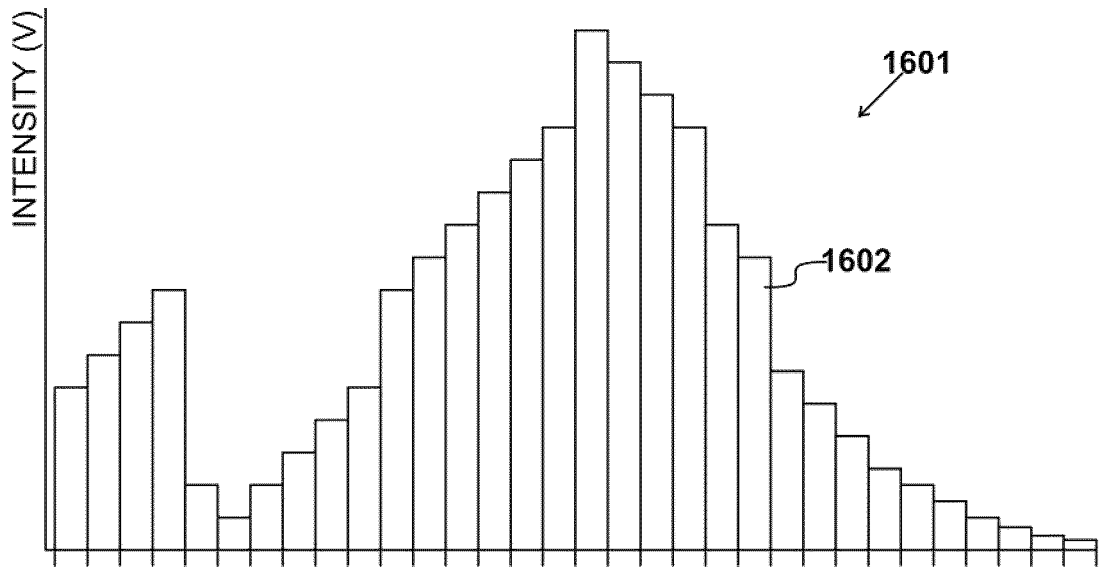
$$y(n) = \sum_{i=1}^{w} f(i).x(n + i - w/2)$$
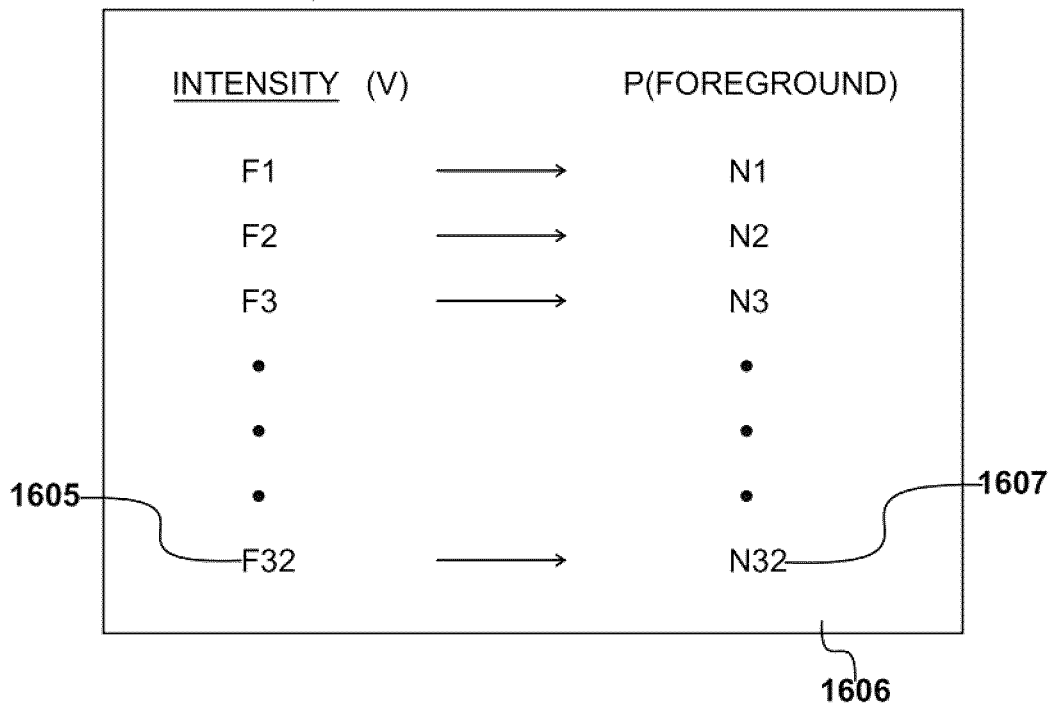
Fig. 16

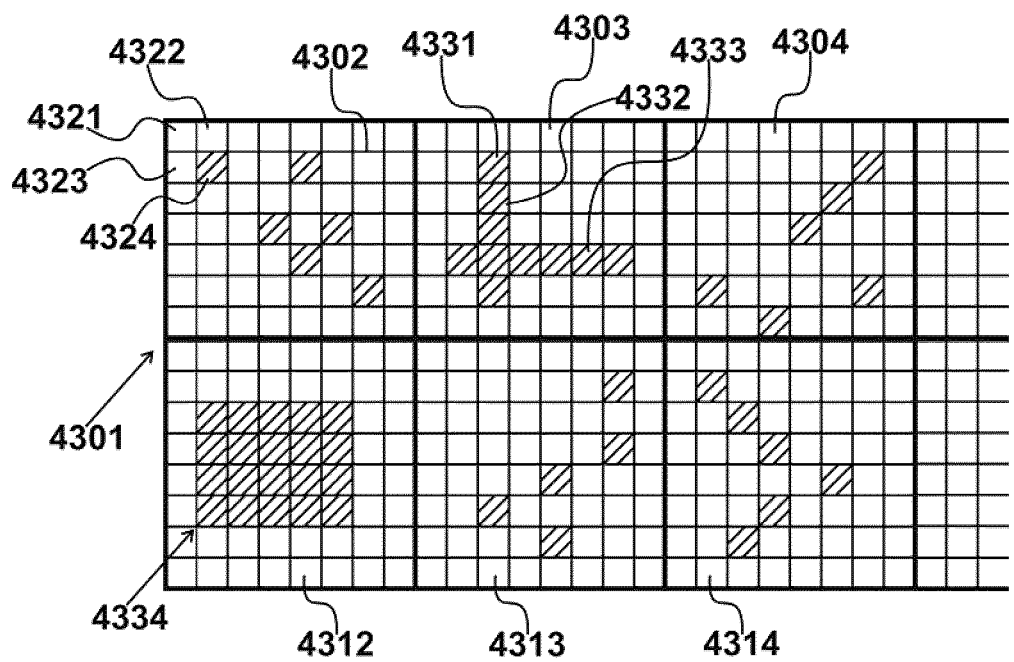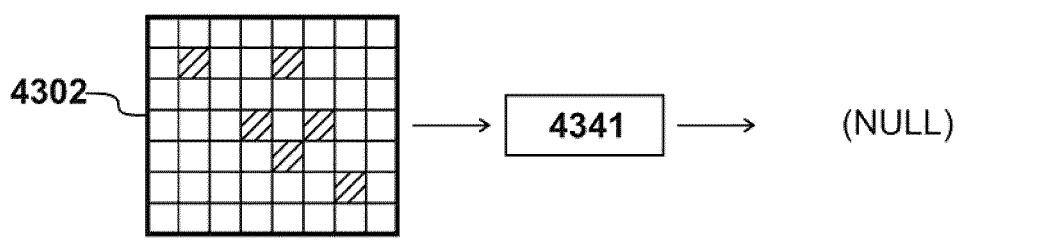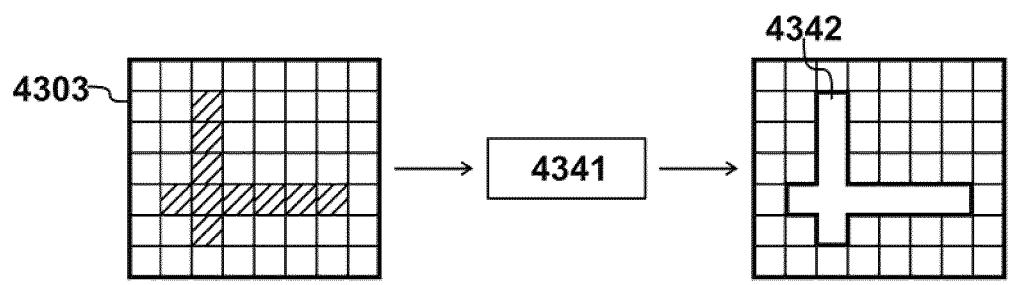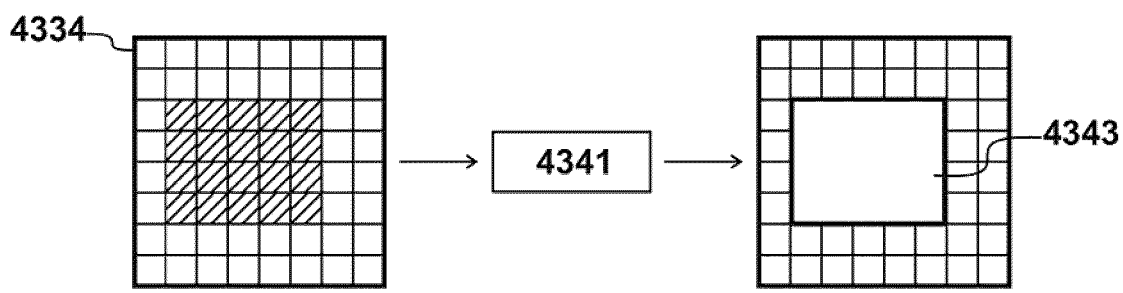
Fig. 43

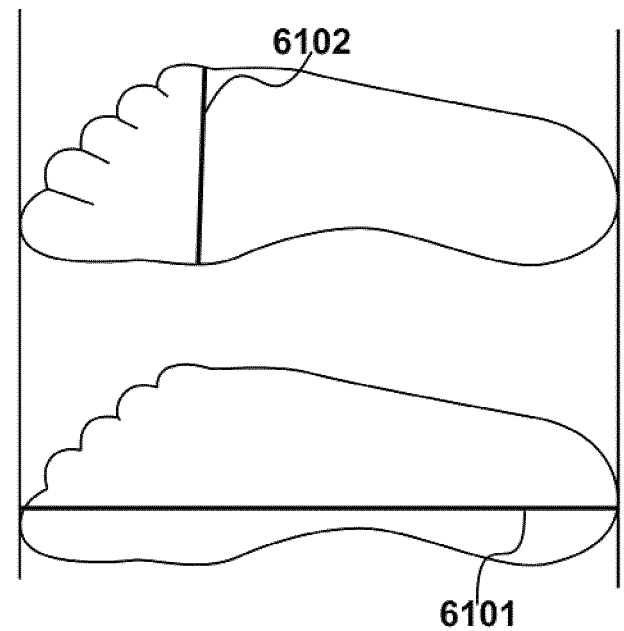
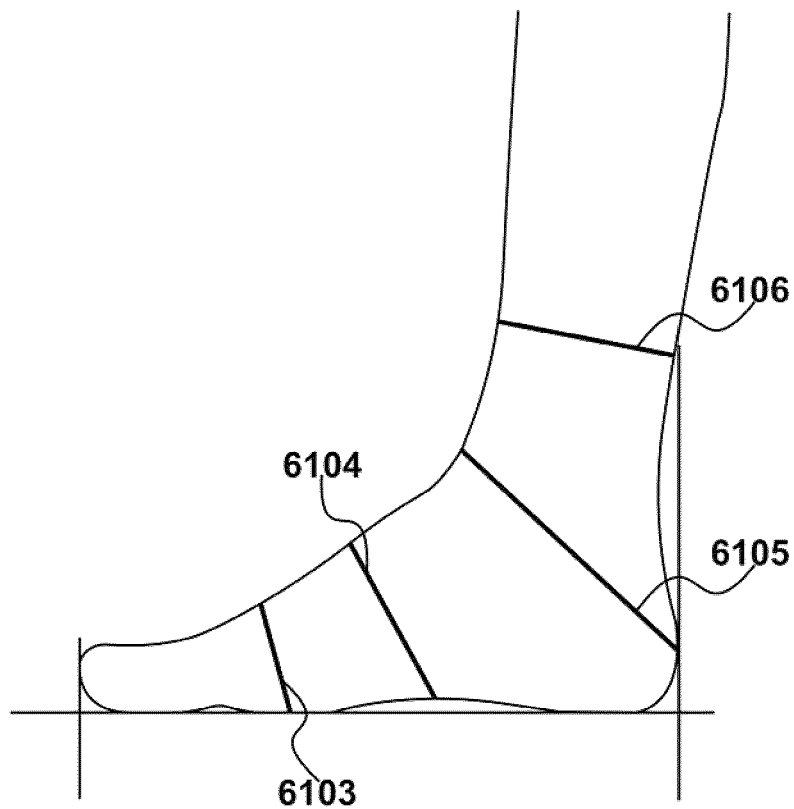
*Fig. 61*

SYSTEM, METHOD, AND APPARATUS FOR MODELLING FEET AND SELECTING FOOTWEAR

CROSS REFERENCE TO RELATED APPLICATION

This application is a U.S. National Phase of PCT/CA2018/050180, filed Feb. 16, 2018, which claims priority to Great Britain Patent Application 1702681.6, filed Feb. 18, 2017, Great Britain Patent Application 1702683.2, filed Feb. 18, 2017, Great Britain Patent Application 1702696.4, filed Feb. 18, 2017, Great Britain Patent Application 1702689.9, filed Feb. 18, 2017, Great Britain Patent Application 1702694.9, filed Feb. 18, 2017, Great Britain Patent Application 1702684.0, filed Feb. 18, 2017 and Great Britain Patent Application 1702687.3, filed Feb. 18, 2017, the contents of each of the above are herein incorporated by reference in the entirety.

TECHNICAL FIELD

Aspects of the present disclosure generally relate to systems, methods, and apparatus for modelling feet and selecting footwear.

BACKGROUND

In general, footwear is typically manufactured in standard sizes, such as those based on a general identification of foot length. The fit of each standard size may vary between manufacturers due to other factors, such as the shape and/or style of the footwear. Therefore, it is usually necessary for a recipient to visit an establishment where a significant number of shoes are available in inventory, and try on different pairs of footwear until an appropriate fit has been identified. This process may be time consuming for the recipient, especially if they have oddly shaped feet, which may or may not fit into any standard sizes in the inventory. This process also may be costly for the establishment, which may be required to maintain a large inventory, and provide staff to retrieve each different pair.

BRIEF SUMMARY OF THE INVENTION

Aspects of the present disclosure relate to systems, methods, and apparatus for modelling feet and selecting footwear. Numerous exemplary aspects are now described.

One aspect is a computer-implemented method. The method may comprise: receiving, from a camera, a video feed depicting a pair of feet and a scaling object; capturing, with the camera, images of the feet and the scaling object based on the video feed; identifying foot features in each captured image; determining camera positions for each captured image by triangulating the foot features; generating a point cloud in a three-dimensional space by positioning each foot feature in the three-dimensional space based on the camera positions; scaling the point cloud based on the scaling object; segmenting the point cloud into at least a right-foot cluster and a left-foot cluster; fitting a first three-dimensional morphable model to the right-foot cluster according to first foot parameters; and fitting a second three-dimensional morphable model to the left-foot cluster according to second foot parameters.

It may be understood that both the foregoing summary and the following descriptions are exemplary and explanatory only, neither being restrictive of the present disclosure.

Various aspects of the present disclosure will now be described by way of example only, with reference to the accompanying drawings.

BRIEF DESCRIPTION OF THE DRAWINGS

The accompanying drawings constitute part of the present disclosure. These drawings illustrate exemplary aspects of the disclosure that, together with the written descriptions, serve to explain the principles of this disclosure.

FIG. 1 shows an example of physical measurements of a foot;

FIG. 16 illustrates the populating and filtering of an exemplary histogram;

FIG. 43 shows an exemplary portion of a selected image considered during the exemplary procedure identified in FIG. 42;

FIG. 61 identifies exemplary foot parameters defined within the three-dimensional morphable model;

DETAILED DESCRIPTION

Figure 2:
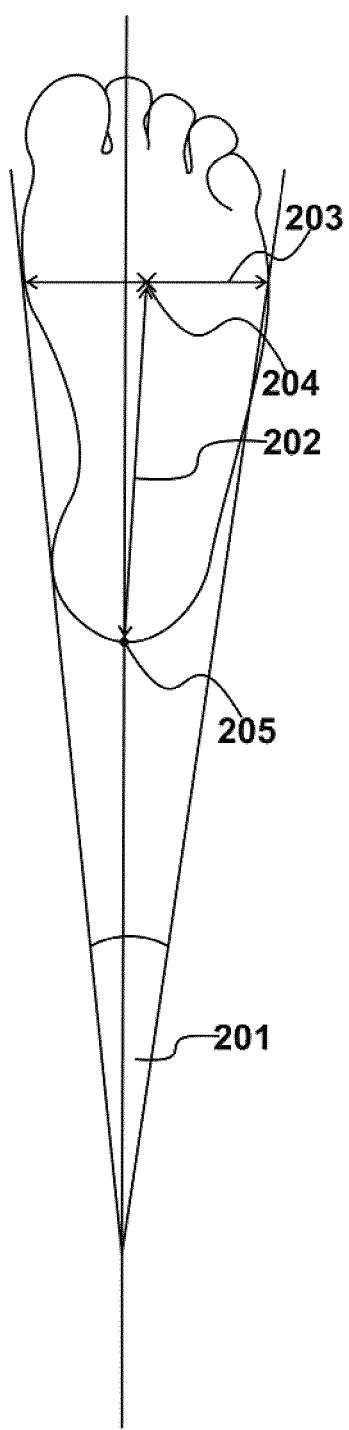
FIG. 2 shows further example measurements of a foot.

Aspects of the present disclosure are now described with reference to exemplary systems, methods, and apparatus for modelling feet and selecting footwear. Some aspects are described with particular reference to various means for capturing and processing images of a pair of feet and/or a scaling object from a camera during a sweeping motion. Unless claimed, these particular references are provided for convenience and not intended to limit the present disclosure. Accordingly, the concepts described herein may be applicable to any analogous selection systems, methods, or apparatus, footwear related or otherwise.

As used herein, the terms "comprises," "comprising," or any variation thereof, are intended to cover a non-exclusive inclusion, such that an aspect of a method or apparatus that comprises a list of elements does not include only those elements, but may include other elements not expressly listed or inherent to such aspect. In addition, the term "exemplary" is used in the sense of "example," rather than "ideal."

Aspects of this disclosure may be described in terms of algorithms and related computations, which may include operations on data stored within a computer memory. An algorithm is generally a self-consistent sequence of operations leading to a desired result. The operations typically require or involve physical manipulations of physical quantities, such as electrical or magnetic signals capable of being stored, transferred, combined, compared, and otherwise manipulated. For convenience, aspects of this disclosure may refer to these signals as bits, values, elements, symbols, characters, terms, numbers, or the like.

As used herein, terms such as "processing" or "computing" or "calculating" or "determining" or "displaying" or the like, may refer to the action and processes of a data processing system, or similar electronic device, that manipulates and transforms data represented as physical (electronic) quantities within the system's registers and memories into other data similarly represented as physical quantities within the system's memories or registers or other such information storage, transmission or display devices.

As used herein, the term "one or more processors," or simply "processors," may refer to any combination of processor(s) and/or processing elements, including resources disposed local to or remote from one another. For example, some processors may be local to a user and in communication with other processors, each processor having memory, allowing data to be obtained, processed, and stored in many different ways. A single processor may perform numerous or all aspects described herein. Numerous exemplary data processing configurations are described.

Some aspects of this disclosure are described with reference to an apparatus for performing one or more of the processes described herein. Terms such as "process" or "processes" may be used interchangeably with terms such as "method(s)" or "operation(s)" or "procedure(s)" or "program(s)" or "step(s)", any of which may describe activities performed by or with one or more processors. The apparatus may be specially constructed for these processes, or comprise a general purpose computer operable with one or more computer programs. Such programs may be stored in a machine (e.g. computer) readable storage medium, which may comprise any mechanism for storing or transmitting information in a form readable by a machine (e.g., a computer); such as: read only memory ("ROM"); random access memory ("RAM"); erasable programmable ROMs (EPROMs); electrically erasable programmable ROMs (EEPROMs); magnetic or optical cards or disks; flash memory devices; and/or electrical, optical, acoustical or other form of propagated signals (e.g., carrier waves, infrared signals, digital signals, etc.).

Aspects of exemplary processes are depicted in the illustrations and described in detail below, some of which depict or reference flowcharts with boxes interconnected by arrows. Aspects of flowcharts may be combined and/or interconnected to define footwear selection methods according to this disclosure. Some of these aspects may be interchangeable, allowing the footwear selections to be modified as technology evolves. Each may box include a title, and some of the titles may pose questions. In this disclosure, the titles and questions may be used to outline method steps, which may be computer-implemented. For example, each title or question may represent a discrete function, procedure, or process, aspects of which may be performed by one or more processors in response to any combination of manual input gestures and/or computer-implemented input gestures. The arrows may define an exemplary sequence of functions. Although not required, the order of the sequence may be important. For example, the order of some sequences may be used to realize specific processing benefits, such as improving the performance of a local processor or memory.

Particular aspects are described with reference to an image recordal apparatus including a camera. Any type of camera may be used. In one example, the camera may output image data at a spatial resolution of approximately eight million pixels per image, with a typical width to height aspect ratio of nine to sixteen. The image recordal apparatus may be a mobile computing device, such as an Apple® iPhone®. The mobile computing device may include any combination of cameras, communication devices, input devices, sensors, and/or notification devices. For example, the mobile device may include an internet connection (e.g., a cellular chip), a screen (e.g., a touchscreen), a movement sensor (e.g., an inertial movement sensor), an audio signal generator (e.g., a loudspeaker), and a haptic signal generator (e.g., a vibrator). Numerous exemplary configurations are described below.

Aspects of this disclosure are now described with reference to subheadings corresponding with the drawings described above. The subheadings are provided for convenience, such that each aspect may be described with reference to one or more of the drawings. Some aspects of this disclosure are described under multiple subheadings, each description and its equivalent being part of this disclosure.

FIG. 1

Exemplary foot measurements for a "last" are depicted in FIG. 1. In the art, a "last" is a mechanical form having a shape similar to that of a human foot. It may be used when making bespoke and non-bespoke (or mass produced) footwear. For example, when making bespoke footwear, a custom last may be manufactured based on a plurality of foot measurements and a specification of footwear type. The foot measurements may include various measurements of foot length, foot width, instep height, arch height and multiple circumferential measurements. As shown in FIG. 1, the foot measurements may comprise: a length measurement 101, a width measurement 102, a first circumferential measurement 103, a second circumferential measurement 104, a third circumferential measurement 105 and a fourth circumferential measurement 106.

FIG. 2

The foot measurements also may include a splay angle 201 and a mid-foot length 202, as shown in FIG. 2. Each foot being measured may have recognisable components or "foot features," including a first metatarsal head, a fifth metatarsal head, and the like. Various geometrical and/or mathematical operations may be performed to obtain the foot measurements and/or identify the foot features. As shown in FIG. 2, for example, to determine the mid-foot length, a width may be considered on a line 203 connecting the first metatarsal head with the fifth metatarsal head; and a centre point 204 of this line may be identified, such that the mid-foot length 202 represents the length from a farthest point 205 of the heel to the centre point 204.

Bespoke footwear may be more expensive. Therefore, it is not common practice for footwear to be made individually for each user. Typical practice is for footwear to be mass-produced using standard notational sizes, and for allocations to be made from a general identification of length 101 (usually the measure identified as representing a shoe size) followed by a degree of trial and error. Because of this practice, it is usually necessary for a recipient to visit an establishment where a significant number of shoes are available, so that several pairs of shoes may be tried until an appropriate fit has been identified. Furthermore, in addition to physical fit, the recipient may express a fitting preference, require a specific degree of functionality, or make other requests driven primarily by fashion.

Mass-produced footwear may be manufactured using generic lasts that are approximately foot shaped, and have standard notational sizes (i.e., foot lengths). Even with standard sizes, the shape of each generic last may vary significantly based on footwear style, toe shape and sizing, and the manufacturing process. Therefore, although it is possible to mass-produce footwear with standard sizes, using this single measurement may create difficulties in practice because the standard size may or may not correspond directly with fit. As a result, a recipient may be required to try on many pairs of shoes of many standard sizes to find a pair that fit.

FIG. 3

Figure 3:
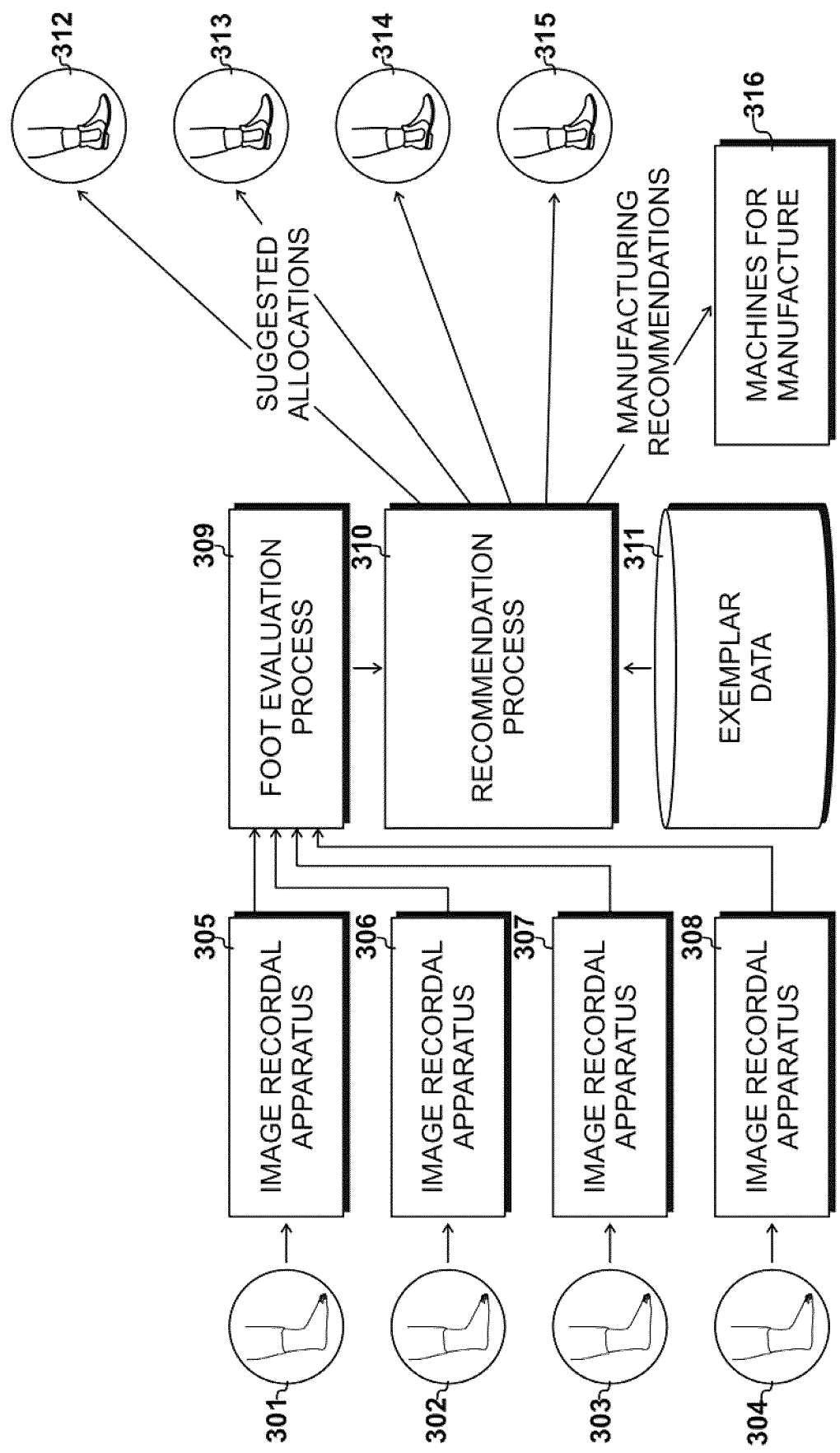
FIG. 3 shows exemplary procedures for making footwear allocations based on images of feet taken by an exemplary image recordal apparatus.

Aspects of an exemplary process for facilitating the remote allocation of footwear based on images of a recipient's exposed feet are identified in FIG. 3. As shown, each recipient may be represented by a respective foot 301, 302, 303 and 304; and may have or be provided with a respective image recordal apparatus 305, 306, 307, 308.

Each apparatus 305 to 308 may record image data from which accurate evaluations may be made, and the image data may include pictures or two-dimensional images of each foot 301, 302, 303, and 304. For example, each apparatus 305 to 308 may be an iPhone® or equivalent mobile device. As used herein, the term "image data" may include any combination of images or video; and the term "evaluations" may relate to the determination of foot related attributes of each recipient based on the image data, without taking physical measurements of the type identified in FIG. 1. In some aspects, these evaluations may be based upon the exemplary foot measurements identified in FIG. 1. Alternatively, in other aspects, the evaluations may be based on quantities or qualities that do not map onto physical measurements directly, but do facilitate the process of footwear allocation.

As shown in FIG. 3, image data may be recorded by the image recordal apparatus 305 to 308, and uploaded to a foot evaluation process 309. The foot evaluation process 309 may be operated by one or more processors that determine foot-related attributes based on image data received from the image recordal apparatus 305 to 308. The one or more processors may be local and/or remote to apparatus 305 to 308. For example, the image data may be uploaded to a remote processing device (e.g., device 3801 of FIG. 38) with sufficient processing capability to invoke the procedures detailed herein (e.g., process 309) sufficiently quickly. However, it is appreciated that in future, greater levels of processing power may be available locally to apparatus 305 to 308, allowing a larger proportion, and possibly all, of the processing to be performed by a local processor (e.g., processor 401 of FIG. 4).

After performing the foot evaluation process 309, evaluation data may be output by the one or more processors to a recommendation process 310 that calls upon exemplar data from a database 311. In this configuration, the one or processors may operate recommendation process 310 to make comparisons with the exemplar data from database 311, thereby allowing the recommendation process 310 to make suggested allocations of footwear, identified at 312, 313, 314 and 315 for respective recipients 301 to 304. In some aspects, the exemplar data may be derived from evaluations of exemplar-recipients or "fit leaders" who have tried on many footwear examples. For example, the fit leaders may be required to try on new examples of footwear as they become available, thereby enabling the database 311 of exemplar data to be kept up-to-date.

In some aspects, recommendation process 310 also may include a second database of exemplar data from previously allocated recipients. For example, after a recipient has had their image data evaluated, it is possible for their data to be read from the second database without being required to supply new image data. Furthermore, as more recommendations are made in response to receiving more data, the recipient database may continue to grow. Consequently, recommendation process 310 may provide manufacturing recommendations to manufacturers, thereby allowing suggested improvements to be made to machines for manufacture, as illustrated at 316.

According to this disclosure, each allocation of footwear may be used to enhance the exemplar data contained in database 311 by receiving feedback from the recipient. In this way, it is possible to achieve online data improvement. For example, a recommendation may be made to a recipient at the conclusion of recommendation process 310. In some aspects, the recipient agrees to the recommendation, a physical allocation of the recommended footwear is made, and the recipient provides a score (e.g., of say from 1 to 10) identifying how satisfied they are with the fit of the recommended footwear. According to this example, the recipient may now be identified as a pseudo-fit-leader; and further recommendations may be made based on the pseudo-fit-leader's data, possibly with a weighting applied to reduce their influence compared to an actual fit leader. However, if a match is made to several pseudo-fit leaders in preference to an established fit leader, their combined weighted values may add up to a total that is greater than the weight given to the actual fit leader.

FIG. 4

Figure 4:
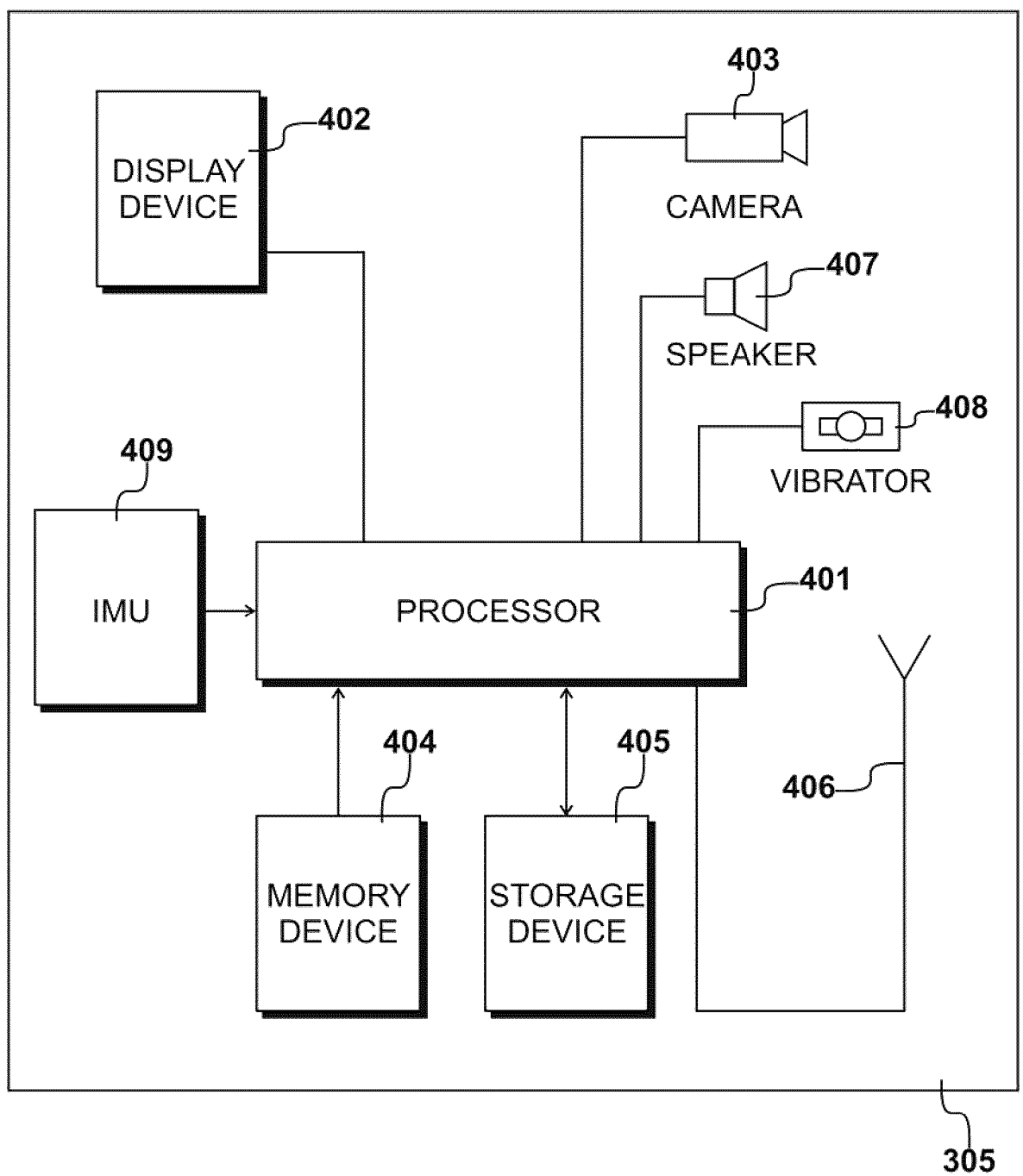
FIG. 4 shows a schematic representation of an exemplary image recordal apparatus of the type shown in FIG. 3.

A schematic representation of an exemplary image recordal apparatus 305 is illustrated in FIG. 4. Additional aspects of this disclosure are now described with reference to apparatus 305, which may be identical to apparatus 306 to 308. As noted above, apparatus 305 may be a smartphone (e.g., an iPhone®), a tablet (e.g., an iPad®), a laptop (e.g., a MacBook®), or other mobile and/or personal computing device having similar capabilities. As shown in FIG. 4, for example, image recordal apparatus 305 may include: a processor 401, a visual display device 402, a camera 403, a memory device 404, a storage device 405, and a transceiver 406.

Processor 401 may supply output data to visual display device 402, which may include a touchscreen. Camera 403 may output image data to processor 401. As noted above, the term "image data" may include any combination of images, video, and related data, such as position data. For example, camera 403 may output image data including images at a spatial resolution of eight million pixels per image, with a typical width to height aspect ratio of nine to sixteen. Each image may be captured based on one or more frames in a video. Because these parameters may vary amongst camera types on a case-by-case basis, the type of camera 403 may be a design choice, such that any type of camera 403 may be used.

To perform image processing procedures, processor 401 may receive executable instructions from memory device 404, which may include any machine-readable storage medium. For example, the executable instructions may be part of one or more programs that are stored on memory device 404, and configured to perform any of the processes described herein. The image data and processed image data may be written to and read from a storage device 405, which also may include any machine-readable storage medium.

Transceiver 406 may include any wired or wireless technology suitable for transmitting the image data to or with the one or more processors described herein. For example, transceiver 406 may include a wireless antenna configured to upload and/or download the image data to and/or from the one or more processors via a connection to a cellular network.

Processor 401 may analyse the image data output from the camera 403 based on the executable instructions received from memory device 404, and perform various local functions in response thereto. One local function may be a notification function. For example, image recordal apparatus 305 also may include a speaker 407 and a vibrator 408. Speaker 407 allows audio output to be generated, thereby allowing warning notifications to be given during an image recordal process. For example, some notifications may take the form of recorded voice commands that are output during the image data recordal process to assist the recipient and/or other use of apparatus 305.

The notification function may vary. For example, a beeping sound (or first sound) may be generated at a lower volume when the image data has been recorded correctly according to an image recordal process, and a less pleasant buzzing sound (or second sound) may be generated at a higher volume when image data has not been recorded correctly according said process, such as when one or more recordal positions have been missed. As a further example, when an image data recordal position has been missed, the vibrator 408 may be energised to notify the recipient that missed positions will need to be revisited.

Image recordal apparatus 305 also may comprise an inertial measurement unit (or "IMU") 409. As shown in FIG. 4, IMU 409 may be operable with processor 401 to quantify movements of apparatus 305 in a three-dimensional space. For example, IMU 409 may be an electronic device configured to measure and output a specific force of apparatus 305 and/or its angular rate using a combination of accelerometers, gyroscopes, and the like. IMU 409 may be optional. When present, IMU 409 may allow processor 401 to determine whether a sufficient amount of image data has been captured. For example, IMU 409 may output position data that facilitates one or more operations performed by evaluation process 309. Numerous exemplary functions of IMU 409 are described below.

FIG. 5

Figure 5:
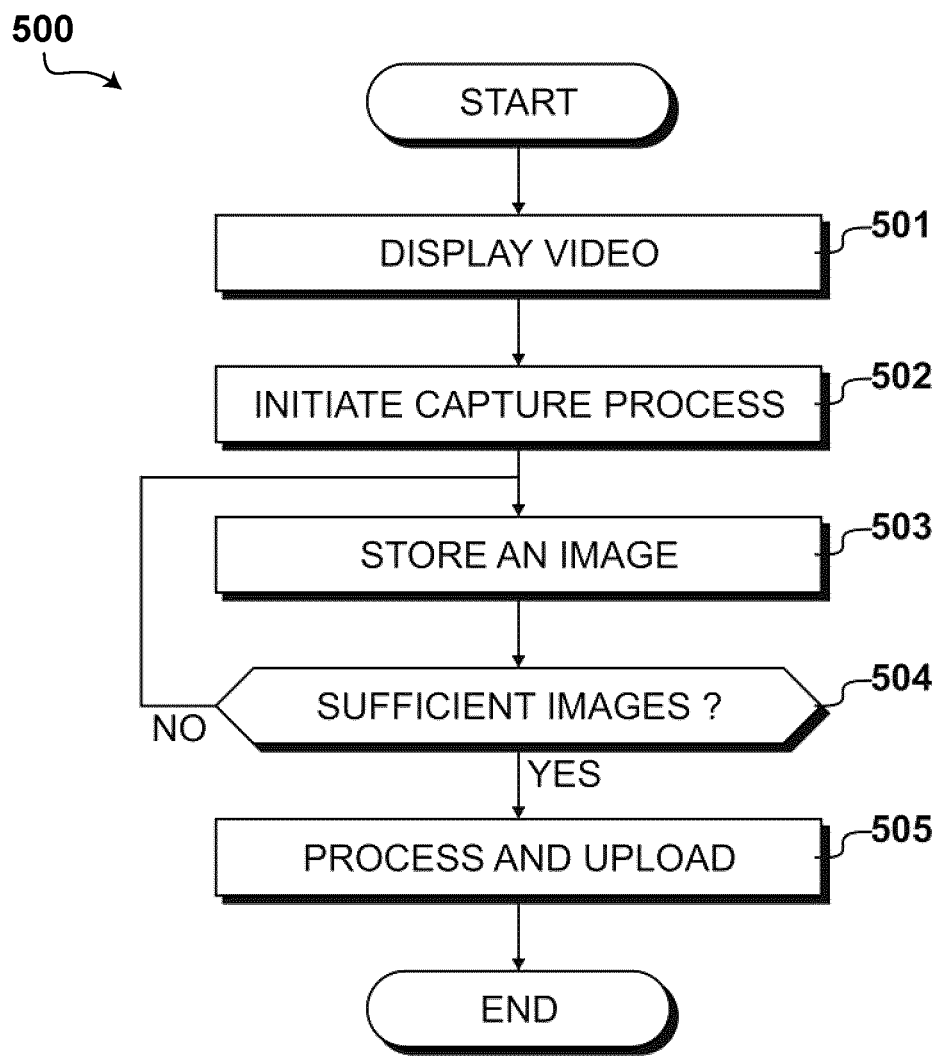
FIG. 5 shows exemplary procedures for capturing images using the exemplary image recordal apparatus identified in FIG. 4.

Aspects of an exemplary image process 500 are depicted in FIG. 5 as a set of exemplary procedures executed by one or more processors. In some aspects, process 500 may be implemented by processor 401 in response to receiving instructions from memory device 404.

At step 501, the one or more processors may output image data from camera 403, and display the image data on display device 402. In this example, the image data may include a video feed 601 (e.g., FIG. 6) comprising of a plurality of static images. The one or more processors may capture images of feet (each a "captured image") with camera 403 based on the static images from video feed 601. For example, each captured image may be obtained with the one or more processors by reading the static images from feed 601 during a movement of apparatus 305; and responsively putting camera 403 into different mode, adjusting parameters of camera 403 (e.g., setting the focus), and recording images of feet at different positions of the movement. As described below, step 501 may comprise steps for directing the recipient to perform the movement by positioning apparatus 305 at appropriate locations for obtaining the captured images.

At step 502, the one or more processors may initiate a capture process, during which procedures are conducted to ensure that the foreground foot-related pixels (or "foot pixels") may be distinguished from the background non-foot-related pixels (or "non-foot pixels"). Step 502 may allow the captured images to be optimized, and/or include various quality control procedures. For example, at step 502, the one or more processors may perform a tracking operation to ensure that the image data includes images of feet, and maintain the feet within the images. In this example, processor 401 may generate a notification if the feet are no longer in capture area, the images are of low quality, and/or the images are of an insufficient quantity.

At step 503, after initiating the capture process at step 502, the one or more processors may obtain the captured images based on video feed 601, and store the captured images as image data by repeated operation of step 503. For example, the one or more processors may store image data at step 503; determine whether a sufficient amount of image data has been captured at step 504; and, if answered in the negative, repeat step 503 so that further image data may be captured and/or stored.

Eventually, by repeating steps 503 and 504 as needed, sufficient image data will have been stored, allowing the one or more processors to answer the question asked at step 504 in the affirmative. Therefore, at step 505, having stored sufficient image data in step 503, the one or more processors may process the image data, and/or upload the image data to foot evaluation process 309.

Figure 6:
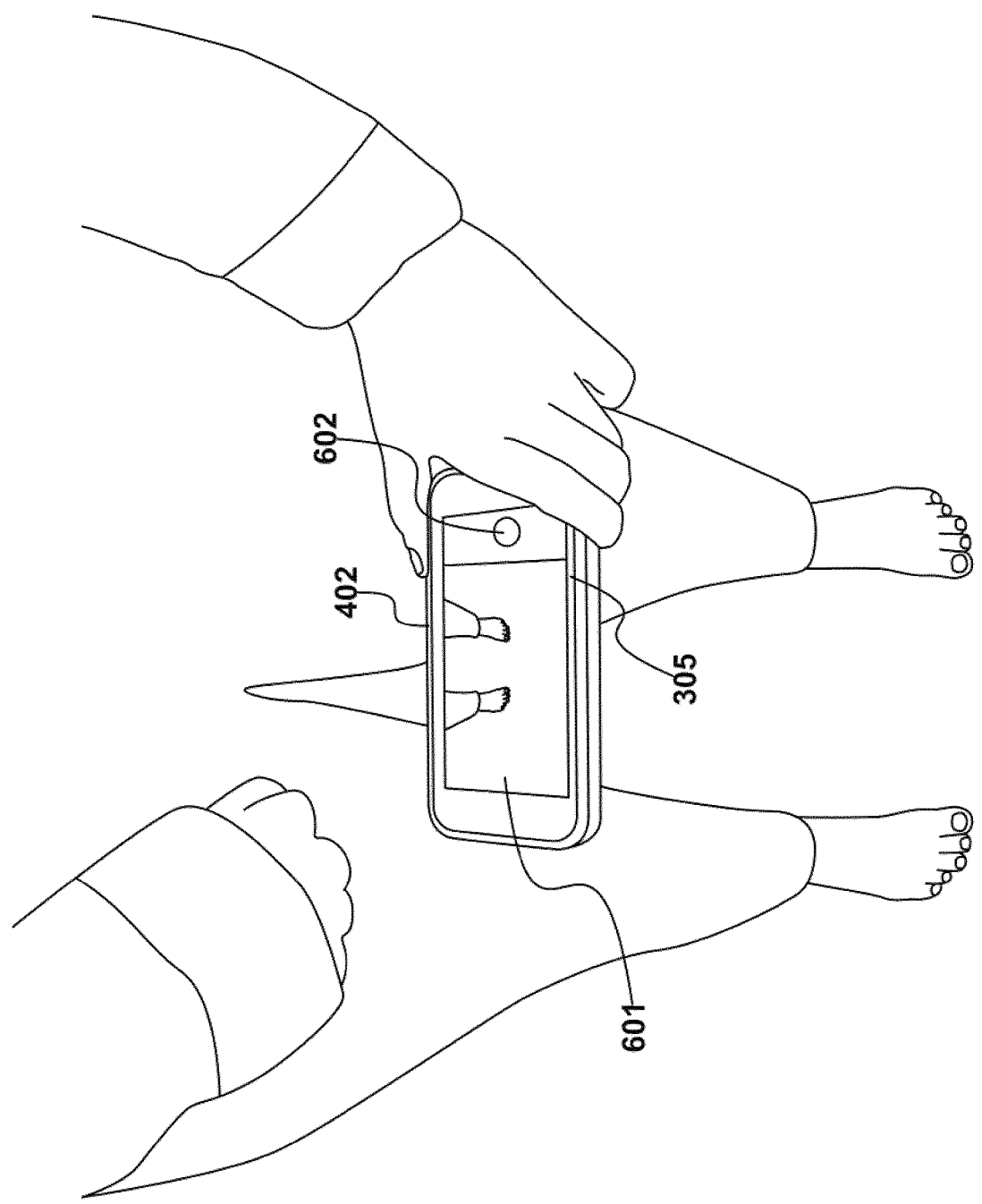
FIG. 6 shows an exemplary display of a video feed.
Figure 6A:
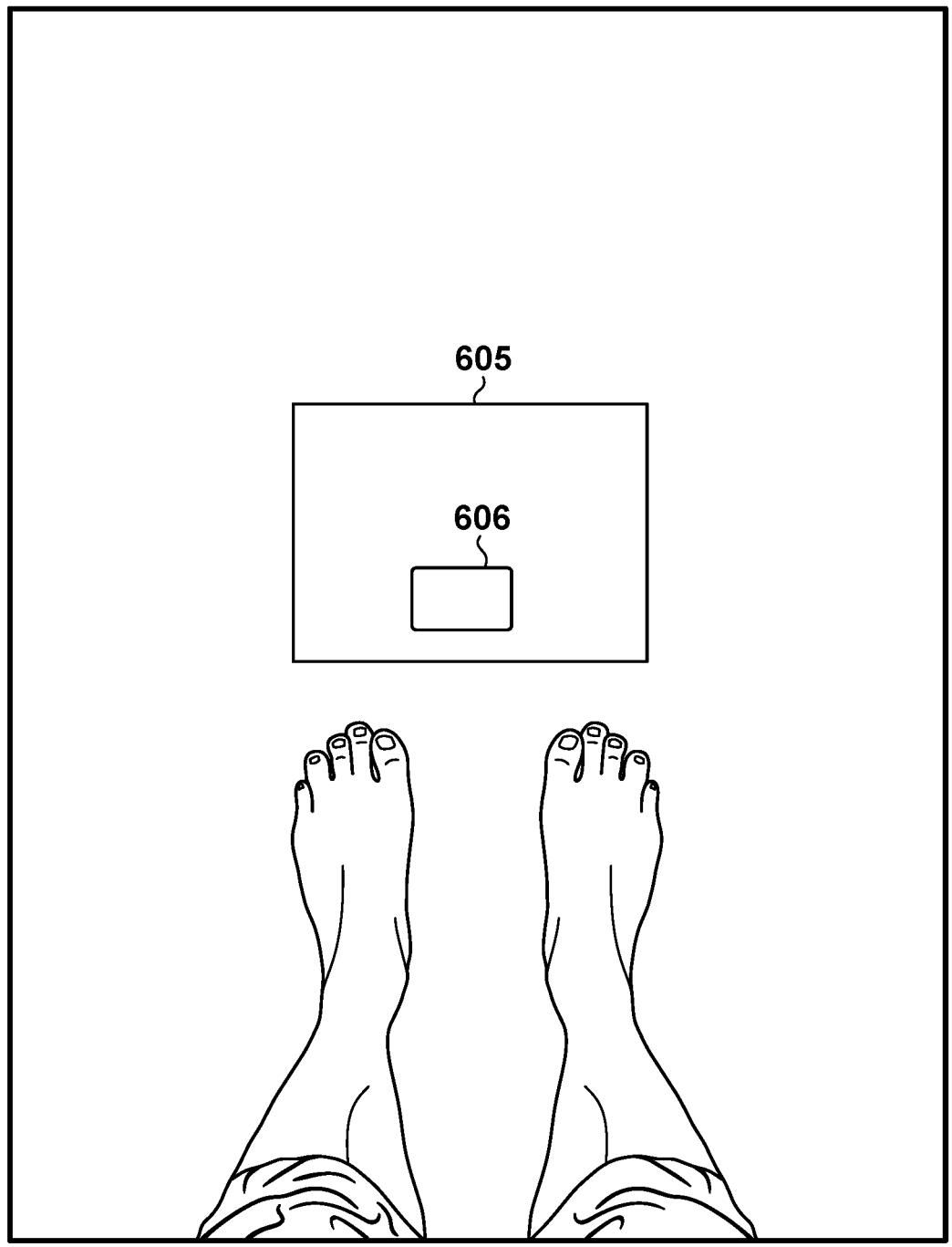
FIG. 6A shows another exemplary display of a video feed.

FIGS. 6 and 6A

As noted above, image recordal apparatus 305 may be implemented as a mobile or personal computing device, such as a smart cellular telephonic device (e.g., an iPhone®), provided the device has sufficient processing capability. Additional steps may be performed with apparatus 305 to facilitate the processing of image data therewith.

As illustrated in FIG. 6, video feed 601 may be displayed on display device 402 of image recordal apparatus 305 by the one or more processors (e.g., by processor 401). All or a portion of display device 402 may be responsive to manual interactions with the recipient (e.g., such as manual-input gesture), and may operate as a touchscreen. For example, the recipient may position apparatus 305 in front of them and align camera 403 so that their feet are view of video feed 601, allowing for initiation of a process for obtaining the captured images based on feed 601. After initiation, either the processors or the recipient may select positions for capturing image data by operation of display device 402 and/or an input button 602 thereof, shown in FIG. 6 as an exemplary region of or adjacent to the display device 402.

As shown in FIG. 6A, the recipient may be encouraged to stand in front of a substantially white sheet of paper 605 with a scaling object 606 located at a mid-position along the near long edge of the paper. In later processing, the paper 605 may assist with the detection of scaling object 606. Sheet of paper 605 may be optional and not actually necessary, provided that scaling object 606 is distinguishable from the floor. As described herein, scaling object 606 may comprise any object that allows distances to be evaluated within a three-dimensional environment, including objects having a known size, such as a credit card.

FIG. 7

Figure 7:
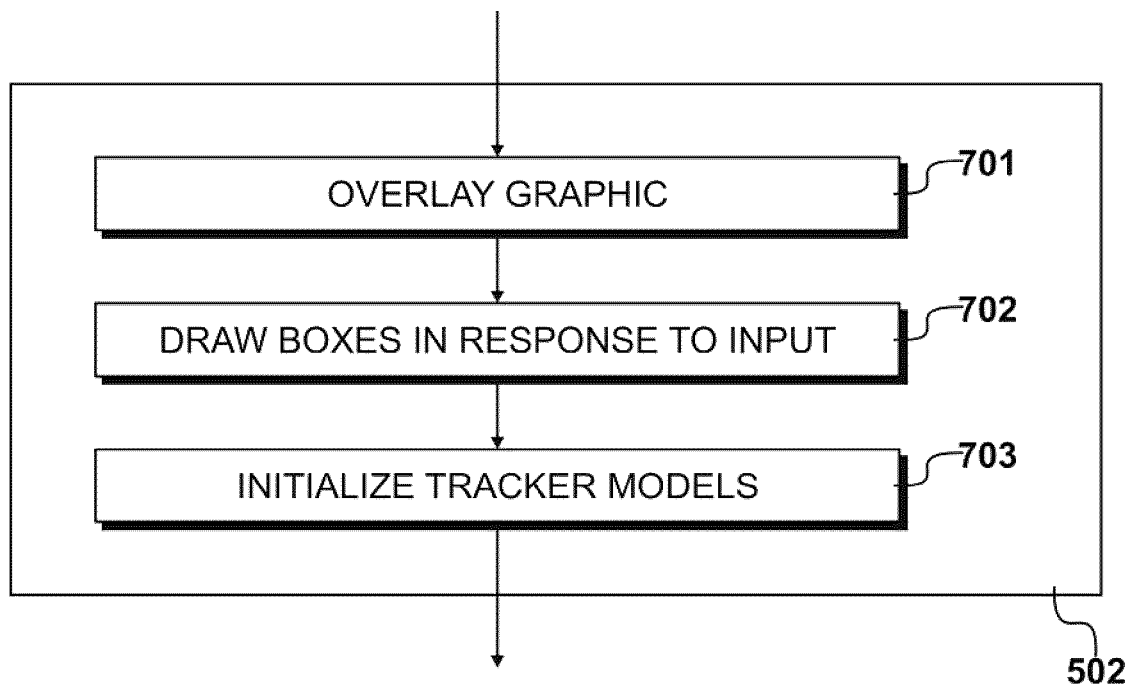
FIG. 7 illustrates exemplary procedures for initiating a capture process.

Exemplary procedures 502 for initiating image capture process 500 (FIG. 5) are shown in FIG. 7. In some aspects, image capture process 500 may be implemented by executable instructions that are running on one or more processors, multi-threaded, and use call back functions activated by an event-based window manager.

Figure 8:
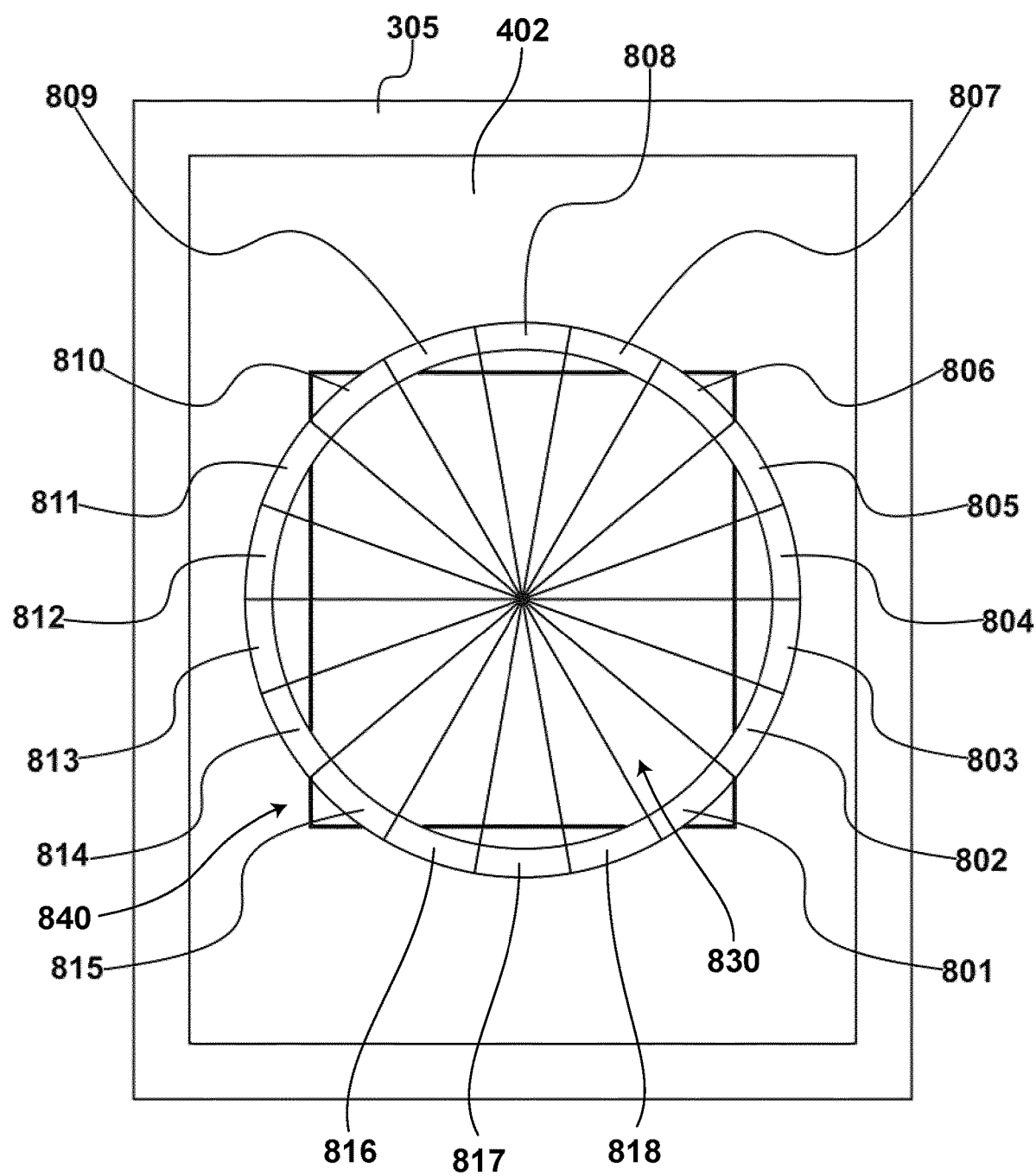
FIG. 8 shows an example of an overlaid graphic.
Figure 8A:
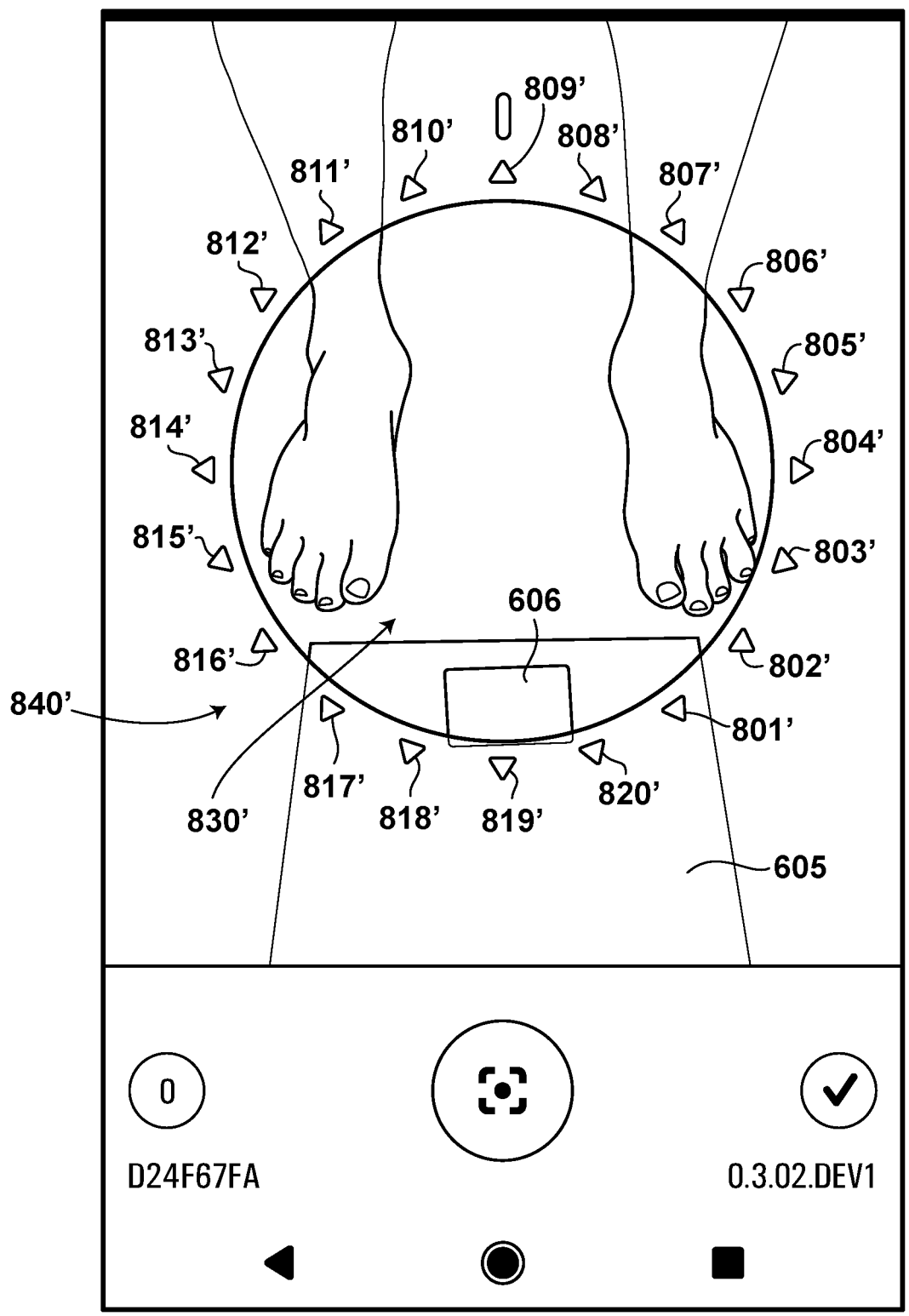
FIG. 8A shows another example of an overlaid graphic.

As shown in FIG. 7, for example, video feed 601 may be continuously displayed on display device 402, as identified at step 501 of FIG. 5. At step 701, the one or more processors may overlay a graphical image onto video feed 601. Exemplary graphical images are depicted in FIGS. 8 and 8A as having a central capture area 830 surrounded by a rotational guide 840. To obtain satisfactory image data, the recipient may move image recordal apparatus 305 so that their feet are shown in central capture area 830. As shown in FIG. 8, for example, rotational guide 840 may include markers 801 to 818 arranged a plurality of azimuth angles to identify a corresponding plurality of rotational positions for apparatus 305, similar to the identification of hours on a clock face.

Aspects of markers 801 to 818, such as colour, may be varied by the one or more processors to indicate that an image has been captured at one of the azimuth angles (e.g., by turning the corresponding marker green); or that another image is still required at said angle (e.g., by turning the corresponding marker red). These aspects of markers 801 to 818 may be updated during this process. For example, processor 401 may be operable with IMU 409 to update aspects of markers 801 to 818 (or other aspects of the graphical image) based on position data output from IMU 409 as the image recordal apparatus 305 is moved about and/or around the feet.

The processes associated with displaying video feed 601 and updating the graphical image may happen continually throughout the processes associated with capturing and storing image data. However, it should be appreciated that, in some aspects, video feed 601 may be at a lower definition and/or lower quality than the captured images included in the image data and uploaded to foot evaluation process 309.

During the initiation process 502, image data may not be captured because tracking operations may be required to optimize settings such as focus, exposure, and/or white balance. Consequently, in some aspects, no images may be captured at step 502 because all of the capturing and storing operations are performed at step 503.

Exemplary tracking operations are now described. Aspects of these operations may be performed by the one or more processors. For example, at step 503, the processors may perform the tracking operations in real-time by locating the feet in a metering area of video feed 601, and optimizing the pixels within the metering area, resulting in a high quality image of the pixels within the metering area. As described further below, the processors also may define the metering area, and locate the feet therein. Once the feet have been located, the processors may automatically adjust at least one of a focus, an exposure, or a white balance of the pixels located in the metering area.

Some aspects of the tracking operations may be performed by the recipient using the one or more processors. At step 702, for example, the recipient may be prompted by the processors to draw a tracker box around each of the feet displayed in video feed 601, allowing the one or more processors to identify the feet based on the location of the tracker box. For example, the prompt may be displayed on display device 402, and/or include instructions for drawing the tracker box using an input device, such as the recipient's finger, a stylus, or other pointing device operable with display device 402.

Accordingly, aspects of the tracking operations may be implemented entirely by the one or more processors; and/or be operable with said processors in response to a manual input from the recipient. Either way, the initiation process 502 identified in FIG. 5 may be implemented by the one or more processors in order to receive information for identifying characteristics of the foreground pixels, allowing the foot pixels to be distinguished from the non-foot pixels.

At step 703, the one or more processors may initialize a tracker model such that, following the tracking operations, said processors may distinguish between foot pixels and non-foot pixels. In some aspects, the tracker model may be based on a colour model. At step 703, for example, the one or more processors may perform a colour space manipulation in order to distinguish between foot pixels and non-foot pixels. As described further below, the colour space manipulation may be based upon full colour image data.

FIGS. 8 and 8A

Examples of an overlaid visual graphic of the type identified in FIG. 7 are illustrated in FIGS. 8 and 8A. As shown in FIG. 8, the overlaid graphic may be similar to a compass rose, in which the central capture area 830 is surrounded by the rotational guide 840. A circumference of rotational guide 840 may include a plurality of markers 801 to 818. Each marker 801 to 818 may be presented to the recipient in one or more colours. For example, when the image data storage process 503 starts, each marker 801 to 818 may be presented in first colour (e.g., red), indicating that captured images have not yet been associated with markers 801 to 818.

Upon initiating process 503, the one or more processors may establish a start position based on an initial position of image recordal apparatus 305. For example, the recipient may select one of the markers 801 to 818 as the start position. IMU 409 may be used to identify one of markers 801 to 818 as the start position so that any relative movements of apparatus 305 with respect to this start position may be identified in response to output data received from the IMU 409. Either way, as the image recordal apparatus 305 is rotated by the recipient, the overlaid graphical image shown in FIG. 8 may retain its orientation relative to apparatus 305, thereby appearing to rotate relative to apparatus 305, like a compass.

Figure 23:
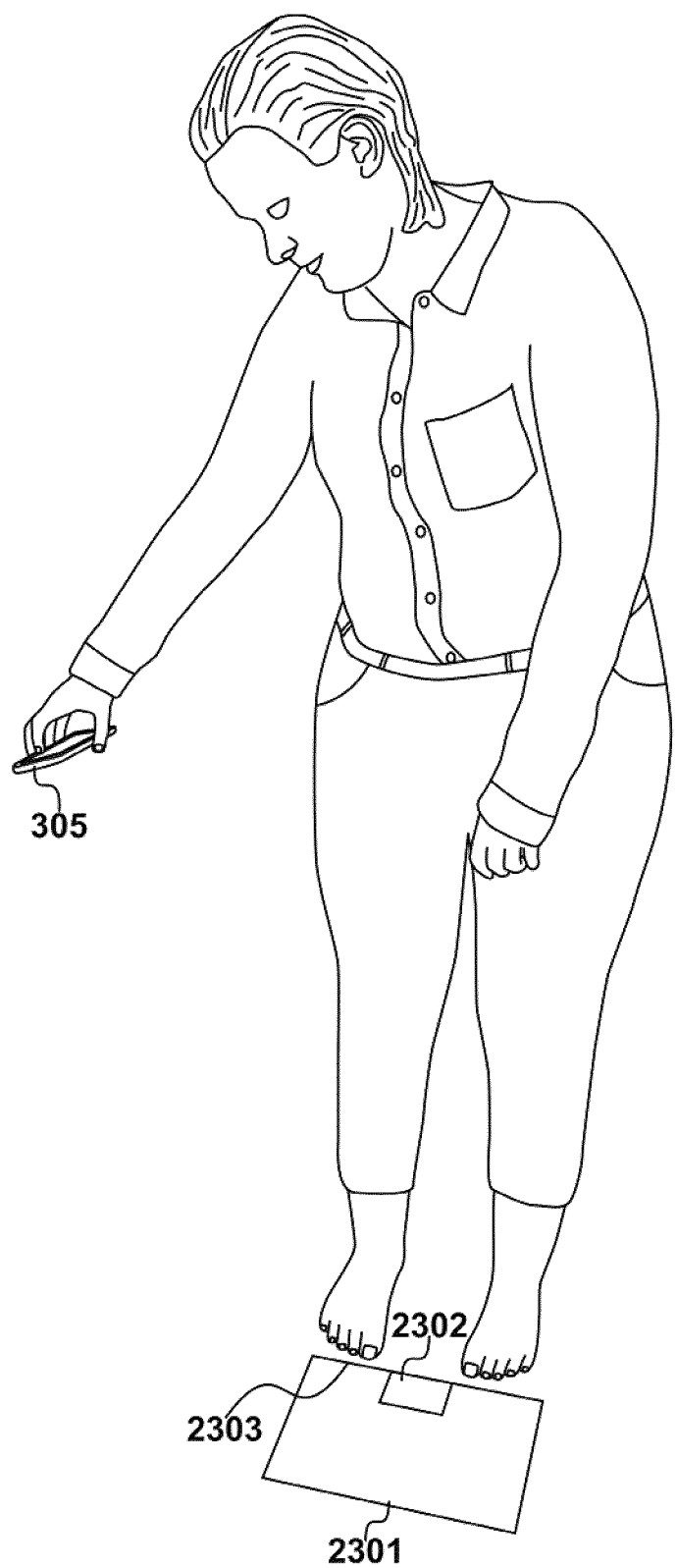
FIG. 23 illustrates an exemplary sweeping motion performed by a recipient.
Figure 26:
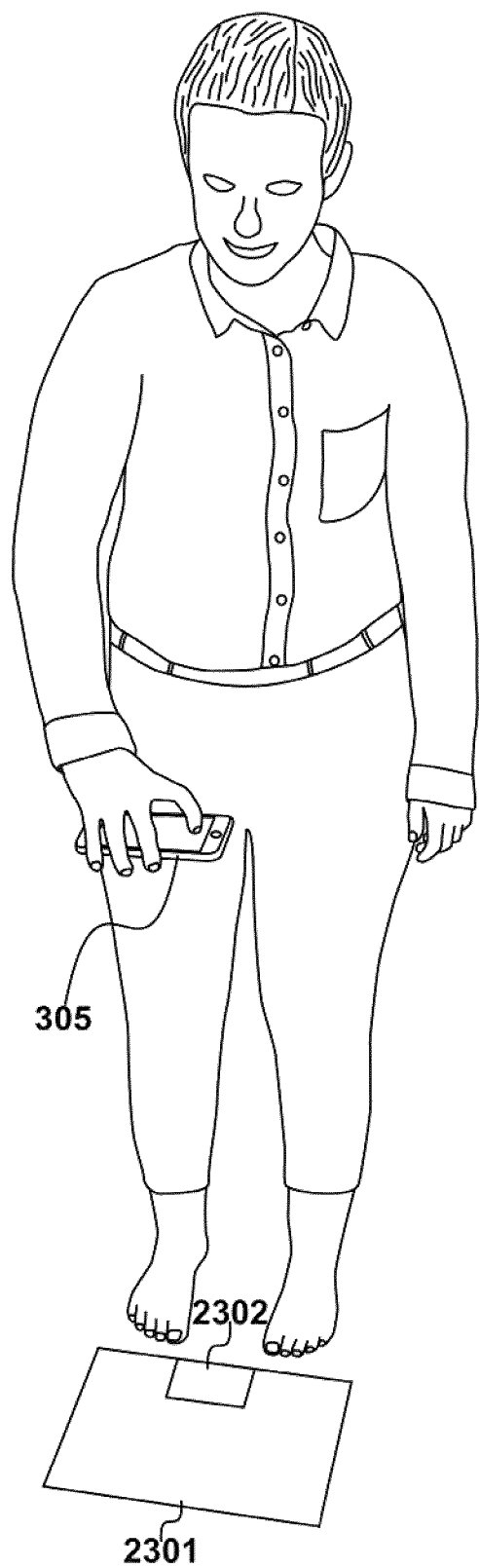
FIG. 26 shows a further instant of an exemplary tracking procedure.
Figure 30:
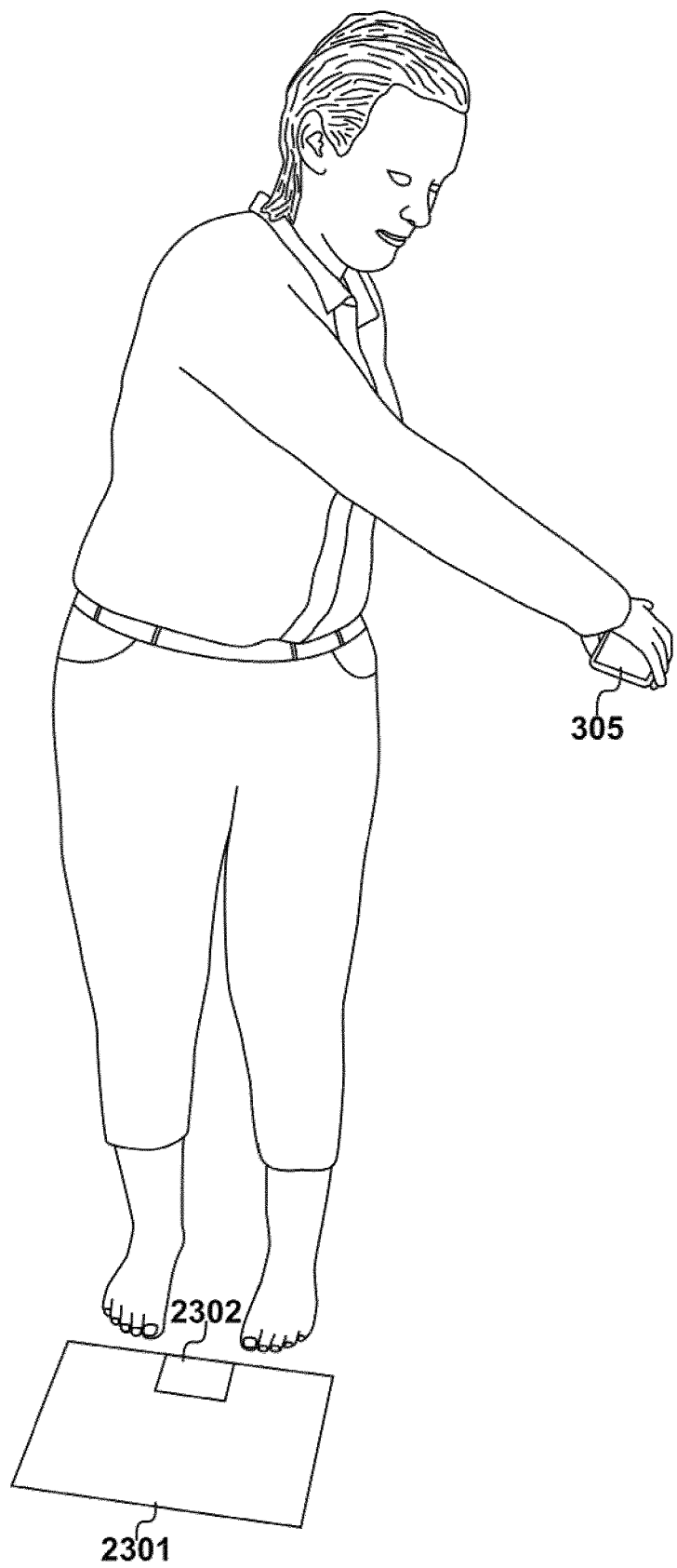
FIG. 30 shows a further instant of an exemplary sweeping motion.

Because the apparatus 305 may be held by the recipient themselves, a predetermined motion of apparatus 305 may be used to constrain the actual positions from which images can be taken. One such motion is a sweeping motion. As shown in FIGS. 23, 26, and 30, an exemplary sweeping motion may be performed by: holding apparatus with an outstretched arm; orienting camera 403 of apparatus 305 towards a pair of feet and a scaling object; and rotating apparatus 305 around the pair of feet and the scaling object with the outstretched arm so as to maintain a similar distance between camera 403 and the pair of feet and the scaling object during the rotation.

Accuracy may be improved with the sweeping motion. For example, the sweeping motion may provide a simple, repeatable and reliable procedure for the recipient (or a plurality of recipients) to capture images of feet at different angles. Processing power also may be reduced with the sweeping motion. For example, some tracking procedures for apparatus 305 and/or the feet may require a continuity of appearance of the feet in video feed 601, which may be more easily obtained with the sweeping motion. As a further example, the sweeping motion also may allow the processors to assume that the images are captured in a particular order, such as a compass angle order according to rotational guide 840, which may simplify the feature matching in the 3D reconstruction, saving on computation.

The compass rose shown in FIG. 8 may guide aspects of the sweeping motion. For example, the one or more processors may change the colour of each marker 801 to 818 of rotational guide 840 during the sweeping motion (e.g., from red to yellow) to communicate a rotational position of apparatus 305 relative to the aforementioned start position. The rotational position may be determined by the one or more processors. For example, the processors may determine a sequence from the image data, and determine the rotational position of apparatus 305 based on the sequence. Likewise, the image data may include position data output with IMU 409, and the processors may determine rotational positions based on the position data.

Another exemplary overlaid visual graphic is depicted in FIG. 8A as being similar to the example of FIG. 8. As shown, the graphic of FIG. 8A also may be similar to a compass rose, and may likewise include: a central capture area 830' and a rotational guide 840', including a plurality of markers 801' to 820'. As before, each marker 801' to 820' may correspond with a different rotational position of apparatus 305, be presented in different colours, and be likewise modified according to this disclosure.

In many instances, the recipient of the footwear is also the user of image recordal apparatus 305, making the terms "recipient" and "user" interchangeable in this disclosure. This is not required. For example, the recipient's feet may be photographed by an assistant, using another apparatus 305 or similar device, making the assistant the user. A greater variation of camera angles may result in this example. Here again, the image recordal apparatus 305 may be moved in an alternate predetermined motion to reduce the amount of processing power required. A modified version of the graphics shown in FIGS. 8 and 8A may be used to help the assistant perform the alternate motion.

FIGS. 9 to 13

Exemplary procedures 702 for locating and/or drawing tracker boxes with processor 401 in response to receiving computer-implemented or manual input gestures are detailed in FIGS. 9 to 13.

Figure 13:
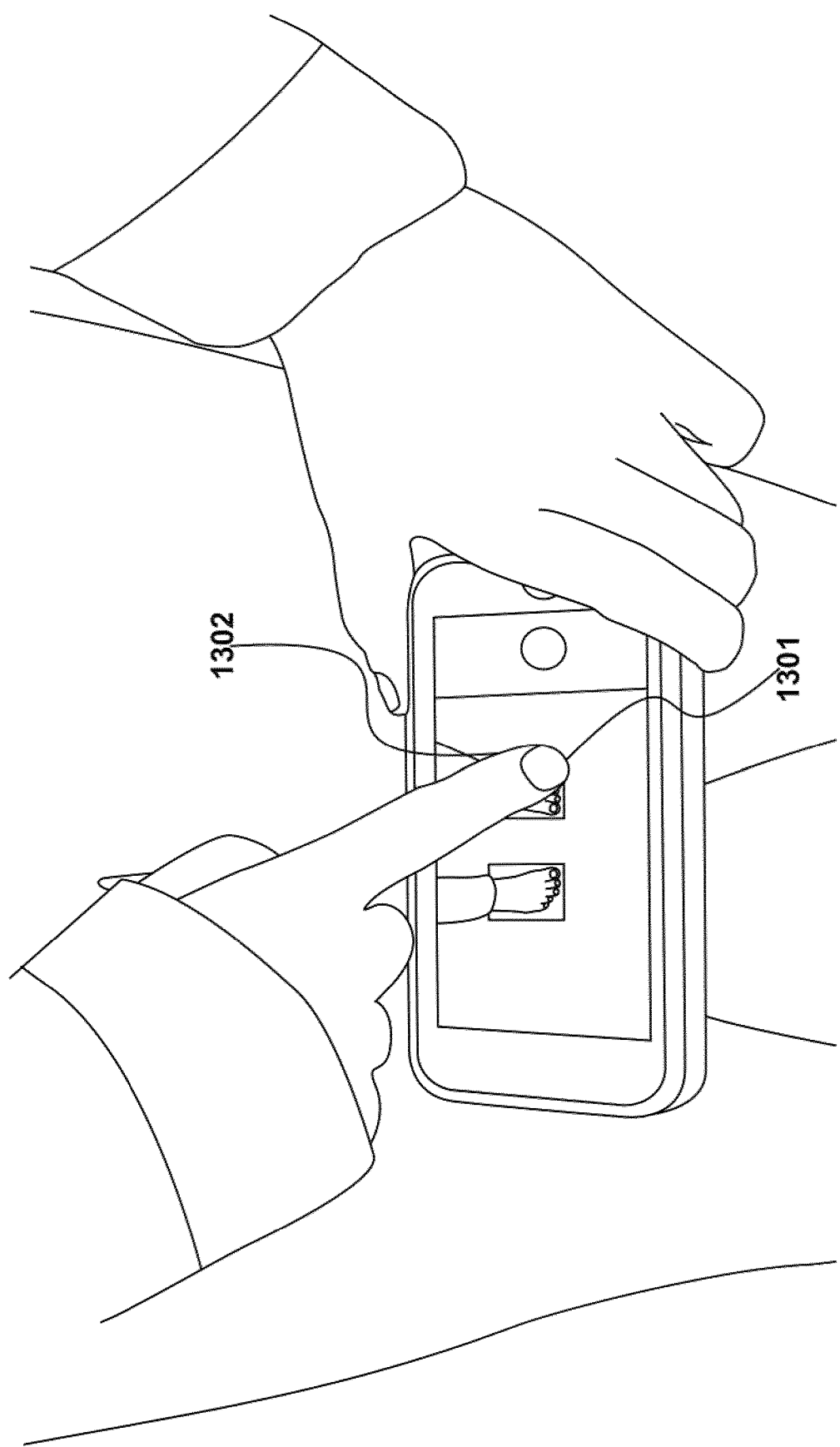
FIG. 13 illustrates the completion of drawing the second exemplary box.

Each tracker box may define a metering area of video feed 601 that corresponds with the location of a foot in view of camera 403. As shown in FIG. 13, for example, each foot in view of camera 403 may be located in one of the tracker boxes. Some aspects of the tracker boxes are described with reference to manual input gestures. According to this disclosure, these aspects also may be performed entirely by one or more processors using computer-implemented input gestures.

Figure 9:
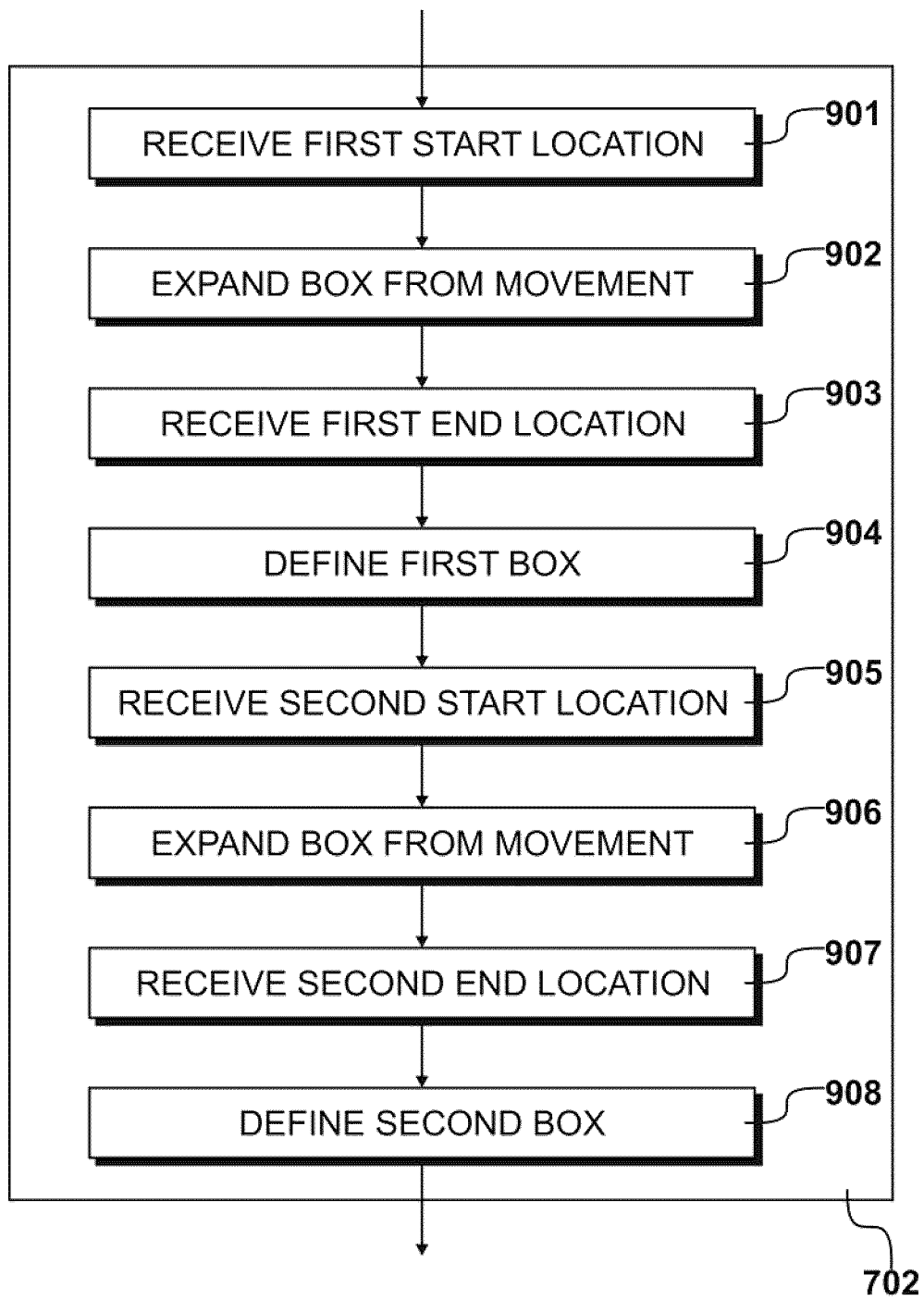
FIG. 9 shows an example of drawing a box in response to receiving input gestures.
Figure 10:
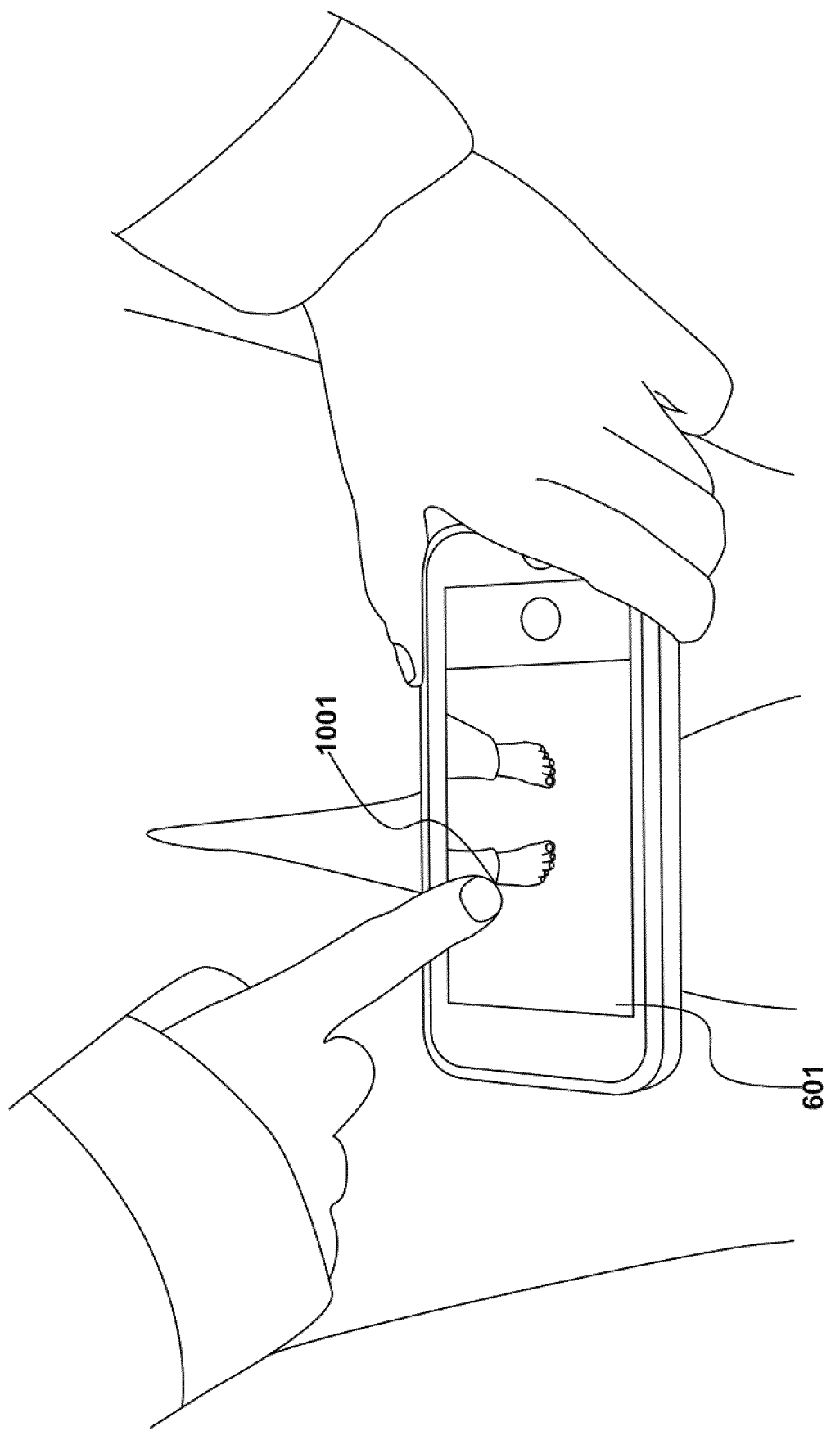
FIG. 10 illustrates the start of drawing a first exemplary box.

As shown in FIG. 9, procedures 702 may comprise a step 901, at which the one or more processors may identify a first start location 1001. If IMU 409 is present, then the one or more processors may receive position data from IMU 409, and associate the position data with start location 1001. An exemplary start location 1001 is shown in FIG. 10. In this example, start location 1001 may represent a point at which a transition occurs between foot pixels and non-foot pixels. Start location 1001 may be identified at step 901 by either a manual input gesture or a computer-implemented input gesture. As shown in FIG. 10, the manual input gesture may comprise steps performed by the recipient and steps performed by the one or more processors. For example, the recipient may identify the aforementioned transition point on video feed 601, place a finger on a point of display device 402 that corresponds with the location of the transition point in video feed 601, and/or draw the tracker box on display device 402. In this example, the one or more processors may locate the tracker box based on the corresponding point located on display device 402.

Alternatively, the one or more processors may locate the tracker boxes, with or without drawing them. For example, the one or more processors may identify the aforementioned transition point on video feed 601 based on a boundary or edge of the foot pixels and non-foot pixels, and surround the transition point by locating a predetermined shape (e.g., a square or rectangle) on display device 402. Any method of identifying the boundary or edge may be used, including those based on Harris, SIFT, SURF, and like methodologies. In some aspects, step 901 may be performed entirely by the one or more processors in response to a single activation gesture from the recipient. For example, procedures 702 may be activated in response to said single gesture (e.g., pressing a button), causing the one or more processors to automatically identify a transition point and locate the tracker box relative thereto.

Figure 11:
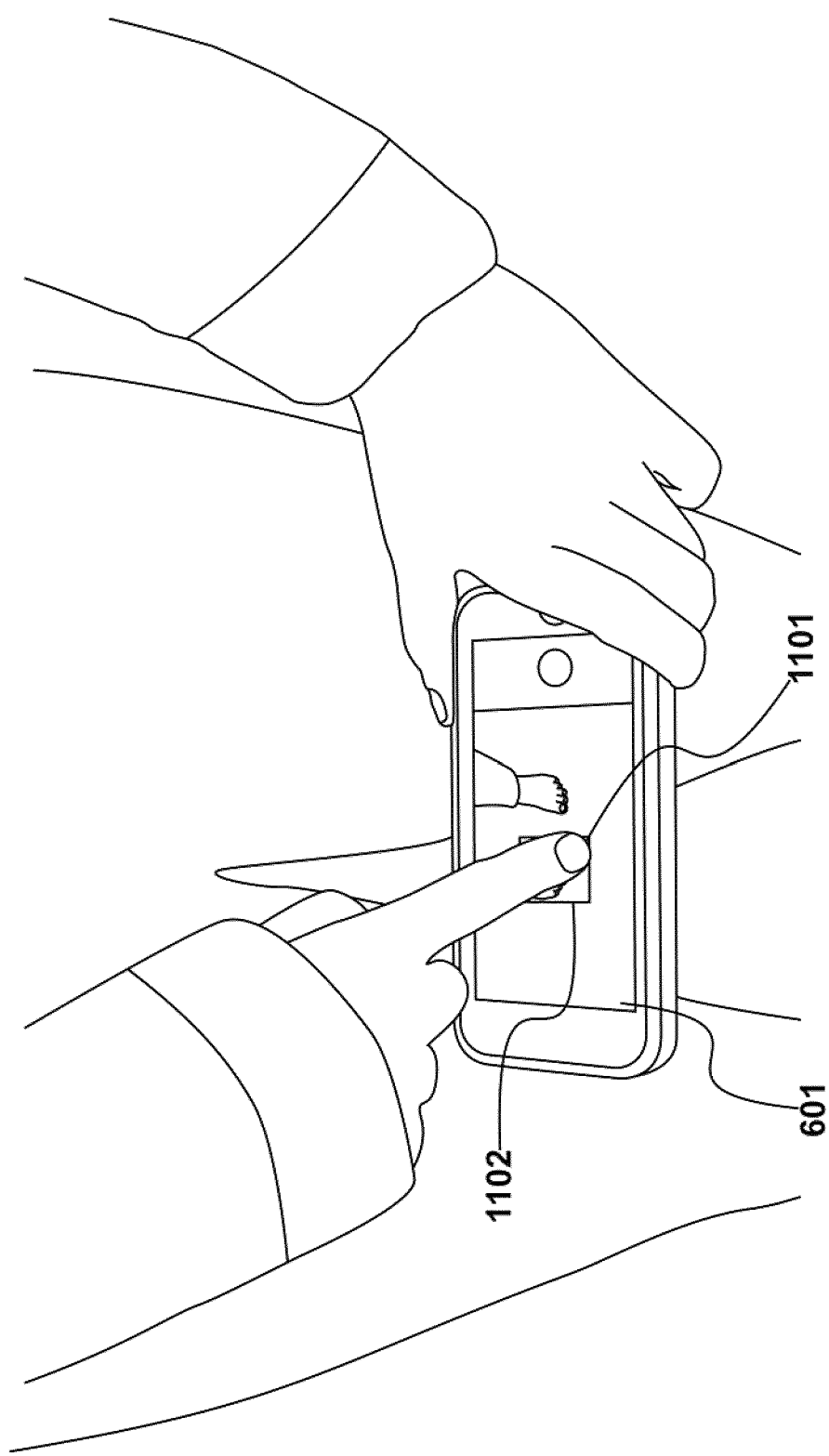
FIG. 11 illustrates the completion of the first exemplary box.

Procedures 702 may include additional steps for modifying the tracker boxes to ensure that foot pixels are contained therein. As shown in FIG. 9, procedures 707 may include a step 902, at which the one or more processors shape and/or expand the tracker boxes based on an additional input gesture. For example, the tracker box may be expanded by additional manual input gestures, such as sliding a finger over the display device 402 to identify a first end location 1101 of the tracker box located on device 402 in step 901, as shown in FIG. 11. Additional steps may be performed by the one or more processors, such as receiving data representing first end location 1101, and identifying said tracker box as a first tracker box 1102. Alternatively, step 902 may be performed entirely by the one or more processors, without additional manual input gestures. For example, as a continuation of step 901, the one or more processors may identify the first end location 1101 and box 1102 by modifying a perimeter of the predetermined shape.

Figure 12:
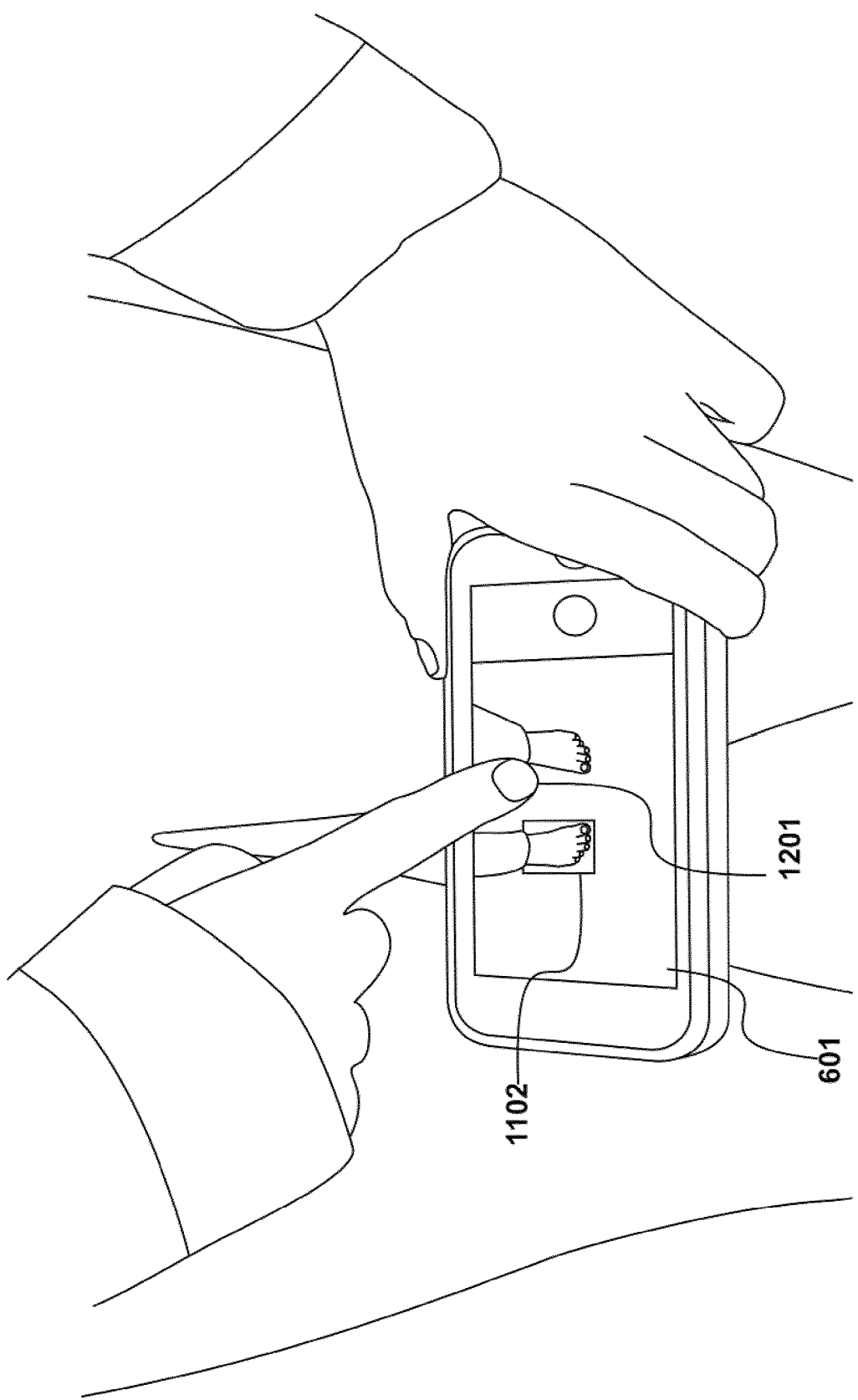
FIG. 12 illustrates the start of drawing a second exemplary box.

Additional tracker boxes also may be identified. As shown in FIGS. 9 and 12, for example, procedures 702 may further comprise a step 905, at which the one or more processors identify a second start location 1201. As before, start location 1201 may represent another point at which a transition occurs between foot pixels and non-foot pixels. Second start location 1201 may be identified using any combination of the manual and computer-implemented input gestures described above. For example, a similar combination of input gestures may be performed by the recipient and/or the one or more processors to locate and/or draw a second tracker box 1302 around an image of their second foot, as illustrated in FIGS. 12 and 13. For example, here again the recipient may place their finger at start location 1201 for second box 1302, and move their finger over the touchscreen 601 to define and expands box 1302 at step 906; and the one or more processors may perform similar alternative steps. In response, the one or more processors may define a second end location 1301 and second box 1302, as illustrated in FIG. 13. Similar to above, the one or more processors may likewise receive and use position data from IMU 409 at steps 905 and/or 907.

FIG. 14

Identifying the foot pixels in each captured image from video feed 601 may assist with the three-dimensional reconstruction procedures performed by one or more processors. In some aspects, locating the foot pixels may focus available processing power on areas where foot features may be found, and allow the foot pixels to be processed differently from the non-foot pixels. For example, the foot pixels may be analysed with the one or more processors with processes focused on the texture of the feet, not the texture of the background, allowing more complex operations to be performed. In some circumstances, it is possible for the background to be more richly textured than the skin of the feet. In these circumstances, if the foot pixels are not distinguished from the non-foot pixels, then the texture of the feet may be lost and/or only quantified with a significant overhead cost, potentially without achieving a satisfactory result.

Accordingly, it may be prudent to assume that foot pixels present less texture than the non-foot pixels; and procedures 702 may focus available processing resources upon the foot pixels, allowing for computational emphasis upon whatever features and/or textures are represented thereby. For example, the one or more processors may use a lower detection threshold for the foot pixels and a relatively higher detection threshold for the non-foot pixels to avoid wasting computational resources. Because most of the pixels may be associated with the ground (as described further below), distinguishing the foot pixels also may allow the one or more processors to set point different quotas for foot pixels and non-foot pixels during 3D reconstruction, further reducing processing power requirements.

The identification of foot pixels also may assist with optimizing image quality by automatically setting at least one of a focus, an exposure, and/or a white balance of the camera 403 to obtain high quality static image data. In terms of presenting video feed 601 to the recipient (or an assistant), as shown in FIG. 6, the image quality of feed 601 may be lower than the image quality of captured images obtained based on feed 601. For example, the quality of video feed 601 may have a first image quality that is only sufficient to allow the recipient to see their feet on display device 402. However, in various embodiments, when actual static images are captured from video feed 601 and recorded as image data, the image quality of each captured image may be optimized to have a second image quality that is superior to the first image quality.

Furthermore, the identification and tracking of foot pixels also allows for procedures to check that the captured images are valid, in that they do represent images of feet. Thus, if for whatever reason, the recipient moves camera 403 away from the feet and starts to record images of non-foot related items, it is possible for image recordal apparatus 305 to identify the error and bring the matter to the attention of the recipient. For example, by continuously tracking the foot pixels, the one or more processors may prompt the recipient as to where to point camera 403 in order to keep their feet in video feed 601, increasing the likelihood of achieving a successful result. More specifically, if the feet are wandering away from the centre of video feed 601, then the processors may prompt the user to recentre the video feed 601 on the feet. Likewise, if the feet occupy too much (e.g., all) or too little (e.g., less than 10%) of the field of view of video feed 601, then the processor may prompt the recipient to move the camera further or closer.

Additional aspects of tracking the foot pixels are now described. For example, the one or more processors may use a tracker model to track the foot pixels. The tracker model may include a colour tracker model that allows one or more processors to track the foot pixels based on colour. For example, the one or more processors may generate and apply the colour tracker model when the foot pixels contain colours that are either not contained within the non-foot pixels, or only contained in limited proportions therein, increasing the accuracy of the colour tracker model. The one or more processors also may use non-colour based tracking models. For example, the one or more processors may alternatively use a track-learn-detect tracker, such as Predator; a deep convolutional neural network foot detector configured to delineate bounding boxes automatically around the feet in each frame for use directly or with a target tracker, such as a Kalman filter; and/or a fully convolutional neural network configured to compute a segmentation mask for the feet in each image independently.

Aspects of camera 403 may influence the tracking operation. For example, camera 403 should not be moved too quickly, compared to the size of the feet. In addition, an illumination for camera 403 should be substantially even within the video feed 601, such that brightness and colour of each captured image do not vary significantly. Exact movement speeds and illumination requirements may vary depending upon the type of camera 403, which may be chosen to minimize these concerns.

As described above, the tracking operations may rely on the one or more processors being configured to receive or determine start locations within the image frame, such as start location 1001 of FIG. 10, and start location 1201 of FIG. 12. Any combination of manual and/or computer-implemented gestures described herein may be used to locate and/or draw tracker boxes based on locations 1001 and 1201, as with first tracker box 1101 of FIG. 11 and second tracker box 1302 of FIG. 13. As also described above, either the recipient or the one or more processors may draw and/or locate tracker boxes 1101 and 1301 so that they cover most of the foot pixels, and/or re-size said boxes 1101 and 1301 to minimize the amount of non-foot pixels present within boxes 1101 and 1103.

In some aspects, the first and second tracker boxes 1101 and 1301 may be used to initialize the tracker models, as identified at step 703. One or both of boxes 1101 and 1301 may be tracked. In some aspects, only one of boxes 1101 or 1301 is tracked, such as the first one to be identified.

Figure 14:
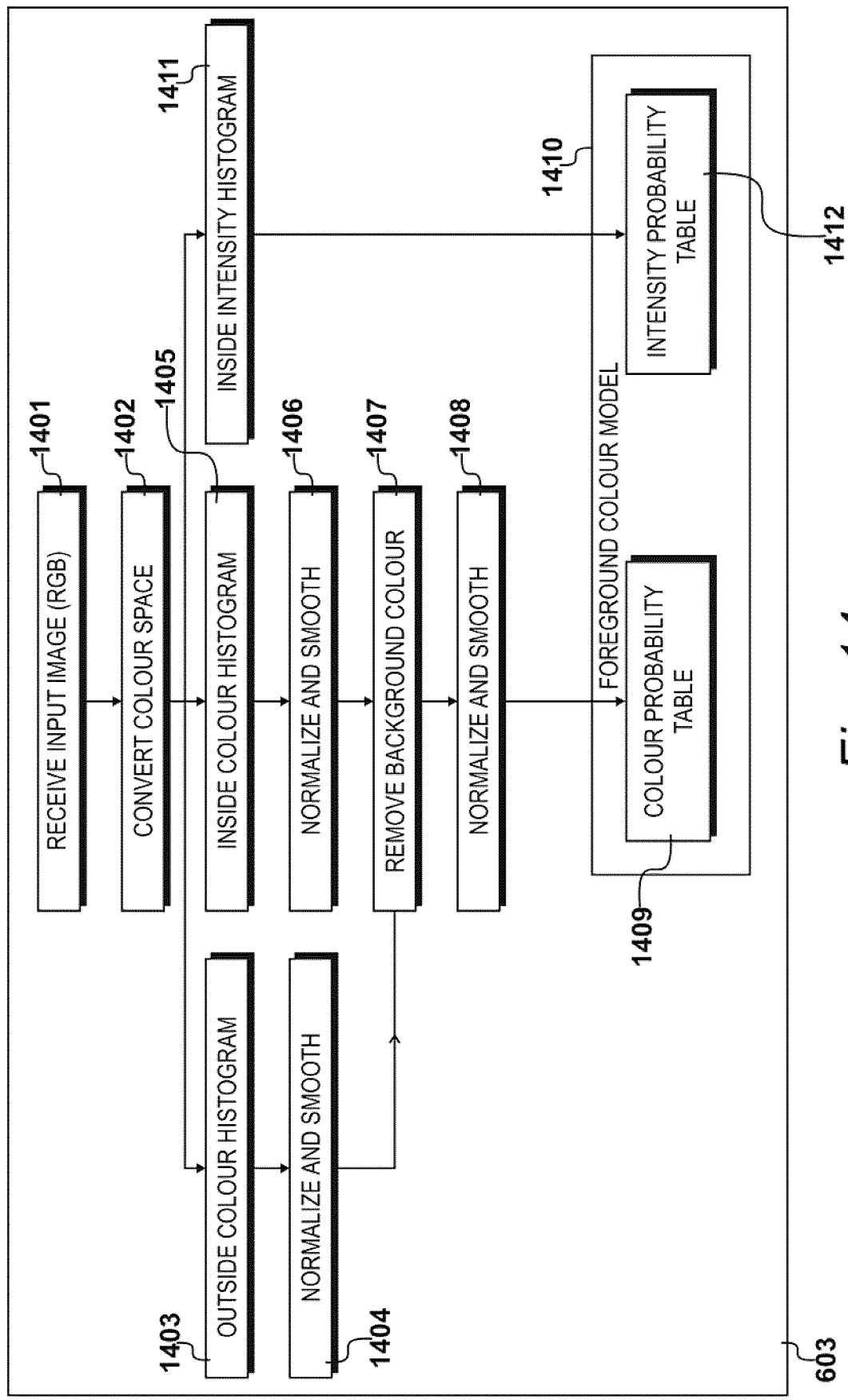
FIG. 14 shows exemplary procedures for initializing tracker models.

Procedures 603 for initializing tracker models with processor 401 are detailed in FIG. 14. For example, the one or more processors may initialize the tracker models by generating a foreground histogram based on the foot pixels and a background histogram based on the non-foot pixels. Each of the foreground and background histograms may be generated by the one or more processors in a two-dimensional Cartesian hue-saturation space based on the pixels of a captured image from video feed 601. For example, the one or more processors may compare the foreground and background histograms; identify the colours that are strong (e.g., prevalent) in the background histogram; and remove those colours from the foreground histogram, so that the tracker model only encodes distinct foreground colours. In this example, the one or more processors also may generate a brightness histogram based on the foreground pixels, and/or smooth the brightness histogram to improve robustness to changing illumination.

As shown in FIG. 14, procedures 603 may comprise a step 1401 of selecting or receiving, with the one or more processors, an initial captured image from video feed 601. The initial captured image may be defined as a raster of pixels specified in an RGB (red, green, blue) colour-space.

Then, at step 1402, a colour-space conversion process may occur. For example, at step 1402, the one or more processors may convert each value defined in the RGB colour-space into a hue value, a saturation value, and a luminance value, resulting in a colour-space identified herein as an HxSyV colour space. From this, the one more processors may generate at least three tracker models: a colour tracker model for the foreground intensity, a colour tracker model for the foreground colour, and a colour tracker model for the background colour.

At step 1403, the outputs from the colour space conversion process performed by the one or more processors at step 1402 may be supplied as inputs to produce a colour histogram for the pixels located outside of tracker boxes 1101 and 1301. At step 1404, the one or more processors may normalize and smooth the colour histogram to provide an input for step 1407. In this example, the outputs from the colour-space conversion step 1402 also may be supplied as inputs to a step 1405 that produces a colour histogram for the pixels located inside tracker boxes 1101 and 1301. This colour histogram also may be normalized and smoothed by processor 401 at step 1406. Thereafter, at step 1407, the outputs from step 1404 may be subtracted by processor 401 from the outputs from step 1406 to remove the background colour.

The end result of procedures 603 may be probability tables that are generated by the one or more processors to distinguish between foot pixels and non-foot pixels. For example, the processors may perform a further normalization and smoothing operation at step 1408 to produce a colour probability table 1409 that forms part of a foreground colour model 1410. As a further example, the one or more processors may supply the outputs from colour conversion process 1402 to a step 1411 that produces an intensity histogram for the pixels in each metering area. From this, one or more processors may produce an intensity probability table 1412 that complements the colour probability table within the foreground colour model 1410.

The tracking procedures described herein may be used to estimate a location of the feet, and maintain the estimated location over time based on input observations about the feet. In some aspects, the tracking operations may not be required. For example, the one or more processors may alternatively accept each new measurement as the true location of the feet if the input observations are sufficiently accurate and reliable, as may be possible with deep learning methods, including any methods using a convolutional neural network detector, fully convolutional network segmentation, and the like.

FIG. 15

As described above, aspects of procedures 603 may rely on a separation of brightness (luminance) from colour (hue and saturation) to emphasise the colours, and to provide invariance to brightness and shadow. To achieve this result, the RGB values from the initial captured image may be converted by the one or more processors to an HSV (hue, saturation, value) colour-space, thereby achieving the separation of brightness (luminance) from colour (hue and saturation). However, in conventional HSV colour-space, hue is an angle and may inconvenient to work with. For example, angular values of hue may become unstable at low saturation values and may wrap around, potentially leading to the introduction of artefacts. Accordingly, the hue and saturation values may be converted by the one or more processors from polar to Cartesian coordinates, creating a colour-space that is represented herein as the HxSyV colour space.

Figure 15:
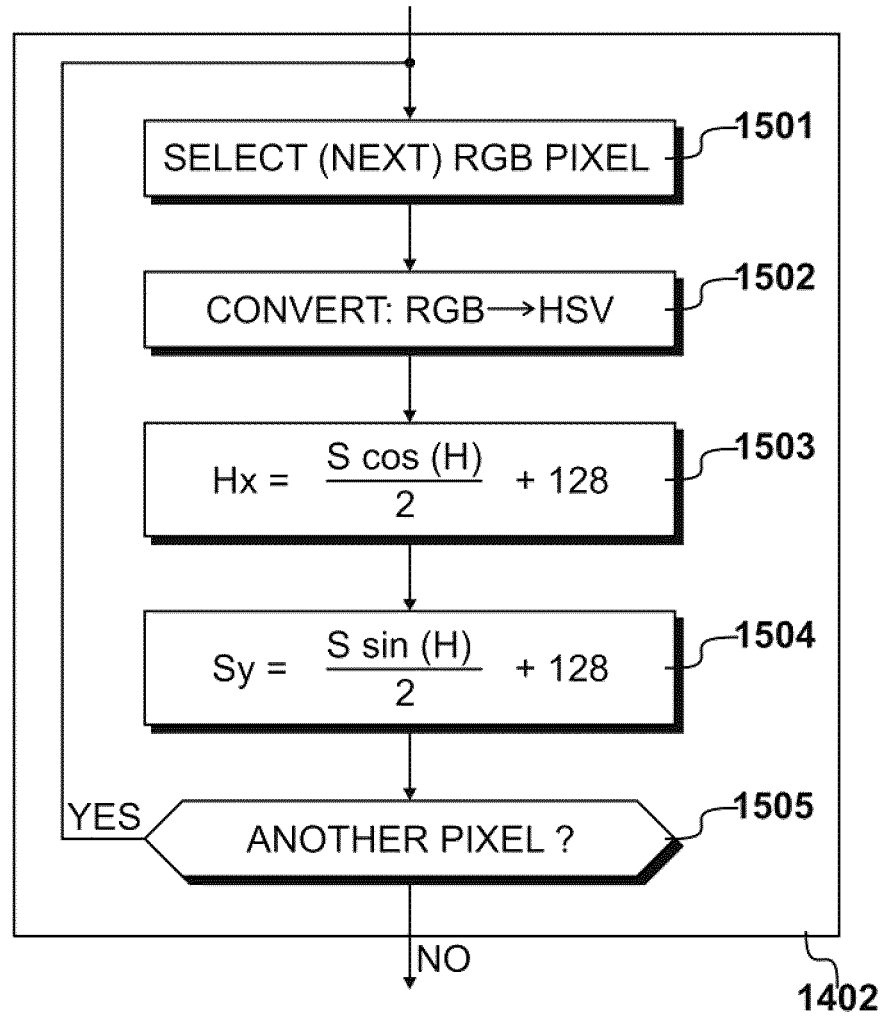
FIG. 15 shows exemplary colour-space conversion procedures.

Exemplary procedures 1402 for achieving the colour space-conversion are detailed in FIG. 15. As shown, procedures 1402 may comprise a step 1501, in which a first RGB pixel is selected by the one or more processors; and at step 1502, in which the one or more processors perform a conventional conversion from the RGB Cartesian colour-space to HSV polar coordinate colour-space. In some aspects, no further calculations may be required for one or more processors to use the brightness value V.

At step 1503, the one or more processors may calculate a value for Hx on the basis that hue value may defined in radians, and the saturation value may have a predetermined range, such as from 0 to 255. Accordingly, using the one or more processors, the cosine of the hue value may be calculated multiplied by the saturation value, halved, and added to a constant (e.g., 128), resulting in the Hx value.

At step 1504, a similar calculation may be performed with the one or more processors to determine a Cartesian value for saturation. For example, using the one or more processors, the sine of the hue value may calculated, multiplied by the saturation value, halved, and added to a constant (e.g., 128), resulting in the aforementioned Cartesian value for saturation. Once calculated, the one or more processors may write the new values for Hx, Sy and V to an appropriate pixel location.

At step 1505, the one or more processors may determine whether another RGB pixel is to be considered with procedures 1402. If so, then the one or more processors may select next RGB pixel at step 1501, and repeat steps 1502 to 1505 until all of the pixel values for the initial captured image have been considered, allowing the exemplary question asked at step 1505 to be answered in the negative.

FIG. 16

In some aspects, the intensity or luminance values of the pixels inside the tracker boxes 1101 and 1301 may be used to make a one-dimensional intensity histogram, an example of which is illustrated at 1601 in FIG. 16 for illustrative purposes only. In this example, the one-dimensional histogram may be an array of thirty-two counts, with each array covering an intensity range of eight grey levels. For example, these histogram "bins", such as bin 1602, may cover an input intensity range of 0 to 255.

Continuing the previous example, after the thirty-two bin-counts have been accumulated, the one-dimensional histogram may be smoothed by the one or more processors with a Gaussian envelope having a standard deviation (e.g., of four bins). It is appreciated that colour histograms are quantised and estimated from a finite sample. Consequently, they often contain empty bins that may cause problems with subsequent processing operations. To avoid these problems, the one-dimensional histogram may be smoothed by the one or more processors as an image would be. For example, the smoothing operation may spread some of the bin counts to neighbouring bins.

In some aspects, a smoothing filter or kernel, typically with a Gaussian shape, may be deployed with the one or more processors. For brightness histogram 1601, the smoothing filter or kernel may be a one-dimensional Gaussian filter; whereas, for the colour histograms, the smoothing filter or kernel may be a two-dimensional Gaussian filter. The smoothing operation may comprise convolving the histogram with the smoothing filter or kernel, resulting in a smoothed output histogram. For example, through convolution, the one or more processors may apply the smoothing filter or kernel to each distinct location (bin) of the input histogram 1601. In this example, for each location, the one or processors may use the smoothing filter or kernel to weigh the corresponding input values in the neighbourhood of the location. Thereafter, using the one or more processors, the weighted values may be summed and then assigned to the same location in an output histogram. An exemplary representation of these steps is shown at 1602.

An exemplary smoothing operation is shown in FIG. 16 at 1603, identifying an equation for the smoothing convolution. In this equation, x(n) is an input histogram, y(n) is an output histogram, f(i) is a filter, and w is the width of the filter (i.e., the number of bins or coefficients in the filter).

For the two-dimensional histograms, the algorithm may be substantially similar. For example, using the one or more processors, the iterations may be performed over a two-dimensional grid of histogram bins, the Gaussian filter may be two-dimensional, and the filter weightings may be summed over the two-dimensional neighbourhood.

As illustrated at 1604, the filtered histogram may be normalized by the one or more processors so that the values contained therein sum up to unity. Now, given an intensity value 1605, a lookup may performed by the one or more processors for each pixel, as illustrated by lookup table 1606, to give a likelihood that the pixel belongs to the foreground, identified as the probability of being part of the foreground 1607.

In addition to the one-dimensional histogram 1601, the colour pixels inside first tracker box 1102 and second tracker box 1302 may be used by the one or more processors to make a two-dimensional colour histogram in HxSy space. In some aspects, the HxSy space (ranging from 0 to 255 in both axes) may be divided into a grid thirty-two bins wide and thirty-two bins high, so that each bin is an eight-times-eight array of colour values. For each pixel considered, the one or more processors may use its hue and saturation to look-up the appropriate histogram bin and increment the count for that bin.

As stated above, aspects of the two-dimensional histogram may be treated like an image. For example, the two-dimensional histogram may be smoothed by the one or more processors using a two-dimensional Gaussian kernel. In this example, the Gaussian kernel may have a standard deviation (e.g., of two bins), and the two-dimensional histogram may be normalized so that all values sum to one.

Referring back to FIG. 14, as illustrated by step 1407, the one or more processors may remove colours that are strong in the background histogram (e.g., highly prevalent) from the foreground histogram so that the resulting histogram only encodes distinct foreground colours. For example, a threshold may be applied by the one or more processors to the two-dimensional background colour histogram to arrive at a colour space mask including a significant amount of the background colours included in the background histogram. In this example, the mask may be applied to the foreground histogram by the one or more processors to set those colours to zero. After this, the background histogram may be discarded and/or not used for foot tracking purposes. As illustrated at step 1408, the resulting histogram may again be normalized and smoothed.

In keeping with these examples, exemplary procedures 703 may be used by the one or more processors to generate a foreground colour model 1410 comprising of colour probably table 1409 and intensity probability table 1412. Colour probability table 1409 may be used to by the one or more processors to lookup the colour of each pixel, and determine a first likelihood of that pixel being a foot pixel based on its colour. Similarly, intensity probability table 1412 may be used by the one or more processors to lookup the intensity of each pixel, and determine a second likelihood of that pixel being a foot pixel based on its intensity. Individually or together, these probabilities may be used by the one or more processors to determine whether each pixel is a foot pixel or non-foot pixel.

FIG. 17

After initializing the tracker models at step 703, resulting in the generation of colour probability table 1409 and intensity probability table 1412, the pre-processing initiation procedures 502 may be complete. As stated above, procedures 502 may be performed by the one or more processors with an initial image captured from video feed 601 in response to manual and/or computer-implemented input gestures. Once procedures 502 have been completed, camera 403 may be moved relative to the recipient in a predetermined motion to obtain captured images based on video feed 601. A number of predetermined motions have been described above, including a sweeping motion. With the tracker models, the one or more processors may track the feet in the video feed 601 based on probability tables 1409 and 1412 during such motions. Additional examples are now described with reference to the sweeping motion, although any motion may be used.

For example, at step 1701, the one or more processors may read a first (or next) image from video feed 601 at a first position of the sweeping motion. At step 1702, the one or more processors may update the tracker models, as described below. The processors may continuously read images from video feed 601 as image recordal apparatus 305 is moved through the sweeping motion. Using the tracker models, the one or more processors may track the feet between each image based on tables 1409 and 1412.

The one or more processors may fail to continue tracking the foot pixels at some point during the sweeping motion, such as when camera 403 is inadvertently oriented away from the feet. In such instances, it may be necessary to initiate the capture process again by returning to step 502. Desirably, this functionality also allows the sweeping motion to be performed in multiple discrete parts, in which the capture process may be initiated at the start of each part (or partial sweep) by returning to step 502.

At step 1703, for example, the one or more processors may determine whether an image capture command has been received. If the image capture command has not been received, such that the question asked at step 1703 may be answered in the negative, then control may be returned to step 1701, and the next image read from video feed 601.

The maximum number of captured images that may be stored and/or uploaded with procedures 503 may be constrained. In some aspects, multiple images of the feet from substantially the same position may be captured. Because the multiple images may contain duplicate or near-identical image data, the processors may identify and/or delete some of these images. For example, upon receiving the capture command at a new position during step 1703, the processors may determine at step 1704 whether a captured image has been associated with new position. If the question asked at step 1704 is answered in the affirmative, then the one or more processors may prompt the recipient at step 1705 to move camera 403 to another new position.

In the ongoing example, if the question asked at step 1704 is answered in the negative, then the one or more processors may initiate an optimisation procedure 1706 prior to image capture. Aspects of image recordal apparatus 305 may be adjusted during procedure 1706. For example, optimising procedure 1706 may control and/or modify at least one setting of camera 403, such as a focus, an exposure, and/or a white balance.

After process 1706, the camera 403 may be configured to capture images of the feet based on video feed 601. Accordingly, at step 1707, the one or more processors may operate camera 403 to obtain captured images of the feet, and associate each captured image with a position of the sweeping motion. Accordingly, the output of step 1707 may be a plurality of captured images based on video 601, and position data associating each captured image with a different position of the sweeping motion.

Figure 17:
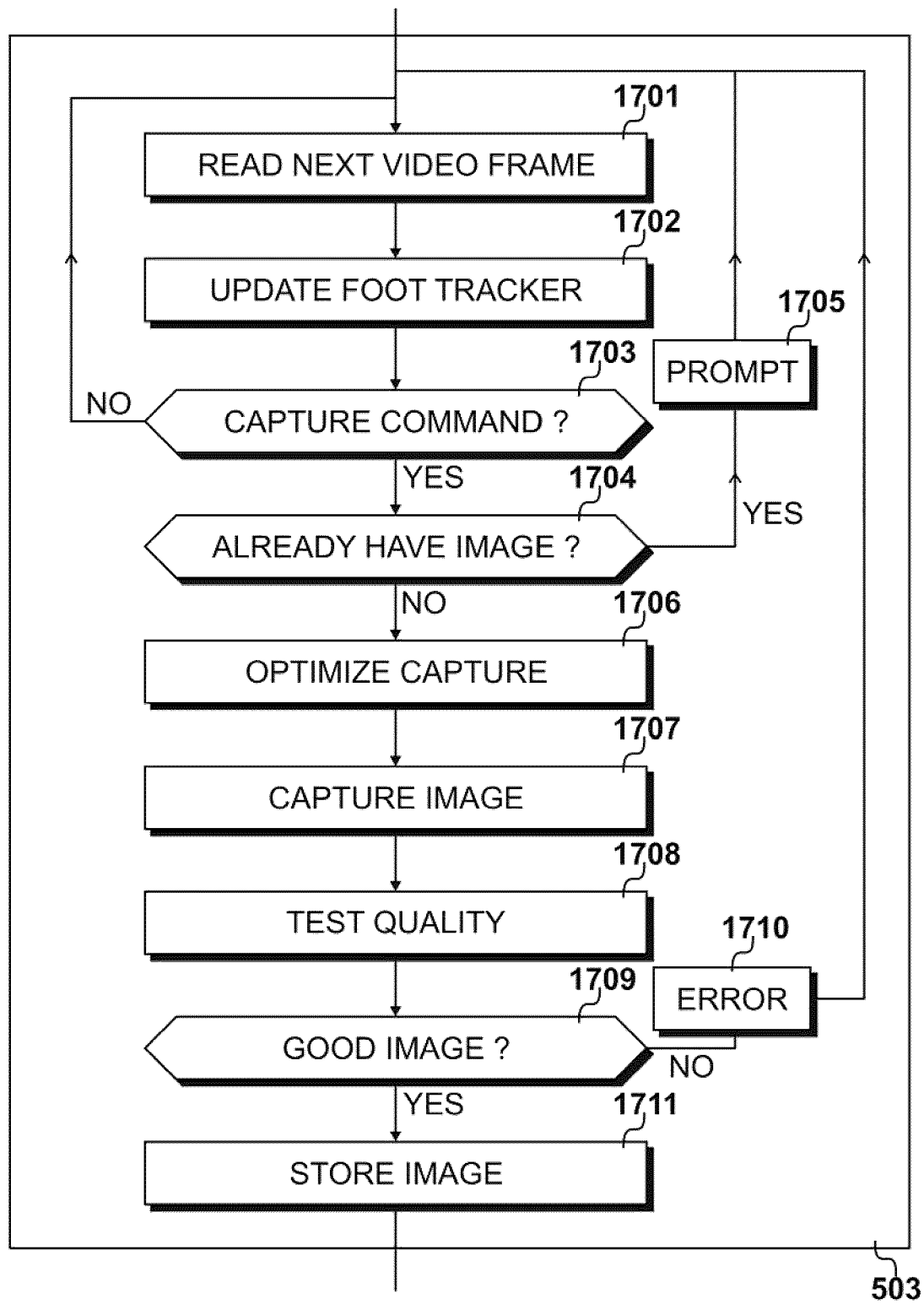
FIG. 17 details exemplary procedures for storing image data.

The quality of each captured image may be tested at step 1708 to ensure that image is compatible with evaluation procedures 309. For example, the one or more processors may perform a quality test on each captured image, and determine whether the quality test has been passed, such that the image data is considered good enough to be recorded. Any quality test may be used. For example, the focus, exposure, and/or white balance of each captured image may be tested to determine whether process 1706 was successful. As shown in FIG. 17, if the one or more processors determine that one of the captured images fails the quality test, such that the question asked at step 1709 is answered in the negative, then processors may display an error message to the recipient at step 1710, and return control to step 1701. Alternatively, if the processors determine that one of the captured images passes the quality test, such that the question asked at step 1709 is answered in the affirmative, then the one or more processors may store the captured image within storage device 405 at step 1711.

Procedures 503 may be repeated until a sufficient number of captured images have been stored within storage device 405. In some aspects, at least three captured images may be required, provided that each captured image depicts the feet from a different position of the sweeping motion.

FIG. 18

Figure 18:
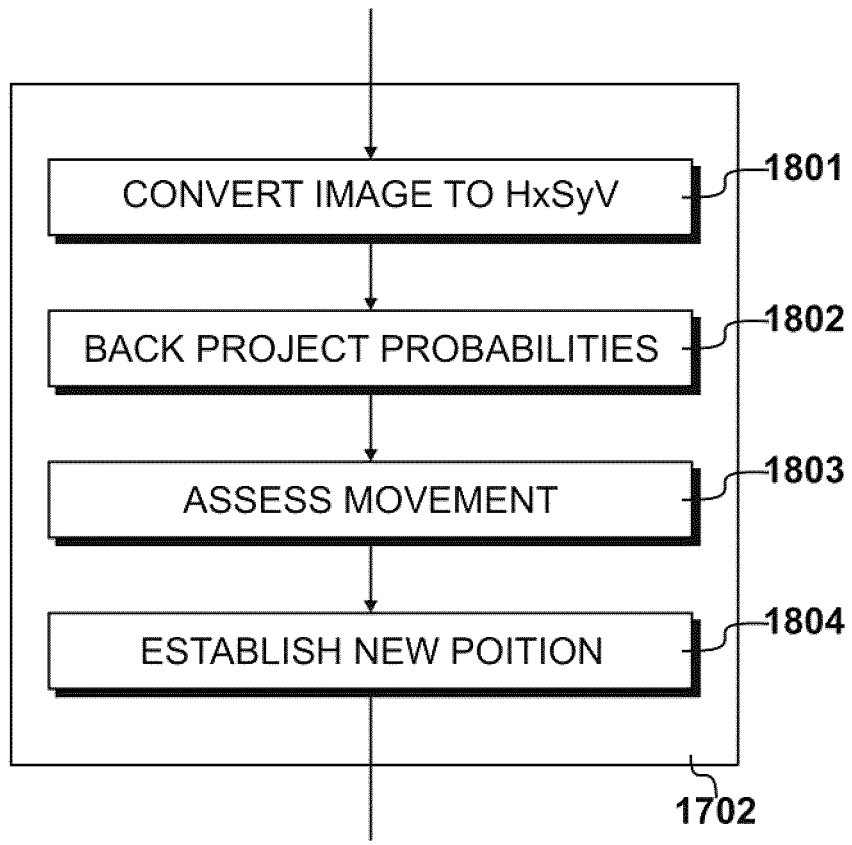
FIG. 18 details exemplary procedures for updating a foot tracker.

Exemplary procedures 1702 (FIG. 17) for updating the tracker models are detailed in FIG. 18. As shown in FIG. 11, the one or more processors may track the position of first tracker box 1102 in each image from video feed 601. The foot pixels located within box 1102 may be used to define the object being tracked.

For example, at step 1801, the one or more processors may convert each image from video feed 601 into hue-saturation-value coordinates (HxSyV) using the processes detailed in FIG. 15 and described further above. At step 1802, the converted image may be back projected by the one or more processors using the foreground histograms for colour and brightness, thereby converting each pixel from a representation of colour to a representation of probability, and identifying the probability of that pixel belonging to the foreground. Additional procedures for back projecting probabilities are detailed in FIGS. 19 and 20 described further below.

At step 1803, the one or more processors may assess the movement of first tracker box 1102. Additional procedures for the assessment are detailed in FIG. 21 and described further below. At step 1804, the one or more processors may establish a new position for the tracker box 1102 based on the assessment. Additional procedures for the establishing are detailed in FIG. 22 and described further below.

FIG. 19

Figure 19:
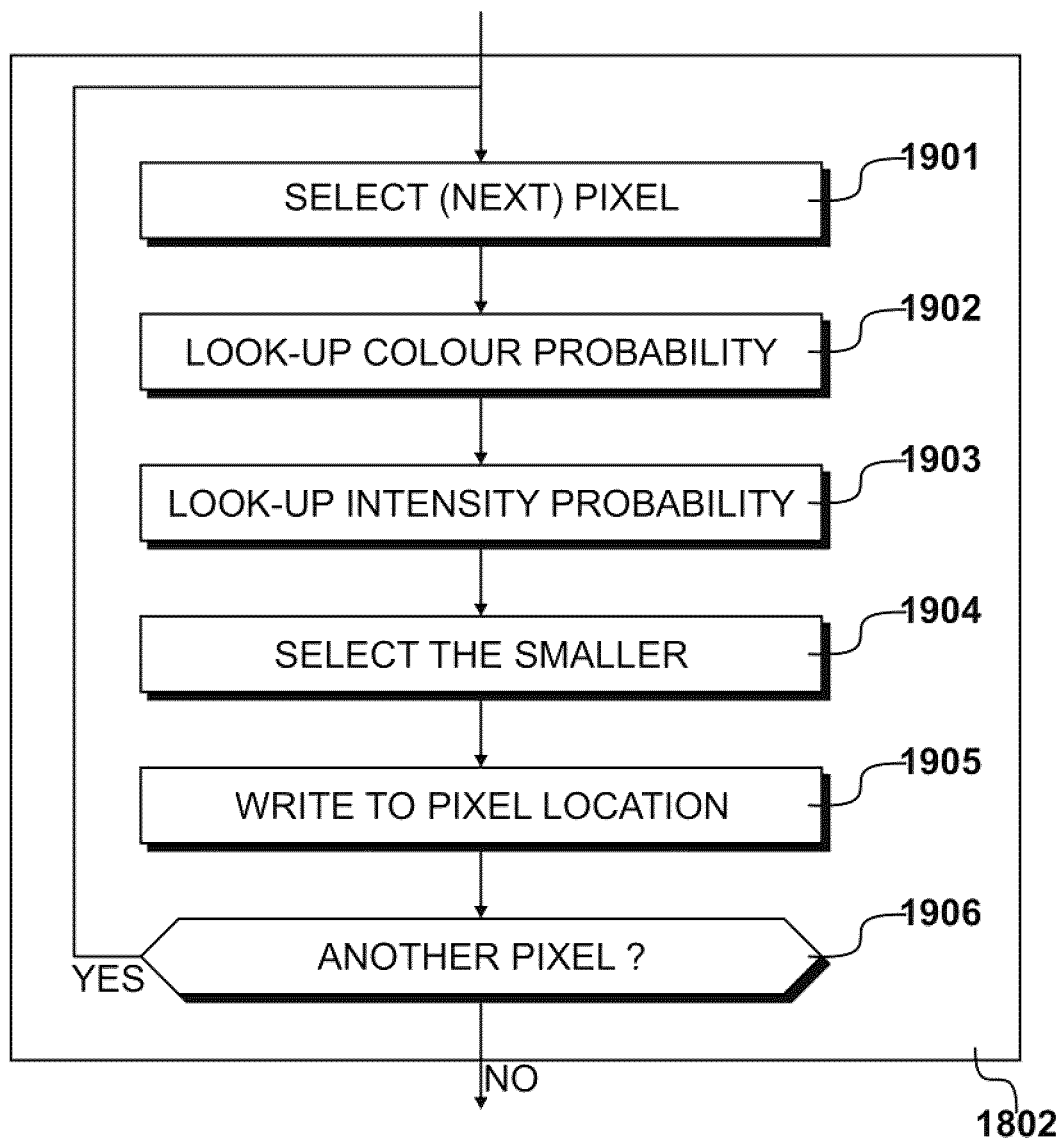
FIG. 19 details exemplary procedures for back projection.

FIG. 19 details exemplary procedures 1802 for back projecting probabilities within procedures 1702 of FIG. 18.

At step 1901, the one or more processors may select a first (or next) pixel of a first image from video feed 601. Additional steps may be performed to determine whether the selected first pixel is a foot pixel or a non-foot pixel.

For example, at step 1902, the one or more processors may perform a colour probability lookup based on colour probability table 1409; and, at step 1903, the one or more processors may perform an intensity probability lookup based on the intensity probability table 1412. The result of steps 1902 and 1903 are probability values of the selected pixel belonging to the foreground. Ideally, if the selected pixel does belong to the foreground image, then both procedures should result a high probability value. Consequently, to enhance confidence, the one or more processors may select the smaller of the two probability values at step 1904, and write the selected probability value to an appropriate pixel location at step 1905.

Exemplary procedures 1802 may be repeated for each pixel in the first image. For example, at step 1906, the one or more processors may determine whether another pixel is present within the image at step 1906. If that question is answered in the affirmative, then the one or more processors may select the next pixel by returning to step 1901.

FIG. 20

Figure 20:
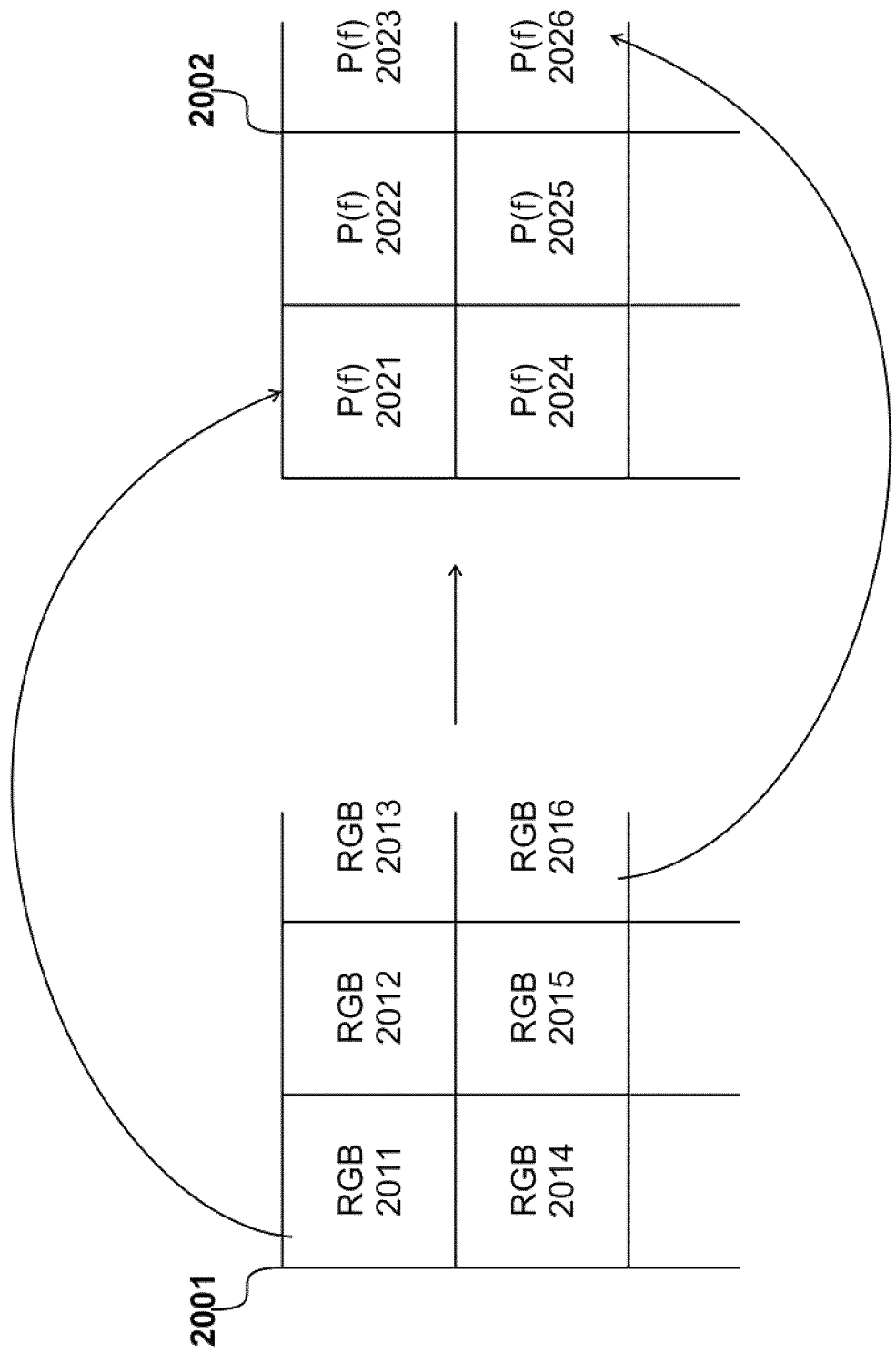
FIG. 20 details an exemplary result of back projecting probability values.

An exemplary result of performing back projection procedures 1802 is detailed in FIG. 20, in which an exemplary input image is represented by an input image 2001. As shown, each input image may consist of an array of pixels representing RGB colour values, such as a first line of values RGB 2011, RGB 2012 and RGB 2013; and a second line of values RGB 2014, RGB 2015 and RGB 2016. Of course, image 2001 may include any number of pixels, arranged in any number of lines. The processors may convert the RGB values to HxSyV values at step 1801; and translate the HxSyV values to probabilities at step 1802. Accordingly, the output of procedures 1802 may be an output image array 2002 in which the RGB values have been translated by the one or more processors into probabilities of each respective pixel being in the foreground image. Each probability is depicted in FIG. 20 with the designation "P(f)". For example, the translation of RGB 2011 depicted as P(f) 2021; the translation of RGB 2016 is depicted as P(f) 2026; and so on for each of RGB values.

FIG. 21

Figure 21:
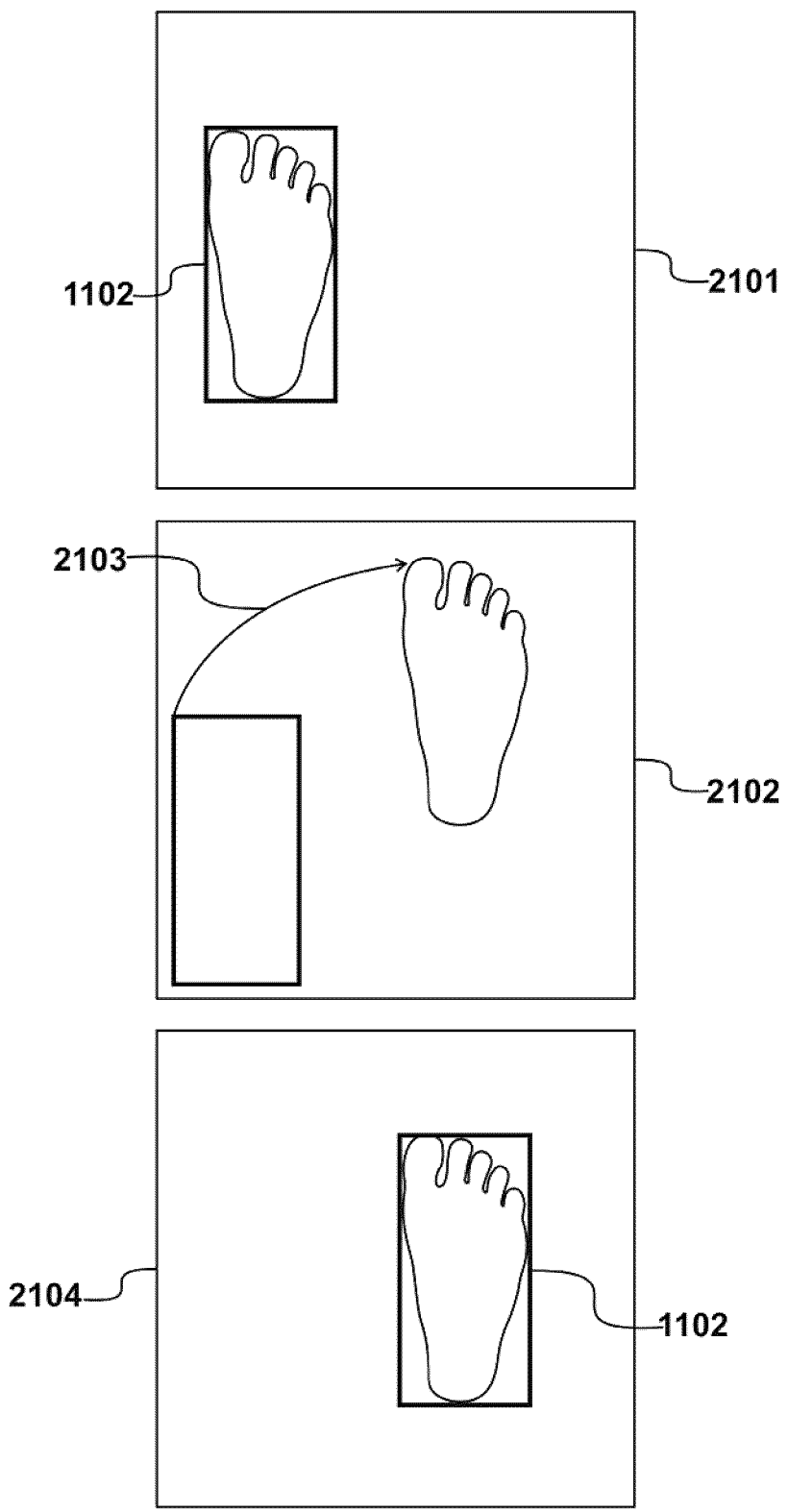
FIG. 21 illustrates an exemplary tracking operation.

FIG. 21 depicts exemplary procedures for using the one or more processors to assess a movement of first tracker box 1102. Two exemplary images from video feed 601 are shown in FIG. 21: an initial image 2101 associated with a first position of the sweeping motion; and a subsequent image 2102 associated with a second position of the sweeping motion. As now described, the procedures depicted in FIG. 21 may be used to move first tracker box 1102 from a first position in initial image 2101 to a second position in the subsequent image 2102 (shown as image 2104 in FIG. 21).

As illustrated in FIG. 21, the initial location and/or shape of first tracker box 1102 in initial image 2101 may be specified by the one or more processors using various manual and/or computer-implemented input gestures. For example, either the recipient or the one or more processors may draw and/or locate first tracker box 1102 around the foot pixels.

In subsequent image 2102, the foot pixels have moved because image 2201 is associated with a different position in the sweeping motion. The one or more processors may assess the movement of the foot pixels based on a comparison of images 2101 and 2102. For example, the one or more processors may: determine the location of tracker box 1102 in image 2101; estimate a location of tracker box 1102 in image 2102; calculate a displacement vector 2103 based on the determined and estimated locations; and move first tracker box 1102 to a new location in subsequent image 2104 by calculating a movement distance and direction based on vector 2103.

FIG. 22

Figure 22:
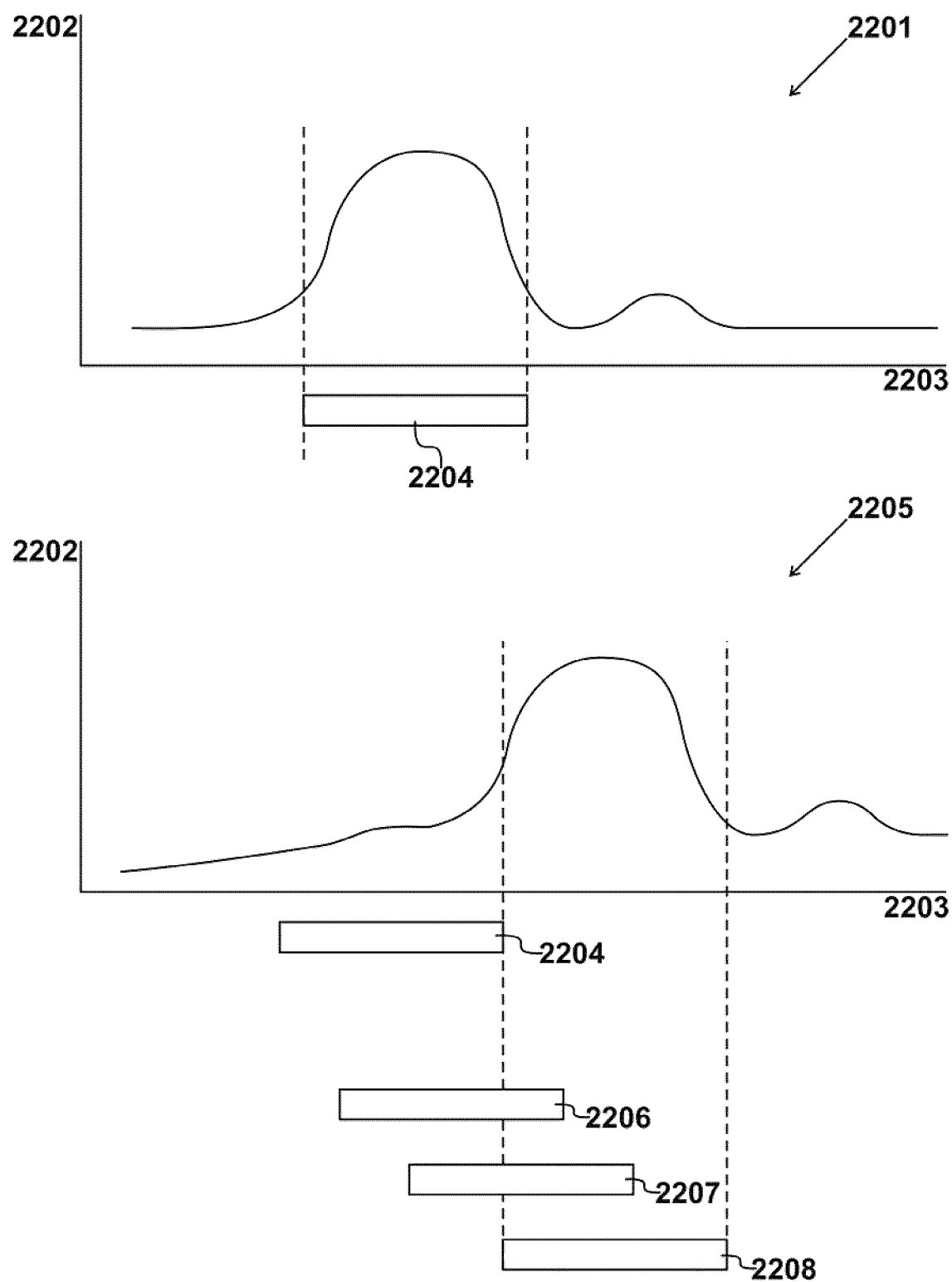
FIG. 22 illustrates an exemplary mean-shift process.

Additional procedures 2201 for establishing a new location of first tracker box 1102 are detailed in FIG. 22. Aspects of procedures 2201 may be similar to procedures 1702 described above. For example, similar to steps 1801 and 1802 depicted in FIG. 17, the one or more processors may convert RGB values from each subsequent image 2102 into hue-saturation-value coordinates (HxSyV), and convert said coordinates into a probability map using the foreground histograms for colour and brightness. The one or more processors may estimate the location of tracker box 1102 based on the probability map.

For example, the one or more processors may apply a mean-shift process to the probability map of subsequent image to 2102 in order adjust the position of the tracker-box 1102 based a peak value of the probability map. A peak value nearest to the initial location of first tracker box 1102 may be used to locate box 1102, as shown in FIG. 21, in which said peak value is located in subsequent image 2102 at an edge of the foot pixels. In procedures 2201, the one or more processors may centre first tracker box 1101 on the nearest peak value, and calculate a first moment of the probabilities within first tracker box 1101. Procedures 2201 may be iterative. For example, procedures 2201 may be implemented as a "hill climbing" approach that iteratively locates the nearest peak value based on the probabilities, centres box 1101 on the located peak value, calculates the first moment of the probabilities in box 1101, locates a new peak value based on the first moments, centres box 1101 on the new peak value, and so on.

A one-dimensional slice of a probability distribution for the initial image 2101 of FIG. 21 is shown at 2201 in FIG. 22. The depicted slice plots probability 2202 against position 2203. In this one-dimensional slice, the first tracker box 1102 shown in image 2101 of FIG. 21 may be initially located at a first position 2204 based the positions 2203 of a range of probabilities 2202. As shown in FIG. 22, the probabilities 2202 may define one or more peak likelihood values, and box 1102 may be centred on the position 2203 associated with the one or more peak values.

A similar one-dimensional slice of subsequent image 2102 of FIG. 21 is shown at 2205 in FIG. 22. As shown, during the sweeping motion, the peak likelihood values of probabilities 2202 may move along the positive x-axis direction (e.g., to the right along the position 2203 axis in FIG. 22) from time (t) to time (t+1). Procedures 2201 may be used to iteratively by the one or more processors to move box 1102. For example, on a first iteration of the mean-shift process, first tracker box 1102 may be been moved to a position 2206 based on the nearest peak value; on a second iteration, the tracker box 1102 may be moved to a position 2207 based on a new peak value; and on a third iteration, the box 1102 may be moved to a final position 2208 based a final peak value.

After performing the operation illustrated in FIG. 22 to locate a new position for first tracker box 1102, the one or more processors may perform a smoothing operation to reduce jitter and/or reduce the risk of tracker box 1102 wandering off onto background distractors. For example, the new position of box 1102 may be first-order low-pass-filtered over time and constrained to lie within a predetermined distance from the image centre.

Aspects of an exemplary smoothing operation are now described. In some aspects, a new tracking location x'(t) may be calculated by the one or more processors; and an actual new location x(t) may be determined by the one or more processors from calculated value x'(t) and a previous actual position x(t−1). According to this aspect, the smoothing operation may therefore be specified as:

$$x(t)=a*x'(t)+(1-a)*x(t-1)$$

Where "a" is a number between zero and unity. Then, if:

$$D(x(t),(W/2,H/2))>T\text{dist}$$

The tracker location is retained at its previous value of x(t), such that:

$$x(t)=x(t-1)$$

In which, D(p1, p2) is the straight line (Euclidean) distance between two points; W and H are the dimensions of the input image pixels; and Tdist is a predetermined distance threshold in pixels. Accordingly, if a calculated movement is greater than the predetermined distance threshold, then the one or more processors may ignore the calculated movement as noise, and consider the next sample image.

In some aspects, a scaled down bit-map version of the data may be used to speed up the computations and/or reduce processing power requirements. Once processed, the tracking results may be scaled up by the one or more processors to match the coordinates of the original image.

FIG. 23

As described above, various predetermined motions of apparatus 305 may be used to obtain captured images based on video feed 601; and one such predetermined motion for apparatus 305 may be a sweeping motion, which may include a partial sweep and/or a full sweep. Aspects of an exemplary sweeping motion are illustrated in FIG. 23, in which apparatus 305 has been located at a start position of the sweeping motion. As shown, apparatus 305 may be located substantially to the right of the recipient at the start location; and the recipient may perform the sweeping motion by: holding apparatus 305 with an outstretched arm at the start location; orienting camera 403 of apparatus 305 towards a pair of feet and a scaling object; and rotating apparatus 403 around the pair of feet and the scaling object in a right-to-left direction from the start position.

The sweeping motion may be continuous or segmented. For example, the recipient may perform a manual-input gesture (e.g., by activating capture button 602 of FIG. 6) at the start position (e.g., while holding apparatus 305 towards one side, such as the right side depicted in FIG. 23). In keeping with procedures 500 described above (FIG. 5), the one or more processors may detect the manual-input gesture at the start position; and capture images and store image data at regular intervals during the sweeping motion that follows. If the one or more processors are able to store sufficient image data during the sweeping motion, then a single sweeping motion may be sufficient. Alternatively, the one or more processors may identify intervals of the sweeping motion where the processors were unable to store sufficient image data, and prompt the recipient to return to the rotational positions associated with those intervals. For example, the processors may prompt the recipient to perform additional predetermined motions (e.g., one or more partial or full sweeps), and/or repeat aspects of procedures 500 (FIG. 5) during each additional motion until a sufficient amount of image data has been stored.

To facilitate the subsequent processing of image data, and reduce the processing power requirements, the recipient may stand on or adjacent a feature-less background. As shown in FIG. 23, for example, the recipient may be stand in front of a white sheet of paper 2301. As also shown, a scaling object 2302 may be located near paper 2301. Scaling object 2302 may be any object of a known size. As shown in FIG. 23, object 2302 may be approximately the same size as a credit card, and located at a mid-position along a near long edge 2303 of the paper 2302.

Processing requirements may be reduced by making at least one aspect of captured images similar, such as focal length. For example, the recipient may rotate apparatus 305 around the pair of feet and scaling object 2302 in the right-to-left direction with the outstretched arm so as to maintain a similar distance between camera 403 and the pair of feet and the scaling object 2302 during the sweeping motion.

FIG. 24

Figure 24:
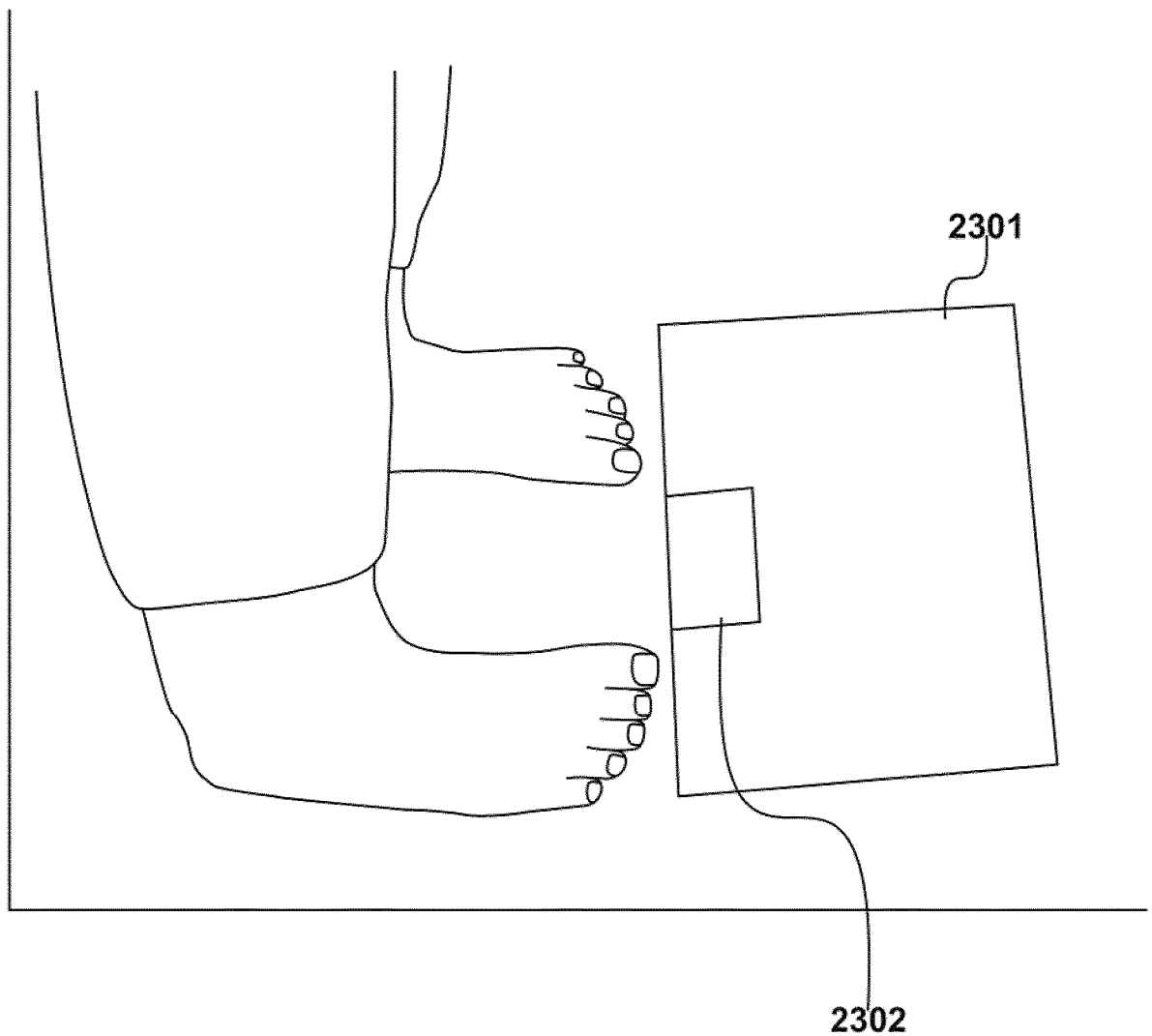
FIG. 24 illustrates an example of an image.

An exemplary captured image is illustrated in FIG. 24. As shown, the image may be captured with the one or more processors based on video feed 601 at the start position of the sweeping motion depicted in FIG. 23. As described herein, the one or more processors may capture the image, and store image data including a two-dimensional pixel array associated with the said position. In this example, the recorded image includes the feet of the recipient, sheet of paper 2301, and scaling object 2302.

FIG. 25

The recipient may continue to perform the rotational sweep by continuing to rotate the apparatus 305 around the pair of feet and scaling object 2302. For example, the recipient may continue to rotate apparatus 305 in the right-to-left direction from the start position depicted in FIG. 24 to one or more intermediate positions. As described herein, the one or more processors may determine rotational positions of apparatus 305 during the sweeping motion; capture images at intervals during the sweeping motion; and associate each captured image with one of the rotational positions. The intervals may be based on the sweeping motion. For example, each image may be captured after moving apparatus 305 through a partial sweep, which may be defined as a predetermined arc length representing a minimum change between two rotational positions.

Figure 25:
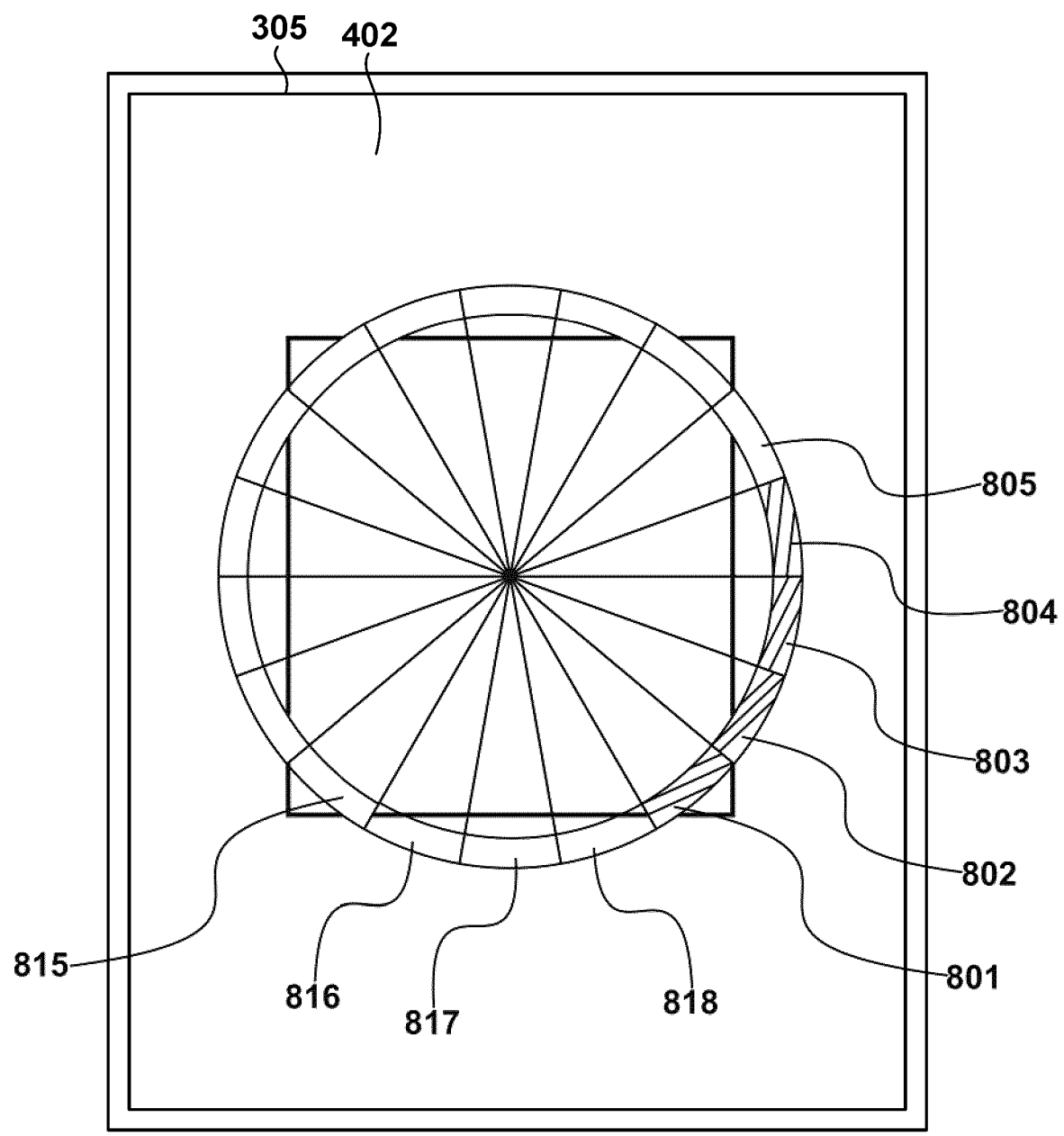
FIG. 25 shows an example of a graphical display.

As shown in FIG. 25, the one or more processors may guide aspects of the sweeping motion. Aspects of the compass rose shown in FIG. 8 may be used a guide. As described above, the compass rose may comprise a central capture area 830 surrounded by a rotational guide 840 including a plurality of circumferential markers 801 to 818. Each marker 801 to 818 may correspond with a different rotational position of apparatus 305. For example, the one or more processors may capture images while apparatus 305 is being rotated in the right-to-left direction from the start position of FIG. 24; associate each captured image with a rotational position corresponding with one of markers 801 to 818; and modify said markers to indicate that a captured image has been associated therewith.

As shown in FIG. 25, each marker 801 to 804 may have been changed when associated with one of the capture images. Any type of visual change may be used. For example, each of markers 801 to 818 may have a pre-association colour (e.g., red) that may be changed to a post-association colour (e.g., green) when associated with an image.

FIG. 26

An exemplary intermediate position of the sweeping motion is depicted in FIG. 26. As shown, the recipient may continue to rotate apparatus 305 in the right-to-left direction from the start position of FIG. 23 to the intermediate position of FIG. 26, in which apparatus 305 is located substantially in front of the user.

FIG. 27

Figure 27:
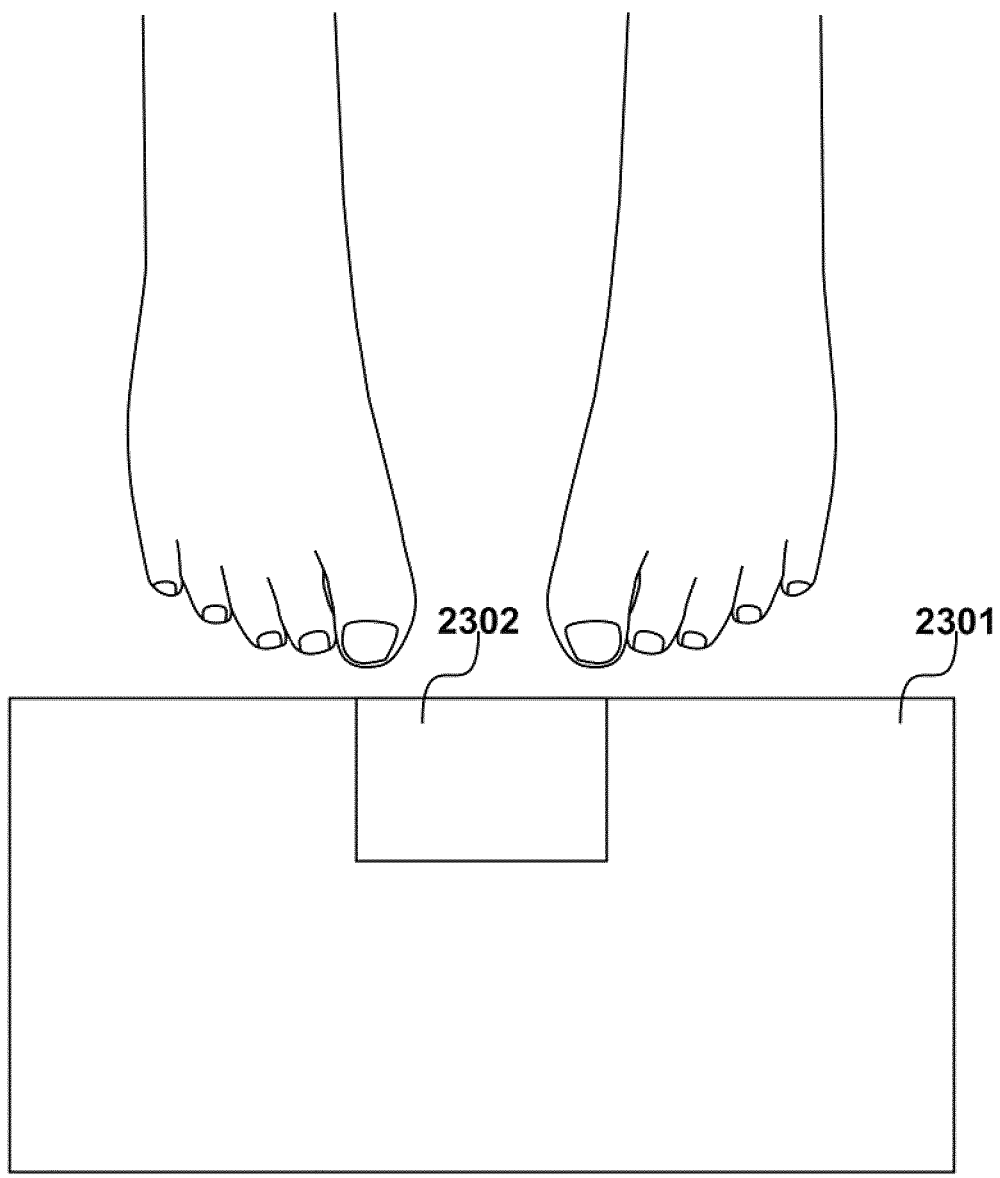
FIG. 27 shows an example of an image captured at the tracking instant of FIG. 26.

Another exemplary captured image is illustrated in FIG. 27. As shown, the image may be captured with the one or more processors based on video feed 601 at the intermediate position of FIG. 26. As before, the recorded image may include the feet, the sheet of paper 2301, and the scaling object 2302. Although not required, the recipient's feet may remain at a fixed position relative to paper 2301 and/or object 2302 during the sweeping motion. For example, the position of the feet at the start position of FIG. 23 may be substantially the same as the position of the feet at the intermediate position of FIG. 27, making it easier for the one or more processors to accurately compute differences between the captured images associated with the respective start and intermediate positions.

FIG. 28

Figure 28:
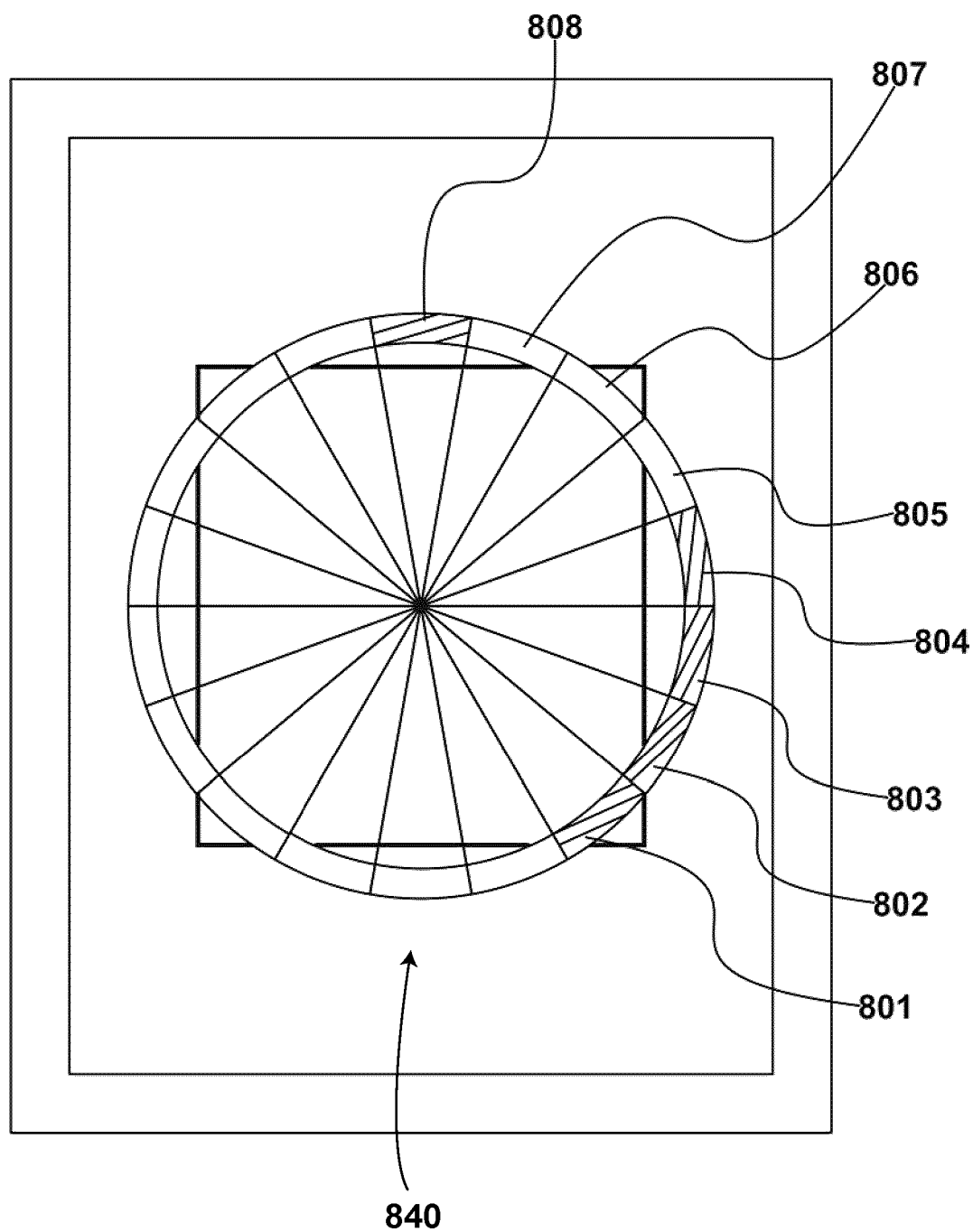
FIG. 28 shows an updated example of the graphical display of FIG. 25.

Aspects of the sweeping motion may cause errors. For example, the recipient may move apparatus 305 at a rate that prevents the one or more processors from performing some the functions described herein. An example is illustrated in FIG. 28. For the purposes of this illustration, it may be assumed that the recipient has moved apparatus 305 in the right-to-left direction from the initial position of FIG. 23 to the intermediate position of FIG. 26 at a rate that prevents the one or more processors from obtaining the captured images and/or associating said images with a position.

The aforementioned compass rose may be used to communicate and/or correct these errors. As shown in FIG. 28, for example, the one or more processors may modify the rotational guide 840 to communicate that captured images have associated with the locations corresponding with markers 801 to 804 and 808 (e.g., by changing their colour from red to green); but not with locations corresponding with markers 805 to 807 (e.g., by leaving their colour red). The one or more processors may communicate the errors using visual and/or non-visual notifications. For example, if some of the rotational positions have been missed, the one or more processors may be operable with speaker 407 and/or vibrator 408 to generate a buzzing alarm, and/or escalate said alarm to a buzzing sound in combination with a vibration. Either of these non-visual notifications may be used to communicate that markers 805 to 807 have been missed, and/or encourage the user to retrace at least that portion of the sweeping motion.

Any combination of visual and non-visual notifications may be used to communicate such errors. For example, the one or more processors may generate any type of graphical alert (e.g., by further modifying the compass rose); and/or any type of sound or set of sounds (e.g., by operating speaker 407 and/or vibrator 408). In some aspects, the visual and/or non-visual notifications may alert the recipient to markers around the recipient's feet where additional images of the feet are needed for processing because they have been missed during the sweeping motion and/or otherwise have not been captured by apparatus 305.

FIG. 29

Figure 29:
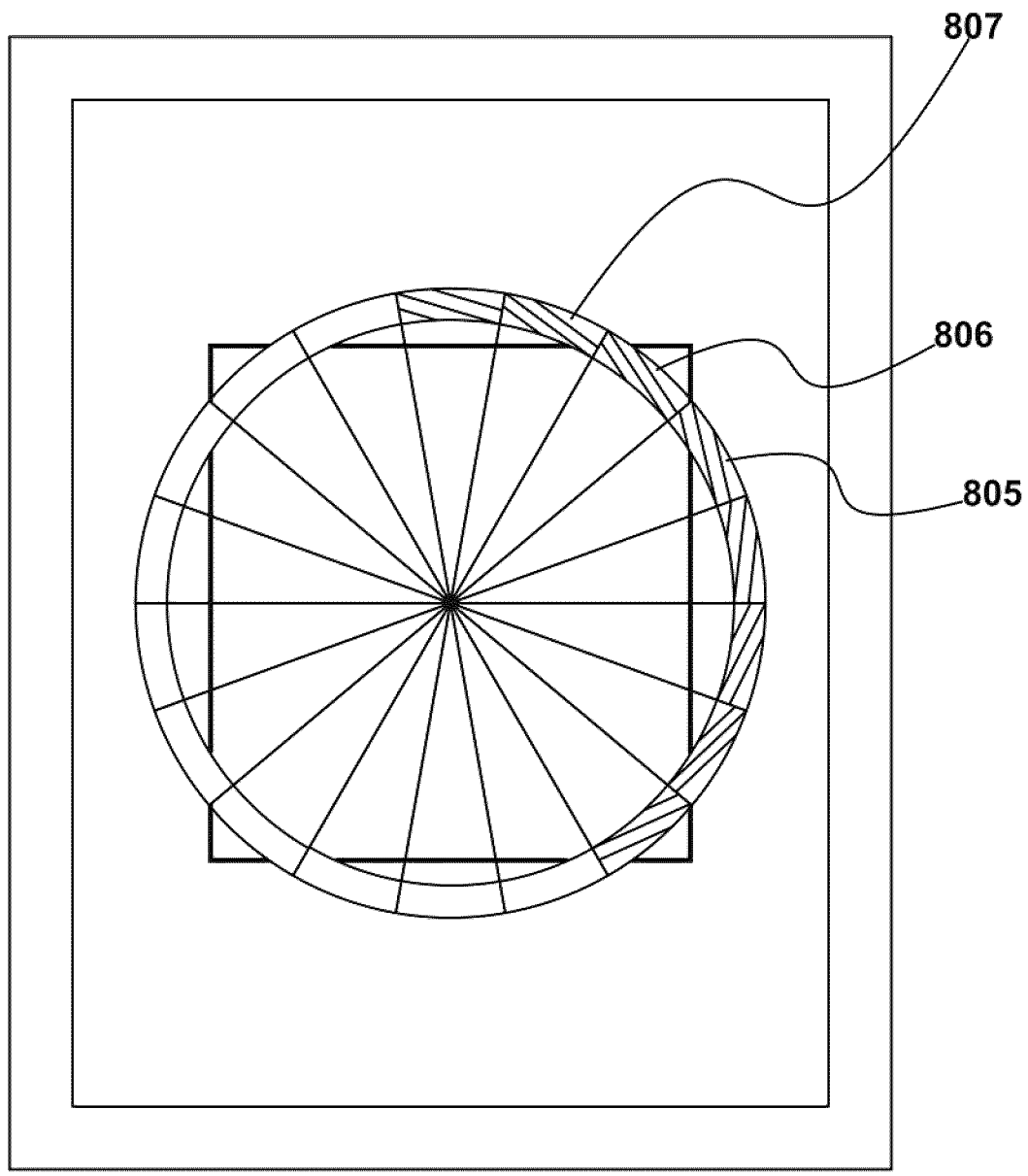
FIG. 29 shows a further updated example of the graphical display of FIG. 25.

An exemplary error correction is depicted in FIG. 29. As shown, the one or more processors may determine that markers 805 to 807 have not been associated with captured images, and generate visual and/or non-visual notifications to communicate the error to the recipient. As above, the notification may be include a buzzing, a vibration, and/or another form of alert generated by operating speaker 407, vibrator 408, and/or other notification device in communication with the one or more processors.

The one or more processors may prompt the recipient to retrace all or a portion of the sweeping motion using visual and/or non-visual notifications. For example, processor 401 may modify aspects of markers 805 to 807 in order to prompt the recipient to repeat portions of the sweeping motion associated therewith. Exemplary visual modifications may include colour changes (e.g., changing each market 805 to 807 from red to yellow), timing changes (e.g., blinking the colour of each marker 805 to 807), and/or sequence changes (e.g., blinking each marker 805 to 807 in sequence that corresponds with the rotational direction of the sweeping motion); and exemplary non-visual notifications may include any sound and/or vibrations generated by processor 401 for like effect.

Consequently, if the recipient follows the visual and/or non-visual prompts, then markers 805 to 807 may be associated with captured images, correcting the aforementioned errors, if they arise. As shown in FIG. 29, once these errors are corrected, the one or more processors may change the colour of each marker 805 to 807 from a pre-association colour (e.g., red) to a post-association colour (e.g., green).

FIG. 30

An exemplary final position of the sweeping motion is depicted in FIG. 26. As shown, the recipient may continue to rotate apparatus 305 in the right-to-left direction from the intermediate position of FIG. 26 to the final position of FIG. 30, in which apparatus 305 is located substantially to the right of the recipient. Additional images may be captured based on video feed 601 during this portion of the sweeping motion.

While described as a final position, the position depicted in FIG. 30 may or may not be final. For example, to extend the sweep further, the recipient may: move the apparatus 305 to the other outstretched arm at the final position; re-orient camera 403 towards the pair of feet and the scaling object 2302; and continue rotating apparatus 305 in the right-to-left direction around the pair of feet and the scaling object 2302 with the other outstretched arm. Although not required, these additional steps may be used to capture images based on video feed 601 during a full, three-hundred-and-sixty degree sweeping motion.

FIG. 31

Figure 31:
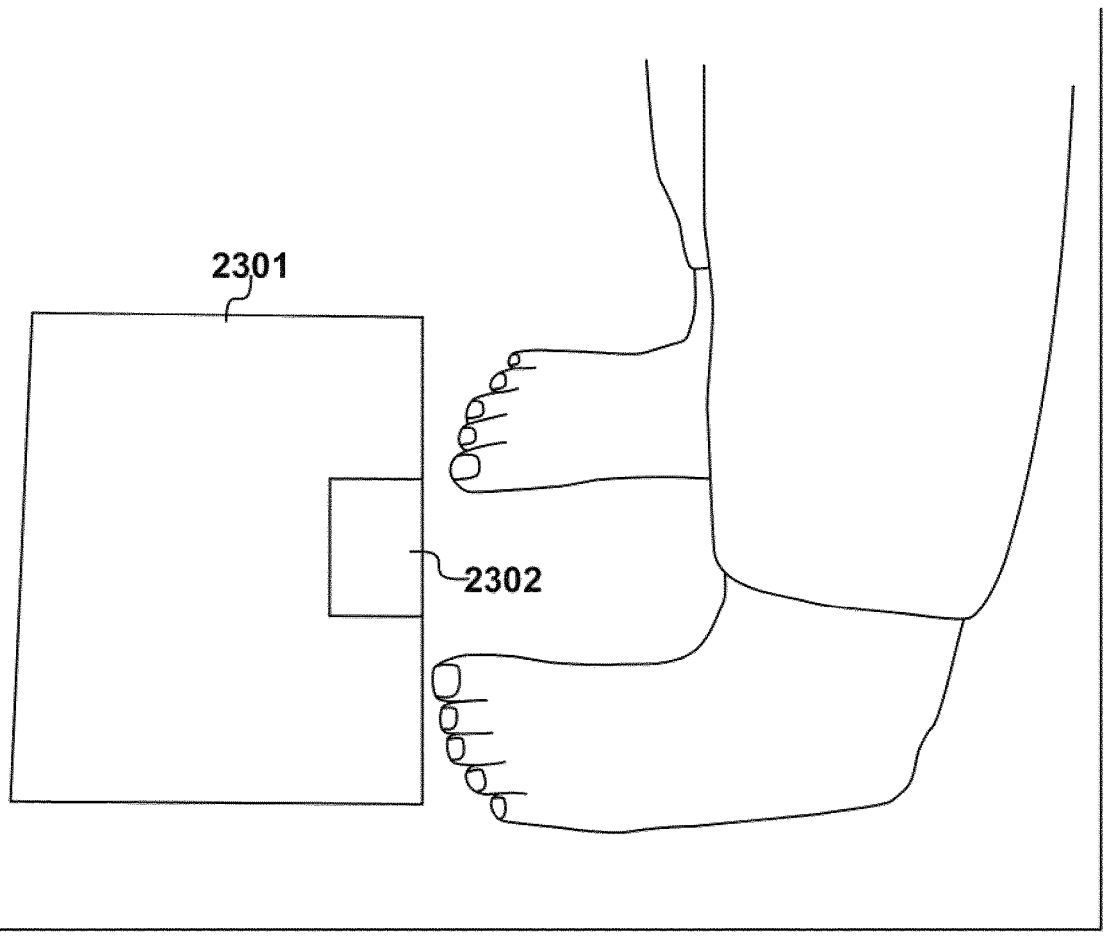
FIG. 31 shows an example of an image captured at the instant of FIG. 30.

Another exemplary captured image is illustrated in FIG. 31. As shown, the image may be captured based on video feed 601 at the final position of FIG. 30. As before, the recorded image may include the feet, the sheet of paper 2301, and the scaling object 2302. Accordingly having followed the procedures describe above, each captured image may include images of the recipient's feet, the paper 2301, and the scaling card 2302 taken from a plurality of different positions. In some aspects, at least three different positions may be used, including at least the start position of FIG. 23, the intermediate position of FIG. 26, and the final position of FIG. 30.

FIG. 32

Figure 32:
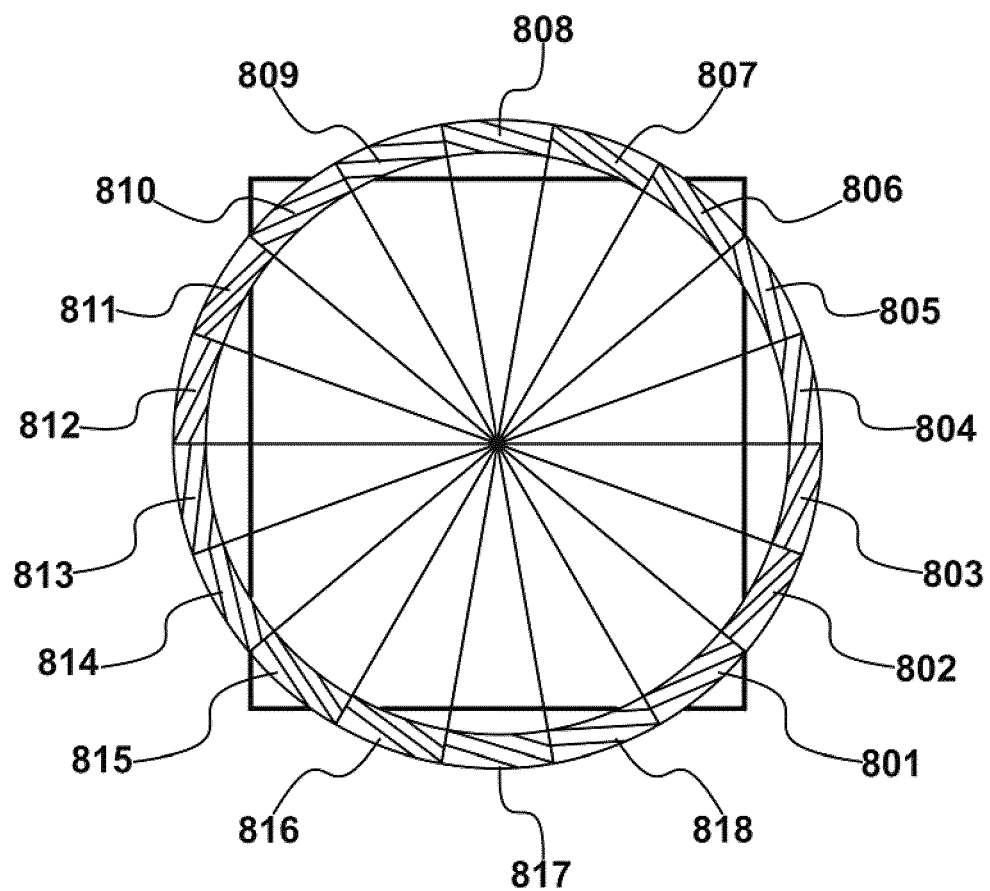
FIG. 32 shows a fully updated example of the graphical display of FIG. 25.

As illustrated in FIG. 32, the one or more processors may confirm that the sweeping motion has been completed successfully. Aspects of the aforementioned compass rose may be used to communicate the confirmation. For example, once captured images have been associated with markers 801 to 818, the one or more processors may change the colour of each marker 801 to 818 from a pre-association colour (e.g., red) to a post-association colour (e.g., green); or from the post-association colour (e.g., green), to a confirmation colour (e.g., blue). In some aspects, the one or more processors may be further operable with speaker 407 and/or vibrator 408 to generate a non-visual notification of the confirmation, such as a beeping and/or buzzing sound. In other aspects, the notification of confirmation may comprise a message displayed visually with display device 402 and/or non-visually with speaker 407 and/or vibrator 408.

FIG. 33

Figure 33:
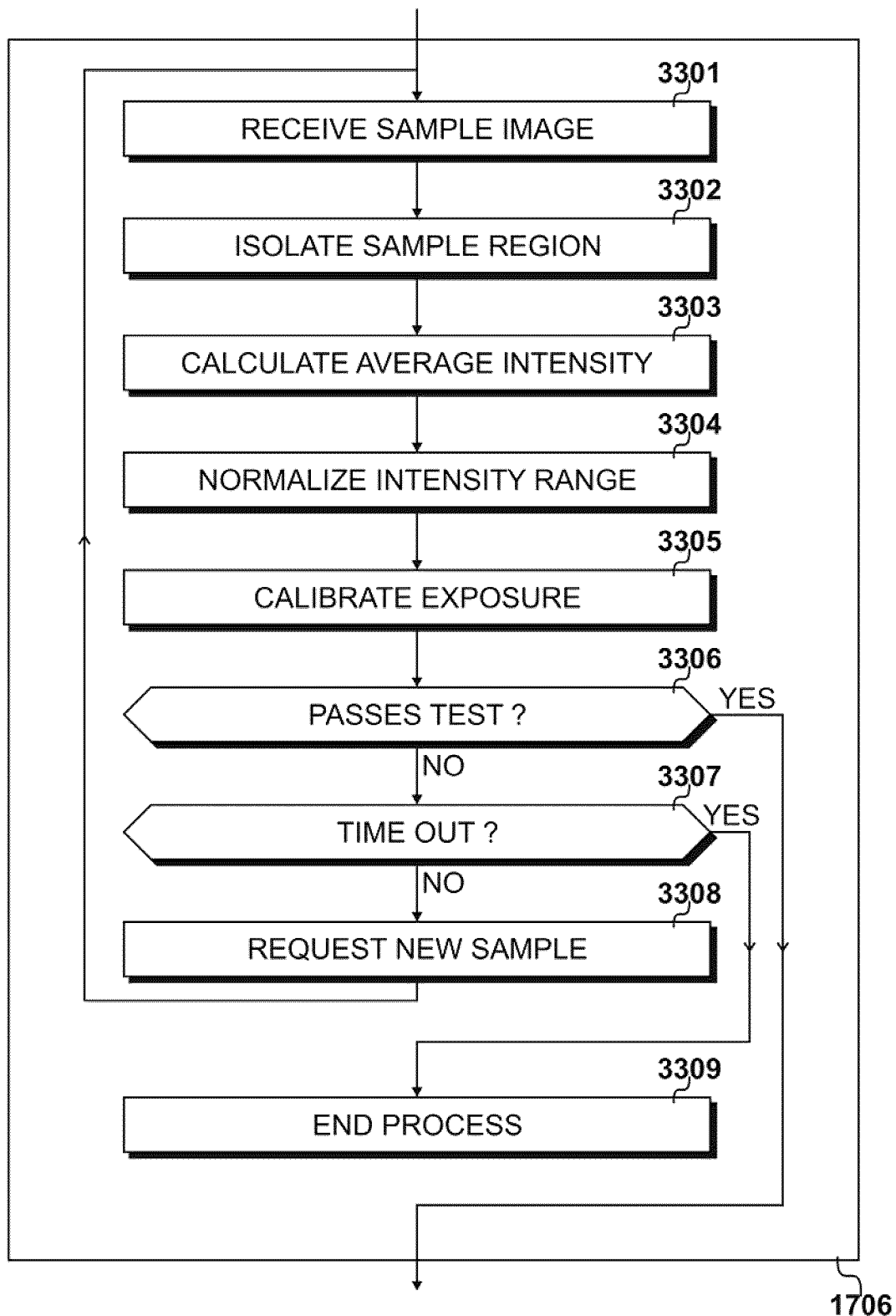
FIG. 33 details exemplary procedures for optimizing settings for the image capturing process identified in FIG. 17.

Exemplary procedures 1706 (FIG. 17) for optimizing settings of the image capturing process are detailed in FIG. 33.

At step 3301, a sample image from video feed 601 may be received at the one or more processors. For example, as described above, the one or more processors may select the sample image from video feed 601. At step 3302, a sample region of the sample image may be isolated. For example, the sample region may be defined by first tracker box 1102, and the one or more processors may isolate the sample region by excluding the pixels outside of box 1102 from procedures 1706.

At step 3303, an average pixel intensity value may be calculated for the pixels contained in the sample region. Apparatus 305 and/or camera 403 may generate colour images. Each colour image may be constructed from components of red, green, and blue; and intended to be as life-like as possible. Accordingly, each pixel within each sample region may have corresponding RGB value; and the one or more processors may convert the RGB values into a range of intensity values using the exemplary colour space-conversion procedures described above. In this example, the one or more processors may calculate the average pixel intensity value based on the range of intensity values.

Non-colour based optimization procedures also may be used by the one or more processors because the captured images may not need to appeal to the human eye, and may not be printed or presented in any eye-readable forms. For example, the purpose of each captured image may be specific to processor 401, such as facilitating subsequent processing for making evaluations of foot size and shape, making the RGB values optional.

At step 3304, the intensity range calculated at step 3303 may be normalized by the one or more processors to enhance contrast within the sample region of the sample image. In this regard, procedures 1706 may use all or a substantial portion of the available intensity range supported by apparatus 305 for pixels derived from images of the feet. Additional optimization steps may be performed within procedures 1706 to support other aspects of this disclosure, such as the evaluation process 309 detailed in FIG. 3.

After normalizing the intensity range at step 3304, the one or more processors may calibrate apparatus 305 at step 3305. Example calibrations may include the focus, exposure, and/or white balance of camera 403. At step 3306, the processors may perform one or more calibration tests. Any testing methods may be used, such as estimating re-projection error. If the calibration tests performed at step 3306 are successful, then the one or more processors may obtain the captured images based on video feed 601, and store the captured images on memory device 404 as image data.

Alternatively, if calibration the tests performed at step 3306 are unsuccessful, then a new sample region may be selected, and steps 3302 to 3306 repeated with the new sample region.

A timeout test may be performed at step 3307 to limit the number of iterations performed by the one or more processors. Prior to timeout, either the one or more processors or the recipient may select the new sample region (e.g., based on second tracker box 1302). After timeout, the one or more processors may communicate one or more reasons why the calibration test was not successful and/or exit procedures 1706. For example, the one or more processors may prompt the user to modify a lighting condition and/or change the type of camera 403 before attempting procedures 1706 again.

FIG. 34

Figure 34:
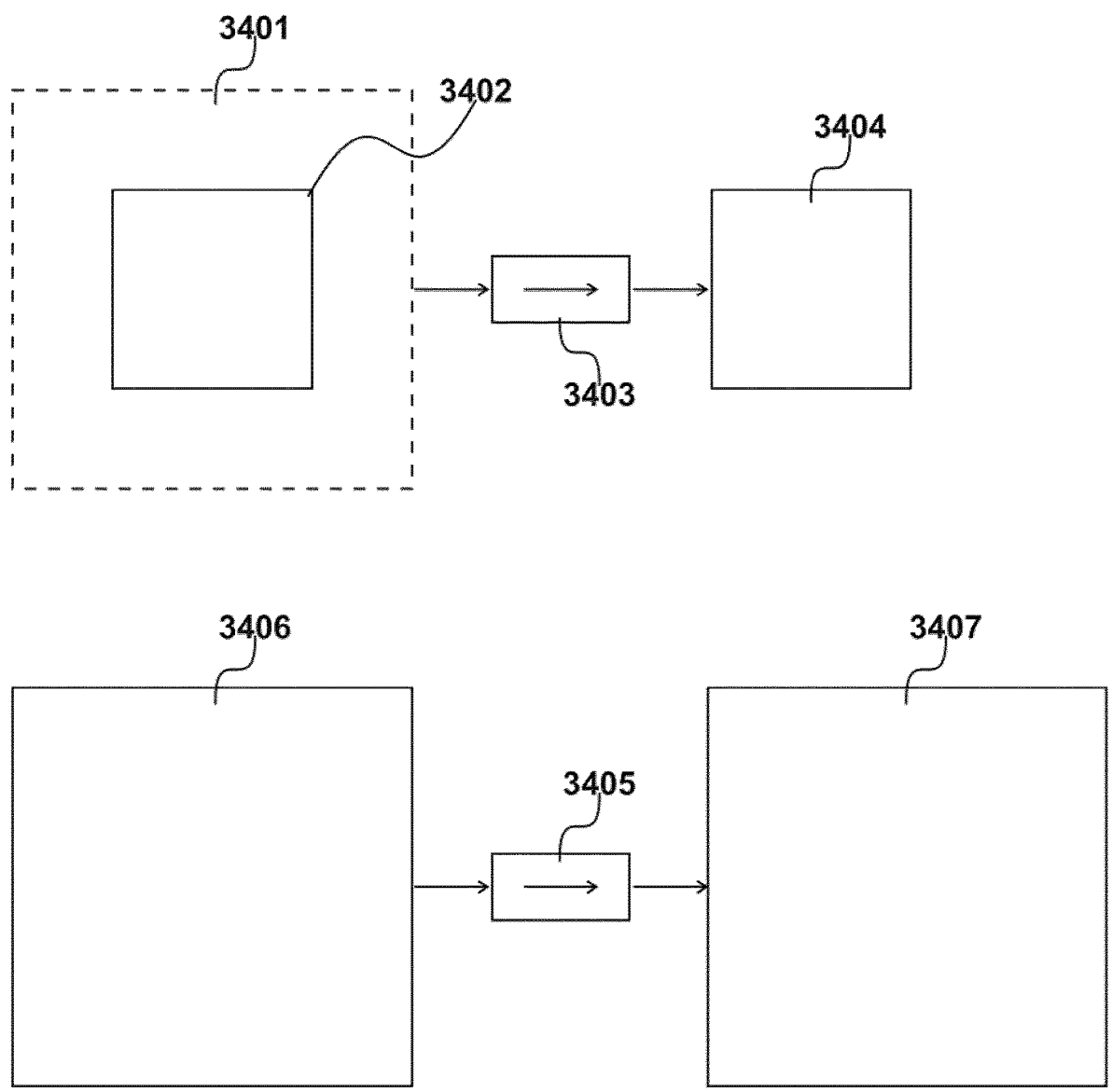
FIG. 34 shows an example of a sample image for normalisation.

Exemplary aspects of procedures 1706 (FIG. 17) are detailed in FIG. 34, which depicts an exemplary sample image 3401 having an exemplary sample region 3402. Sample image 3401 may be received by the one or more processors. For example, processor 401 may select image 3401 based on video feed 601 using procedures described herein. Sample region 3402 may include any interior region(s) of sample image 3401, such as the central interior region shown in FIG. 34.

In this example, the one or more processors may use a first normalization procedure 3403 to analyse pixel data within sample region 3402, and determine how a more optimized set of pixels (e.g., shown at 3404 in FIG. 34) may be produced by the one or more processors through a process including normalization. For example, the one or more processors may use the first procedure 3403 to derive a normalization function based on parameters of apparatus 305; and apply the normalization function to each captured image based on video feed 601. An exemplary captured image 3406 is depicted in FIG. 34. As shown, the one or more processors may use a second normalization procedure 3405 to apply the normalization function, transforming the captured image 3406 into a normalized captured image 3407.

FIG. 35

Figure 35:
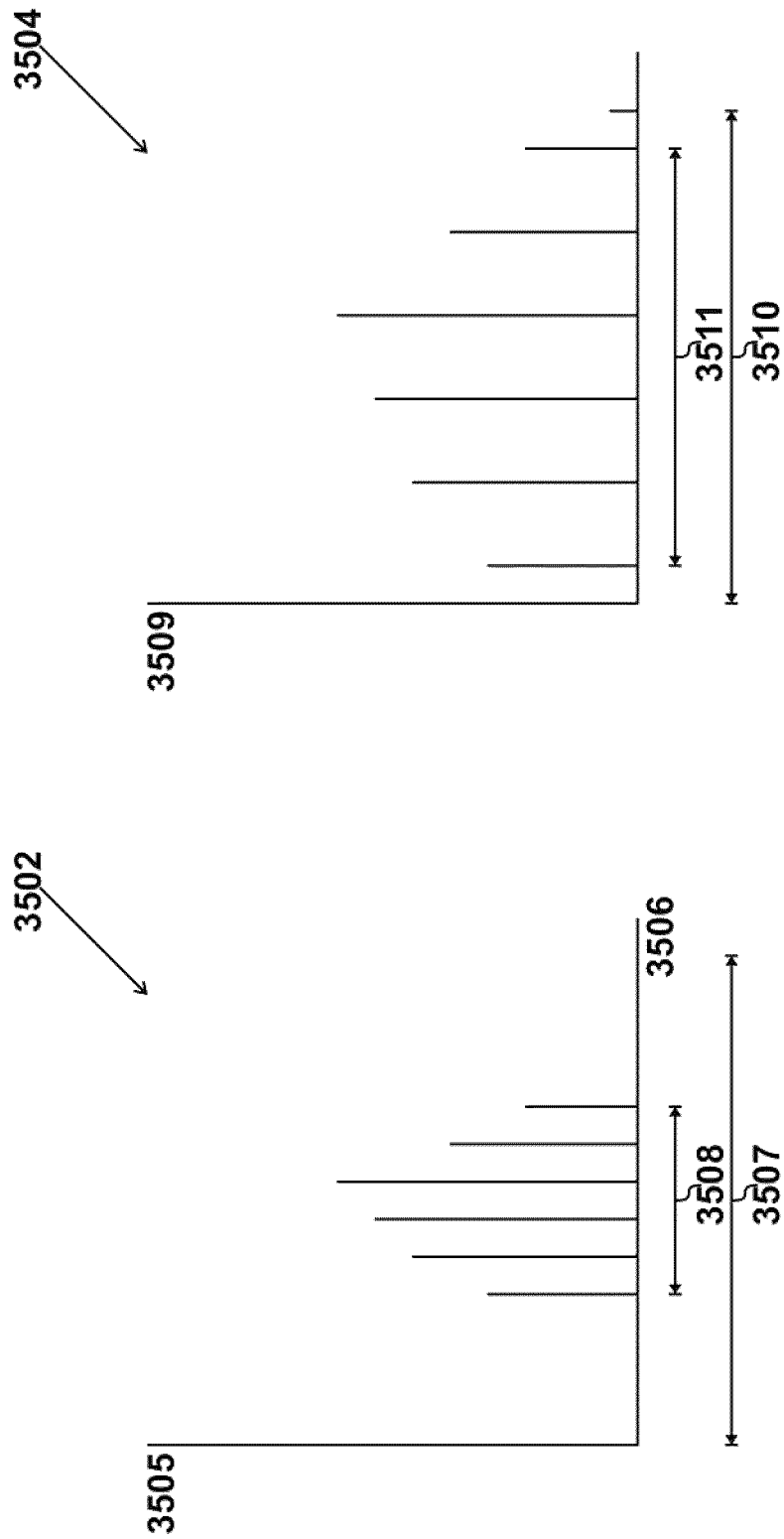
FIG. 35 shows an exemplary graphical representation of a normalisation process.

Exemplary aspects of normalization procedure 3405 (FIG. 34) are detailed in FIG. 35. A first graphical representation 3502 of exemplary pixel data for sample region 3402 is shown in FIG. 35 at left; and a second graphical representation 3504 of the same pixel data after being normalized by procedure 3405 is shown in FIG. 35 at right. The first graphical representation 3502 may plot frequency (e.g., number of occurrences) 3505 against pixel intensity 3506. The pixel intensity may have an available or possible dynamic range 3507. As shown in FIG. 35, only a portion 3508 of the available or possible dynamic range 3507 may be used in some aspects.

Exemplary aspects of procedure 3403 of FIG. 34 are illustrated by second graphical representation 3504 of FIG. 35. As shown, the frequency of occurrences 3509 may remain the same, given that the total number of pixels within sample area 3401 may remain constant. The one or more processors may use normalization procedure 3403 to adjust aspects of pixel intensity 3506. For example, as shown in the second graphical representation 3504, the values of pixel intensity 3506 may be adjusted by the one or more processors in normalisation procedure 3403 so that, from an available or possible dynamic range of 3510, a second portion 3511 may be used, the second portion 3511 being larger than the above-reference first portion 3508 of dynamic range 1507.

FIG. 36

Figure 36:
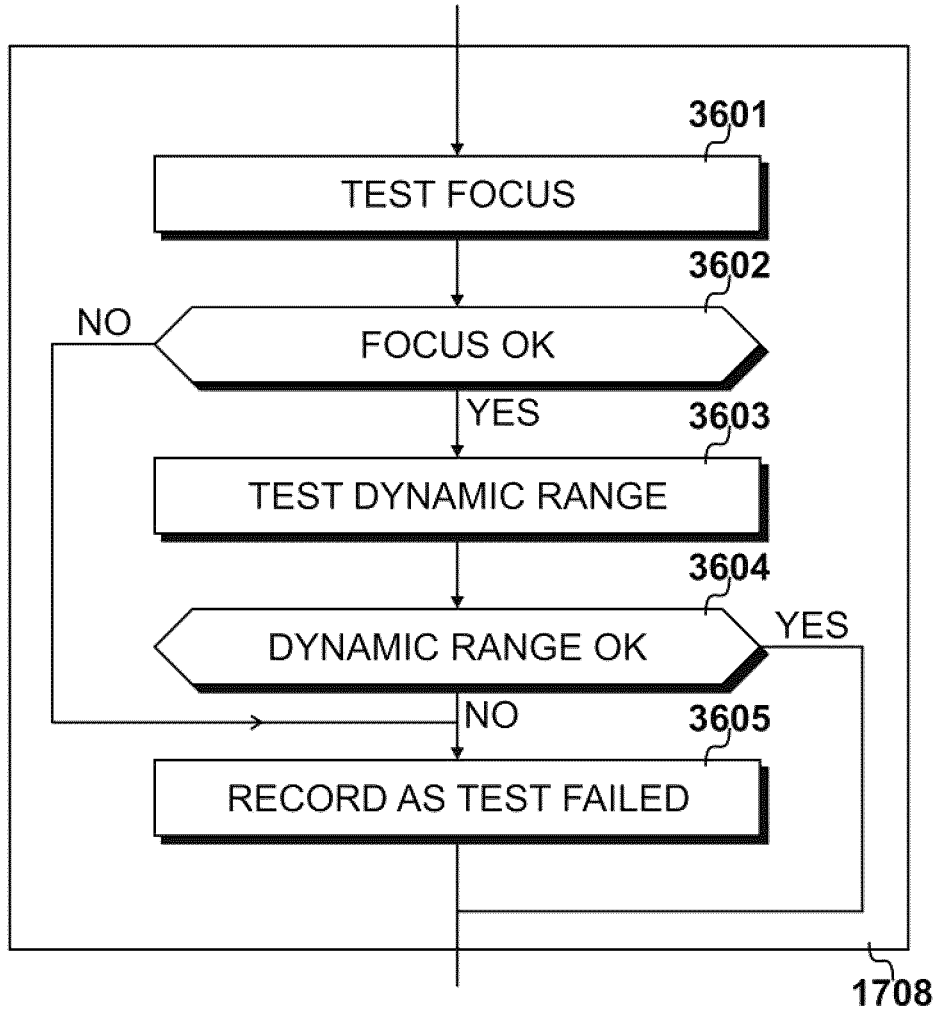
FIG. 36 shows exemplary procedures for testing the quality of images.

Exemplary aspects of procedures 1708 (FIG. 17) for testing the quality of each captured image are detailed in FIG. 36. As described above in previous examples, aspects of first tracker box (e.g., FIG. 11) may be tracked by the one or more processors while apparatus 305 is being moved in a predetermined motion by the recipient, such as the sweeping motion described above. The tracked aspects may include rotational positions of apparatus 305 within the sweeping motion.

In some aspects, the rotational positions of apparatus 305 may be based on position data from IMU 409. For example, IMU 409 may track the rotational position of apparatus 305 relative to a start position of the sweeping motion, and output position data including the rotational positions to the one or more processors during the sweeping motion. Accordingly, the one or more processors may receive the position data, and perform various functions described herein based on the position data. For example, after a predetermined extent of the sweep has occurred (e.g., approximately ten (10) degrees of rotational movement), processor 401 may respond by interrupting any of the above-described processes for capturing images and/or storing image data.

The one or more processors may control aspects of apparatus 305 during testing procedures 1708. For example, the one or more processors may by operable to focus a lens system of camera 403, and/or maintain that focus to constrain the operation of apparatus 305. In this example, once apparatus 305 has been constrained, the one or more processors may achieve optimized focusing of the pixels to identify image pixels derived from the skin of the foot. As a further example, the processors also may adjust apparatus 305 to make better use of the available or possible dynamic range.

Exemplary testing steps 3601 to 3605 are shown in FIG. 36 and now described. At step 3601, for example, the one or more processors may determine test characteristics of a captured image; and, at step 3602, the one or more processors may determine to whether the test characteristics are acceptable. The test characteristics may be based on dynamic range, focus, and the like; and the one or more processors may test each captured image on this basis. For example, as shown in FIG. 36, if the one or more processors may determine at step 3602 that the focus of a captured image is not acceptable; identify at step 3605 the testing procedure 1708 as failed; and answer the question asked at step 1709 of procedures 503 (FIG. 17) in the negative.

The dynamic range may be tested based on optimization indicators, which may include any comparative measures of first dynamic range 3507, first portion 3508, second dynamic range 3510, and/or second portion 3511 described above. For example, the one or more processors may determine that the dynamic range of the capture image is acceptable (e.g., like second range 3511 of FIG. 35), or unacceptable (e.g., like first range 3508 of FIG. 35). Therefore, as before, if the one or more processors determine that the dynamic range of a captured image is not acceptable, then testing procedure 1708 of FIG. 36 may be identified as failed at step 3605; allowing the question asked at step 1709 of procedures 503 (FIG. 17) to be answered in the negative.

Other test characteristics may be based on movement indicators, which may include visual indicia of movement (e.g., blurring and/or trailing), and/or non-visual indicia of movement (e.g., position data from IMU 409). For example, if the processors determine that the movement indicators are not acceptable, then testing procedure 1708 of FIG. 36 is identified as failed at step 3605; allowing the question asked at step 1709 of procedures 503 (FIG. 17) to be answered in the negative. The presence of any movement indicators may be a basis for rejection. For example, the processors may reject a captured image as unacceptable if any movement indicators are detected, and/or if the position data indicates that apparatus 305 was moving incorrectly. For example, blurring may be present if too much movement has occurred, such as when apparatus 305 is being moved too quickly through the sweeping motion when capturing an image. Accordingly, the one or more processors may measure the blurring and/or the movement speed, and reject the captured image based on the measurement.

FIG. 37

Exemplary aspects of procedures 505 (FIG. 17) for storing the captured images are now described. In some aspects, procedures 505 may comprise additional processing steps, such as uploading the image data from apparatus 305 to foot evaluation process 309.

As described above, each captured image may be stored as image data on storage device 405 in step 503 of procedures 500 (e.g., FIG. 5) after performance of various optimization and testing procedures (e.g., FIG. 17). At step 3701 of procedures 505 (FIG. 37), the image data including each captured image may read by the one or more processors from storage device 405. In some aspects, at step 3702, the one or more processors may read position data corresponding with the image data. For example, IMU 409 may generate position data for each captured image, and the one or more processors may store the position data on storage device 405 together with a link to the corresponding image data. At step 3702, the one or more processors may identify the position data based on the link.

At step 3703, the one or more processors may assemble the image data and the position data into a data file. Procedures 505 may be repeated for each capture image. For example, at step 3704, the one or more processors may determine whether data for another captured image is to be considered as part of the data file. When answered in the affirmative, the one or more processors may return to step 3701 for the next captured image.

Eventually, the one or more processors will be able to answer the question asked at step 3704 in the negative. For example, the one or more processors may use a counter to reduce the processing requirements of the one or more processors by limiting the number of captured images to a predetermined maximum, which may be include at least three captured images. Once all of data files have been assembled, at step 3705, the one or more processors may combine the assembled data files with metadata into a combined data file. For example, aspects of the metadata may identify the recipient to whom footwear is to be allocated and/or include data representing the recipient's preferences, along with time and date stamps to identify when each captured image was recorded. In some aspects, after performance of step 3705, the combined data file may include all the data required for performance of the foot evaluation process 309.

Additional steps may be performed by the one or more processors to prepare the combined data file. For example, at step 3706, the one or more processors may compress the combined data file. In some aspects, the image data may be compressed in accordance with JPEG recommendations, although any known compression procedures may be deployed. Compression may be desirable in some aspects to reduce transmission times. In other aspects, lossless compression may be preferred. If a degree of loss is acceptable or necessary, then the one or more processors may test the spatial definition and integrity of each captured image (e.g., in testing procedures 1708 of FIG. 36), and only process the captured images having sufficient spatial definition and integrity.

At step 3707, after compressing the combined data file, the one or more processors may establish an uplink (e.g., an internet connection) to foot evaluation process 309 (FIG. 3). At step 3708, the one or more processors may upload the compressed combined data file to process 309.

In general, the procedures detailed in FIGS. 1 to 37 may provide various means for capturing images based on video feed 601; processing aspects of the captured images; and uploading the processed images for further consideration.

As described above, each processed image may include images of feet that have been recorded by the one or more processors as image data suitable for remotely deriving foot-related evaluations within foot evaluation process 309. The one or more processors may record the image data together with position data using the procedures 505 depicted in FIG. 37. In some aspects, the images may be recorded at different relative positions around the recipient's feet, and stored as image data together with position data corresponding with the different relative positions. The position data may be determined by the one or more processors and/or IMU 409. For example, each different relative position may correspond with a different rotational position of apparatus 305 during the sweeping motion, and the position data may be either: determined by the one or more processors based on a sequence of the rotational positions within the sweeping motion; and/or output from IMU 409 based on a location of apparatus 305 relative to a start position of the sweeping motion.

As also described above, the data files assembled for the captured images in steps 3701 to 3704 may be combined with metadata at step 3705, compressed at 3706, and uploaded to one or more processor at step 3708, such that, when received at said one or more processors, position data for each captured image may be known.

FIG. 38

Exemplary aspects of processing the combined data files output from procedures 505 are now described. As described above, one or more processors may perform foot evaluation process 309 and/or recommendation process 310 (e.g., FIG. 3). The processors may be in communication with one another (e.g., over an internet connection), and may include processor 401, which may use the additional processing power to perform aspects of evaluation process 309 and/or recommendation process 310. In other aspects, processor 401 may have enough processing power to perform all of processes 309 and 310.

Figure 37:
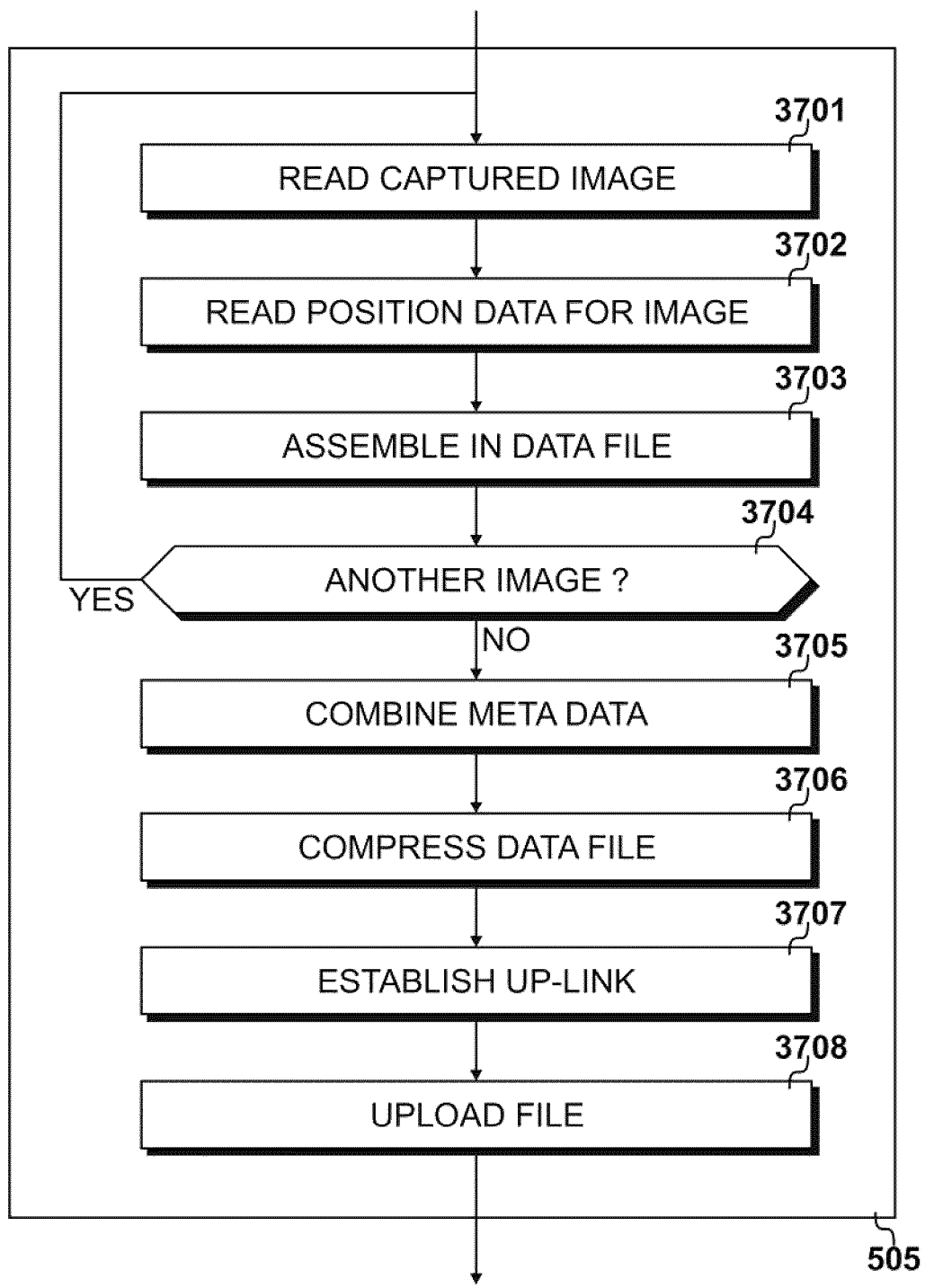
FIG. 37 details exemplary procedures for processing and uploading image data.
Figure 38:
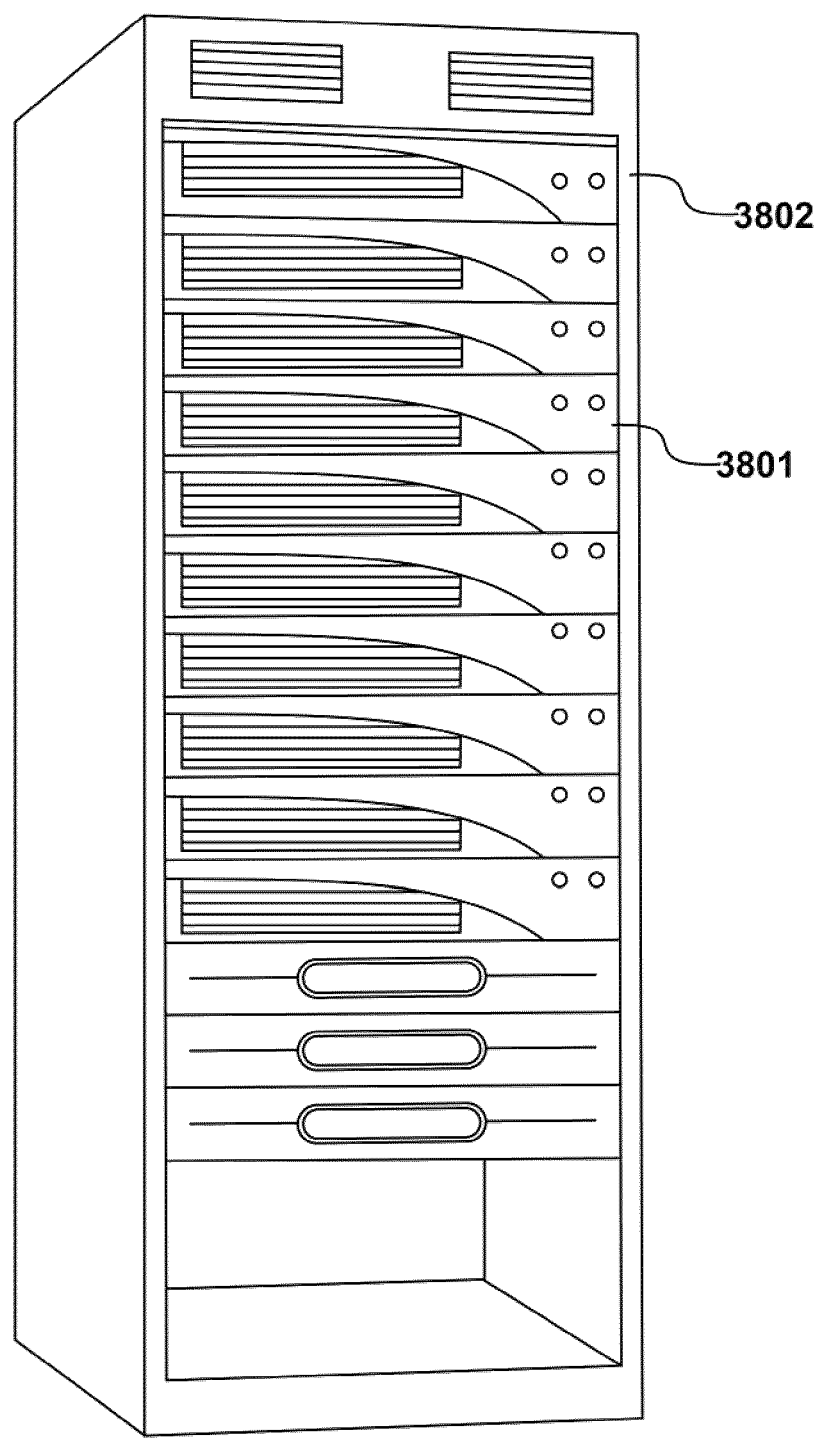
FIG. 38 shows an example of a processing environment for implementing the recommendation process identified in FIG. 3.

Another example of the one or more processors is shown in FIG. 38 as a processing device 3801. As shown, processing device 3801 may receive the compressed combined data files uploaded from the one or more processors at step 3708 of procedures 505 (e.g., FIG. 37). In FIG. 38, the processing device 3801 is retained within an optional rack 3802 that may be arranged to hold similar computing devices and/or provide an internet connection. In some aspects, a plurality of processing devices 3801 may be retained in rack 3802, and configured to perform similar or unrelated tasks in support of evaluation process 309 and/or recommendation process 310. In other aspects, processing device 3801 may be replaced with a server or other computing device having sufficient processing capacity to carry out the processes 309 and/or 310; or a combination of such devices, which may or may not include rack 3802.

FIG. 39

Figure 39:
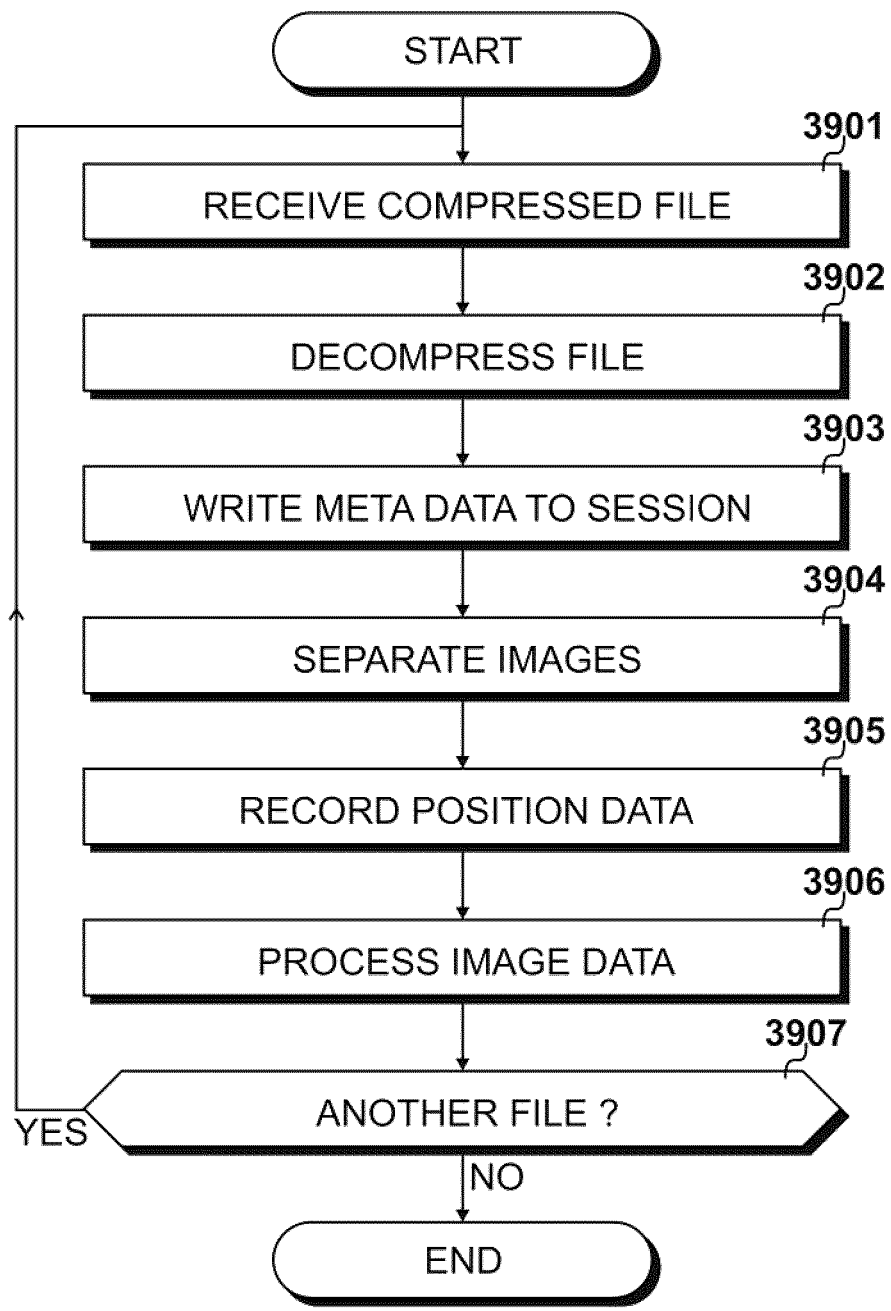
FIG. 39 details exemplary procedures for the recommendation process identified in FIG. 3.

Exemplary aspects of recommendation process 310 (e.g., FIG. 3) are detailed in FIG. 39.

At step 3901, the one or more processors may receive the compressed combined data files uploaded at step 3708 of procedures 505 (e.g., FIG. 37). At step 3902, the compressed combined data file may be decompressed by the one or more processors. For example, the compressed combined data file may be decompressed without data loss, resulting in a decompressed combined data file at step 3708 that is substantially identical to the pre-compression combined data file at step 3902. Any type of lossless compression/decompression process may be used.

At step 3903, the one or more processors may separate the metadata from the combined data file, and write the metadata to a storage device in communication with the one or more processors. For example, at step 3903, the one or more processors may perform additional functions with the metadata, such as job management operations and/or tracking each allocation interaction. At step 3904, the one or more processors may separate the captured images from the remainder of the image data. At step 3905, the one or more processors may record the remainder of the image data in said storage device. At step 3906, the one or more processors may process the captured images to derive foot-related evaluations; and, at step 3907, said processors may determine whether another compressed combined data file is to be considered.

FIG. 40

Figure 40:
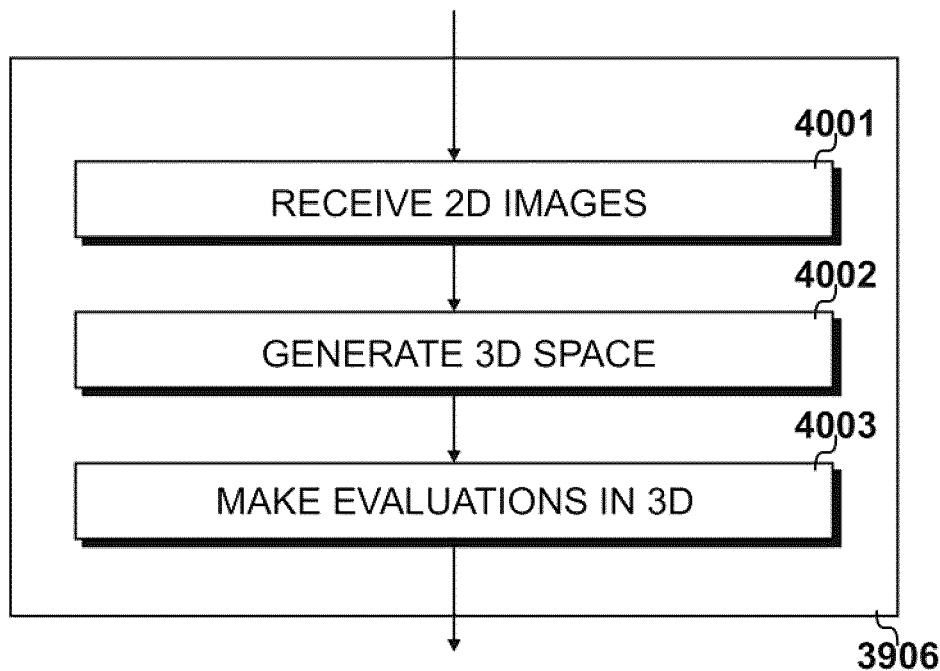
FIG. 40 shows exemplary procedures for processing the two-dimensional image data identified in FIG. 39, and generating a three-dimensional space therefrom.

Exemplary procedures 3906 (FIG. 39) for processing the captured images with one or more processors are detailed in FIG. 40.

At step 4001, the captured images separated from the combined image file at step 3904 (FIG. 39) may be received by the one or more processors. Each captured image may be identified as a two-dimensional image of the recipient's feet, and the one or more processors may generate a three-dimensional space from the two-dimensional images. For example, at step 4002, the one or more processors may process the two-dimensional images in order to generate point clouds in the three-dimensional space. The point clouds may allow the feet to be considered and processed further as three-dimensional objects within the three-dimensional space. As described further below, a point cloud may be generated for each foot, allowing the feet to be considered and processed individually and/or together.

At step 4003, the one or more processors may make foot-related evaluations in the three-dimensional space.

Numerous exemplary processing steps are described herein. As shown in FIG. 40, for example, the one or more processors may evaluate a shape of the feet within the three-dimensional space at step 4003. A scaling operation may be performed by the one or more processors at step 4001. As described below, the scaling operation may allow the one or more processors to evaluate the shape by obtaining actual measurements from the three-dimensional space.

The actual measurements may be identified as evaluations because they may enable the determination of foot related attributes of the recipient based on the captured images, without taking physical measurements of the recipient's feet. For example, because of the scaling operation, the one or more processors may make evaluations in the three-dimensional space that are similar to quantities that could be measured for a real foot. Some evaluations may be consistent with the foot measurements shown in FIG. 1. Alternatively, the evaluations may represent characteristics of feet that are significantly different from the type of data that would be produced for real foot measurements, such as measurements derived by the one or more processors for use in process 310.

In some aspects, evaluation process 310 may not be concerned with making absolute determinations of foot size and/or may not output any indicia of foot size according to any known sizing systems. Instead, process 310 may be performed with the one or more processors by matching foot parameters and/or preferences of each recipient with foot parameters and/or preferences established for another recipient, such as a fit leader, with or without reference to foot size.

Many aspects described above are configured to support process 310 by promoting the receipt of high quality two-dimensional images. For example, each captured image received at the one or more processors may have been captured based on video feed 601 during a predetermined motion of apparatus 305, such as the above-described sweeping motion.

FIG. 41

Figure 41:
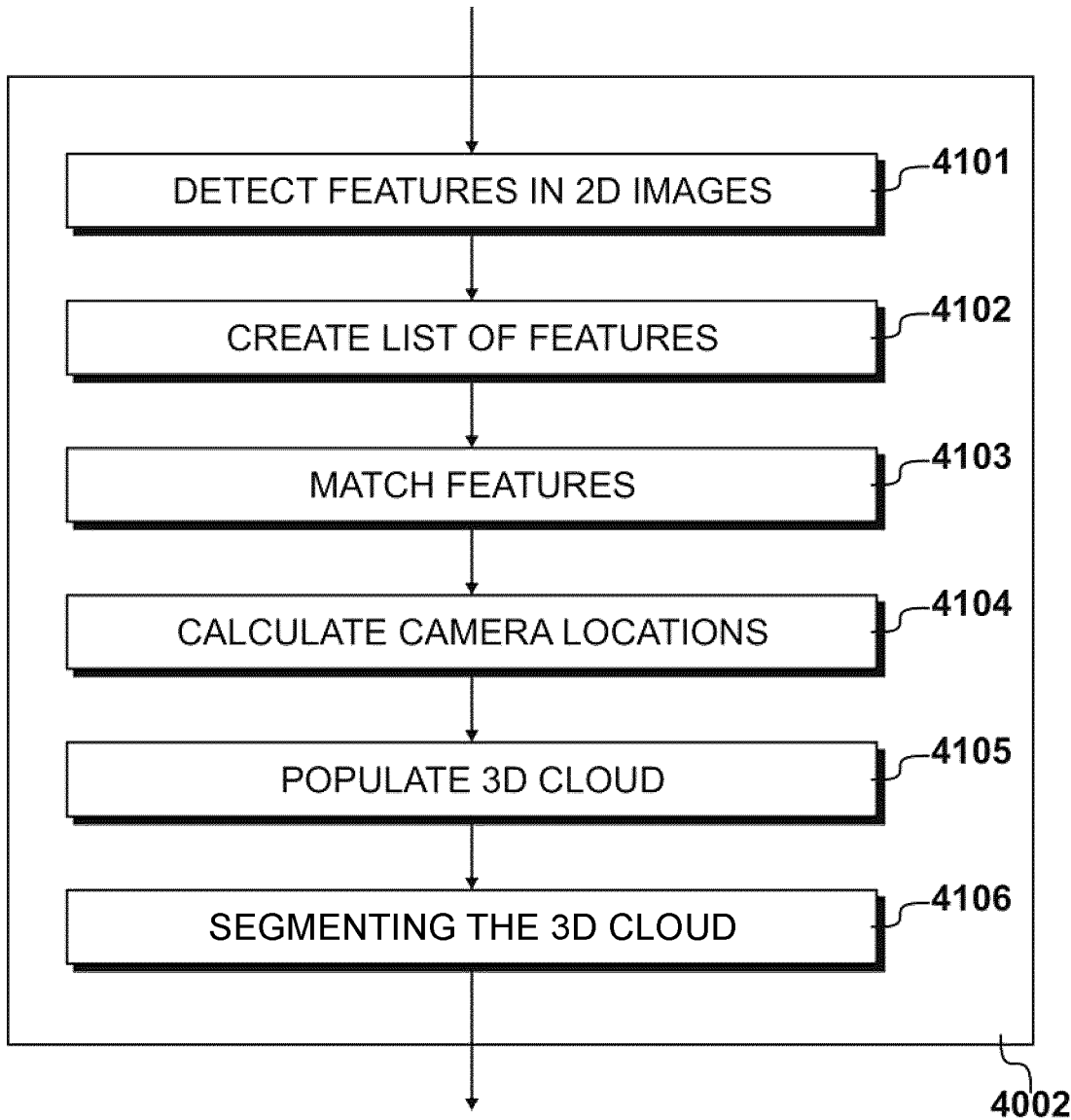
FIG. 41 shows exemplary procedures for generating the three-dimensional space identified in FIG. 40.

Exemplary procedures 4002 for generating a three-dimensional space are illustrated in FIG. 41. As before, aspects of procedures 4002 may be performed by one or more processors, which may include processor 401 of apparatus 305 (FIG. 3) and/or processing device 3801 (FIG. 38).

At step 4101 of FIG. 41, the one or more processors may detect foot features in the two-dimensional images. Any detection procedures may be used, including those described below with reference to FIGS. 43 to 45. In some aspects, each foot feature may appear in at least three of the two-dimensional images taken from different camera positions, allowing for triangulation of said features. Some foot features may be small, represented by a small number of adjacent or contiguous pixels. Other foot features may be identified by pixels representing discontinuities or edges, such as where a foreground group of pixels of a first luminance and/or colour transition into a background group of pixels of a second luminance and/or colour.

Aspects of this disclosure include constraints that may promote detection of the foot features with the one or more processors. For example, as shown in FIGS. 23 to 32, the same camera 403 may be used produce the two-dimensional images, allowing apparatus 305 to maintain similar settings for camera 403 during production. As also shown in FIGS. 23 to 32, each two-dimensional image may have been captured based on video feed 601 during a predetermined motion that limits the subset of all possible images. Some of these motions may provide constraints by allowing the distance between camera 403 and the feet to remain substantially the same for all of the two-dimensional images. In the sweeping motion, for example, apparatus 305 may be rotated with the outstretched arm so as to maintain a similar distance between camera 403 and the pair of feet and the scaling object 2302 during the sweeping motion.

The quality controls described above also may be constraints that promote detection of foot features. For example, the quality testing procedures 1708 depicted in FIGS. 17 and 36 may test aspects of the quality of each captured image, such focus and/or dynamic range so that the quality of each two-dimensional image may be controlled.

These exemplary constraints may produce a greater number of similarities between each of the two-dimensional images, making it easier for the one or more processors to use the resulting two-dimensional images in subsequent processes without error. Adjacent images may have the most similarities. Therefore, the one or more processors also may identify and/or determine an order for the two-dimensional images based on the azimuth angles of camera 403, and use the order as an additional constraint. For example, the image data may include the captured images and an order of said images, allowing the one or more processors to determine the order from the image data. In addition and/or alternatively, the position of camera 403 may be tracked by IMU 409, output as position data, and uploaded to the one more processors in the compressed combined data file, allowing for determination of the order from the position data. Either way, it becomes possible to consider the two-dimensional images in the order, maximizing similarities between the images, and making them easier to process for specific purposes, such as locating the positions of camera 403 in the three-dimensional space.

Individually and/or in combination, these constraints may reduce the processing power requirements of procedures 4002. For example, these reductions may aid processing device 3801, and/or allow processor 401 to perform additional aspects of procedures 4002. Moreover, as the available processing capability of processor 401 increases, then it may become possible for procedures 4002 to be performed entirely by processor 401.

After identifying foot features in the two-dimensional images, at step 4102, the one or more processors may generate a list of the identified foot features. In some aspects, the list may include a type and a location of each identified foot feature, and the one or more processors may record the types and location within their respective two-dimensional images (e.g., as coordinate points on a two-dimensional plane defined by the image). At step 4103, the one or more processors may match an identified foot feature in a first two-dimensional image with a corresponding identified foot feature in other two-dimensional images. Any matching process may be used. For example, step 4103 may comprise performing a pair-wise comparison of identified features in the two-dimensional images, and/or looking for image pair candidates that contain corresponding identified foot features.

At step 4104, the one or more processors may locate camera positions for each two-dimensional image. For example, each camera position may be located by triangulating identified foot features, and generating points in the three-dimensional space.

At step 4105, after locating the camera positions, the one or more processors may generate the three-dimensional point cloud in the three-dimensional space. For example, step 4105 may comprise repeating step 4104 in order to populate the three-dimensional point cloud by defining points in the three-dimensional space for the identified foot features. In some aspects, each point in the three-dimensional point cloud may represent position data for the identified foot feature in three-dimensional space, such as coordinates, in which case the specific nature and/or type of the foot feature may no longer being required. With this approach, a new set of three-dimensional position data may be generated by the one or processors during procedures 4002 in the form of a three-dimensional point cloud representing the recipient's feet and the floor upon which they were standing.

Aspects of the three-dimensional point cloud may be further processed to increase the accuracy of subsequent evaluations. For example, at step 4106, the three-dimensional point cloud may be segmented by the one or more processors into a plurality of separate point clouds. At least three separate point clouds may be segmented. For example, step 4106 may including segmenting the point clouds into a left foot cluster, a right foot cluster, and a ground cluster, allowing for separation of both feet from one another and the ground. As described below, each separate point cloud may be analysed differently by the one or more processors.

FIG. 42

Figure 42:
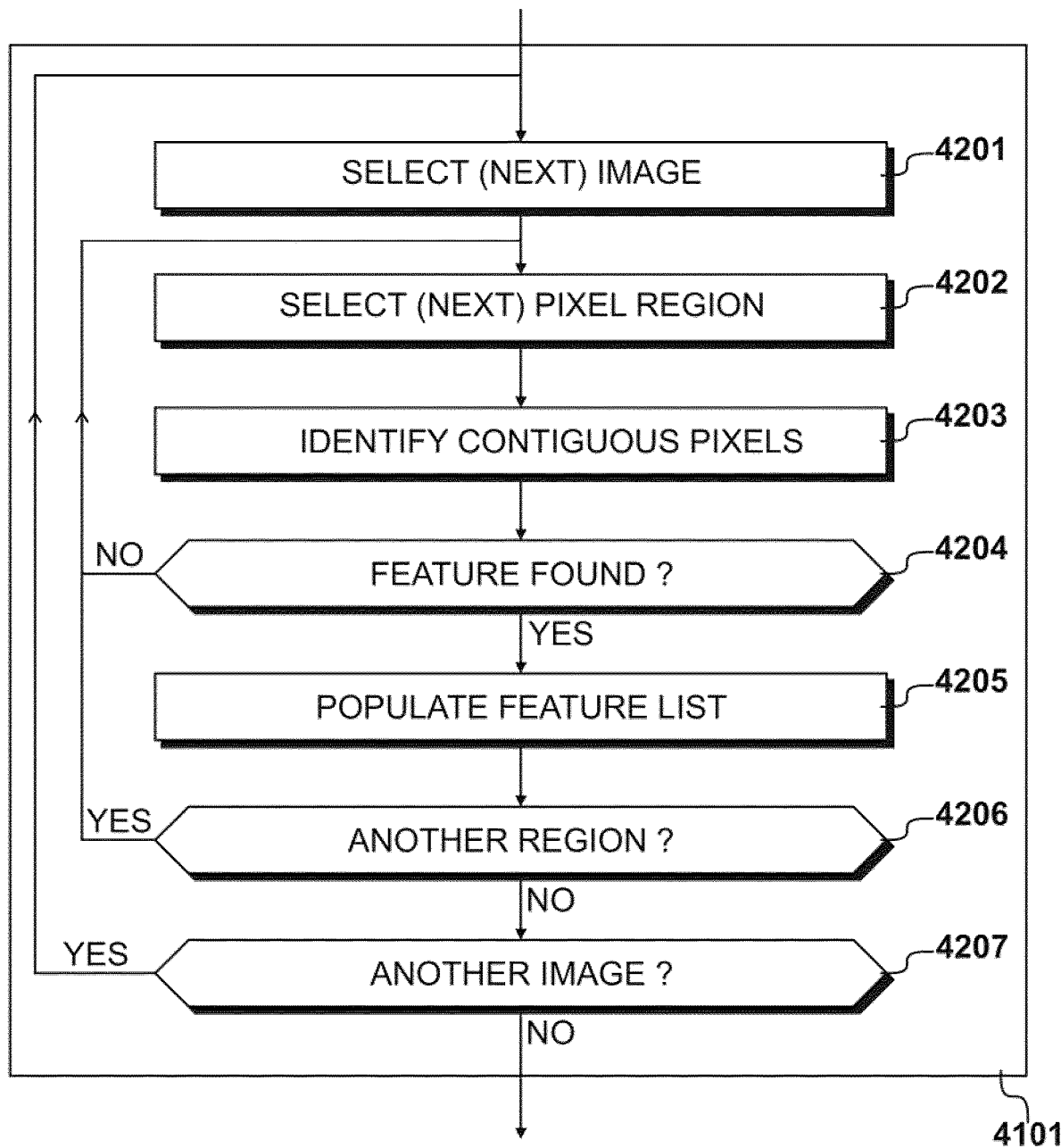
FIG. 42 details exemplary procedures for detecting foot features in the two-dimensional images identified in FIG. 41.

Exemplary procedures 4101 (FIG. 41) for detecting foot features in the two-dimensional images are detailed in FIG. 42.

One detection procedure involves a comparative process (or processes). As shown in FIG. 42, at step 4201, the one more processors may select a first two-dimensional image; and at step 4202, the one or more processors may divide the first two-dimensional image into a plurality of pixel regions, and select one of the pixel regions.

As shown at step 4203 of FIG. 42, the one or more processors may identify foot features by performing the comparative process on a first pixel region. Exemplary comparative processes are described below with reference to FIGS. 43 to 45, and may be repeated for each pixel region.

At step 4204, the one or more processors may determine whether a foot feature has been identified in the selected pixel region. If a foot feature has not been identified, then the one or more processors may select the next pixel region by returning to step 4202. If a foot feature has been identified, then the processors may populate the list of identified features at step 4205.

At step 4206, the one or more processors may determine whether another pixel region is to be considered. If answered in the affirmative, then the processors may select the next pixel region by returning to step 4202.

Eventually, all of the pixel regions within the first two-dimensional image will have been considered, so that the one or more processors may answer the question asked at step 4206 in the negative. At step 4207, the one or more processors may determine whether another image is present. If this question is answered in the affirmative, then the processors may select the next two-dimensional image at step 4201, and repeat procedures 4101 until all of the images have been considered, allowing the question asked at step 4207 to be answered in the negative.

To minimize processing requirements, the one of more processors may terminate procedures 4101 prior to consideration of all the two-dimensional images. For example, procedures 4101 may be run concurrently with procedures 4102 to 4106, allowing the processors to continually monitor characteristics of the three-dimensional point cloud (e.g., density), and terminate procedures 4101 based on the monitored characteristics.

FIG. 43

Aspects of an exemplary comparative process are detailed in FIG. 43, which depicts a two-dimensional image 4301 that has been selected and divided by the one or more processors according to the steps 4201 and 4202 of FIG. 42. In this example, image 4301 has been divided into a plurality of pixel regions at step 4202, including a first region 4302, a second region 4303, a third region 4304, and so on, up to at least an eleventh region 4312, a twelfth region 4313, and a thirteenth region 4314. The count of each pixel region may progress horizontally and vertically across image 4301, and the selection of each pixel region at step 4202 may be consistent with the count. For example, the selection of each pixel region at step 4202 may include a horizontal progression for pixel regions 4302, 4303, 4304, and so on, in keeping with the count; after a vertical progression, the count may continue horizontally for pixel regions 4312, 4313, 4314, and so on, once the previous horizontal progression has been completed. Any direction and/or combination of directions may be used, on any form of grid, with the aforementioned horizontal and vertical progressions being examples.

At step 4203 of procedures 4101 (e.g., FIG. 42), the one or more processors may use the comparative process to analyse each pixel region. Exemplary aspects of step 4203 are depicted in FIG. 43, in which the one or more processors have selected a first pixel 4321 from first pixel region 4302, and compared the first pixel 4321 against contiguous pixels 4322, 4323, and 4324. As shown in FIG. 42, no foot features have been identified in this first iteration, causing the one or more processors to select a second pixel adjacent to first pixel 4321, and repeat step 4203 for the second pixel. As also shown in FIG. 42, no foot features have been identified in this second iteration either. The one or more processors may continue adjacent selecting pixels within first pixel region 4302 until all of the pixels within region 4302 have been considered.

Once all of the pixels in the first pixel region 4302 have been analysed, the one or more processors may answer the question asked at step 4206 of FIG. 42 in the affirmative, and return to step 4202 for selection of the next pixel region, which is second pixel region 4303 in this example. As before, each adjacent pixel in the second pixel region 4303 may be considered and compared against contiguous pixels at step 4203. But on this iteration, the one or more processors may detect a similarity between contiguous pixels 4331 and 4332 (e.g., colour), and use the detected similarity to identify a surrounding group of pixels 4333, illustrated as a shaded portion of second pixel region 4303 in FIG. 43. The one or more processors may then answer the question asked at step 4204 in the affirmative; and populate the feature list at step 4205 with data regarding the identified feature.

Once all of the pixels in the second pixel region 4303 have been analysed, the one or more processors may again answer the question asked at step 4206 of FIG. 42 in the affirmative; and return to step 4202 for selection of the next pixel region, which is third pixel region 4304 in this ongoing example. The comparative process may continue in this manner, repeating the question at step 4206 until each pixel region has been selected. For example, as shown in FIG. 43, the process may continue until the twelfth region 4312 is selected at step 4202, allowing a foot feature 4343 to be identified at step 4203, and added to the feature list at step 4205. In the current example, it may be assumed that the one or more processors would determine that pixel regions 4304, 4313, and 4314 of FIG. 43 do not contain any foot features based on their lack of contiguous pixels.

Accordingly, the presence of contiguous pixels may be used to identify foot features in each pixel area. Various comparative processes may be applied to the contiguous pixels. In some aspects, the same comparative process may be used to analyse each pixel region, as shown in FIG. 43, which depicts a comparative process 4341. As shown, first pixel region 4302 may be analysed by comparative process 4341, which searches for similarities between contiguous pixels, and returns a null result due the lack of contiguous pixels in region 4302. For comparison, FIG. 43 also shows that the second pixel region 4303 and twelfth pixel region 4312 may be analysed by the same procedure 4341. As shown, procedure 4341 identifies a cross-shaped foot feature 4342 in region 4303 that may correspond with an intersection of tendons and/or veins; and a rectangular-shaped feature 4343 in region 4312 that may correspond with a skin discoloration.

FIG. 44

Figure 44:
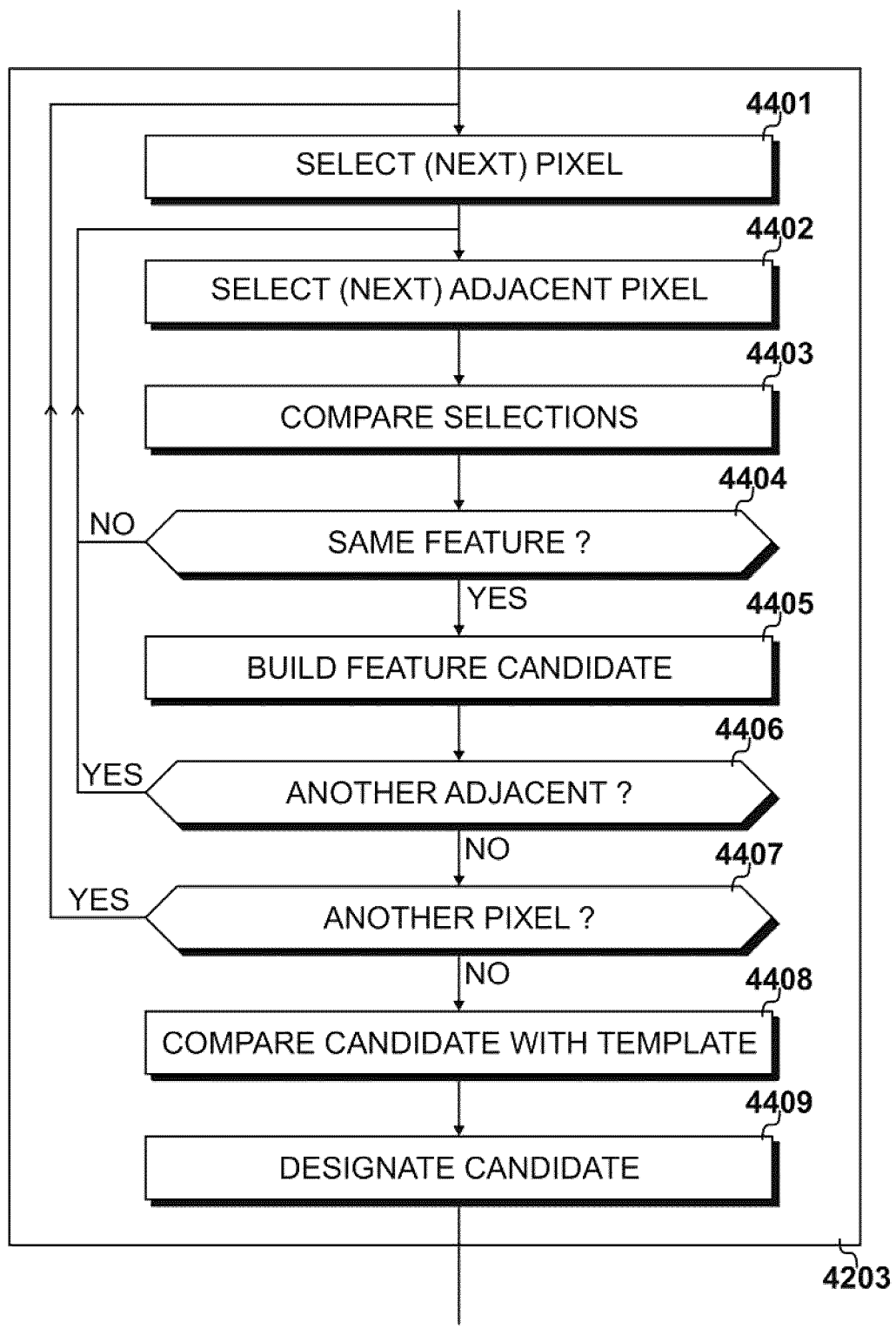
FIG. 44 details exemplary procedures for identifying foot features from the pixels shown in FIG. 43.

Additional exemplary procedures 4203 for identifying contiguous pixels, as illustrated in FIG. 43, are detailed in FIG. 44.

At step 4401, for example, the one or more processors may select a first pixel that, on this first iteration, may be representative of the first pixel 4321 of the first pixel region 4302 of the image 4301 depicted in FIG. 43. At step 4402, the one or more processors may select a first adjacent pixel that, on this iteration, may be representative of the second pixel 4322 of first pixel region 4302 of image 4301. As shown in FIG. 43, pixels 4321 and 4322 are contiguous. At step 4403, the one or more processors may perform a comparison of contiguous pixels 4321 and 4322. At step 4404, based on the comparison, the processors may determine whether the contiguous pixels 4321 and 4322 form part the same foot feature. For example, at step 4404, the one or more processors may identify characteristics of pixels 4321 and 4322 (e.g., colours); and determine whether they form part of the same foot feature based on similarities between the identified characteristics.

Upon determining that the contiguous pixels 4321 and 4322 are not part of the same feature, the one or more processors may answer the question of step 4404 in the negative, and return to step 4402. In the ongoing example, the next adjacent pixel, representative of a third pixel 4323 of the first pixel region 4302 of the image 4301 depicted in FIG. 43, may be selected and again compared with a contiguous pixel, such as the first pixel 4321 of first region 4302 of image 4301. Again, on this iteration, the one or more processors may answer the question at step 4404 in the negative.

Absent interruption, these processes may continue until all of the pixels in the first region 4302 of image 4301 have been considered. After which, at step 4202 of FIG. 42, the next pixel region may be selected by the one or more processors. For example, the one or more processors may similarly select the second pixel region 4303 of the image 4301 at step 4202; compare a first pixel 4331 with a second pixel 4332 contiguous therewith at step 4403; and determine whether pixels 4331 and 4332 form part of the same foot feature at step 4404. In this instance, however, the processors may determine that contiguous pixels 4331 and 4332 are part of the same feature, depicted as a potential foot feature 4333 in FIG. 43.

The determination made at step 4404 may be probabilistic. For example, the one or more processors may identify characteristics of pixels 4331 and 4332 (e.g., colours); and determine probabilities that pixels 4331 and 4332 are part of the potential foot feature 4333 based on similarities between the identified characteristics. Based on their probabilities, at step 4406, the one or more processors may generate a feature candidate model including pixels 4331 and 4332. The feature candidate model may be expanded to include additional contiguous pixels with subsequent iterations of steps 4401 to 4404. As shown in FIG. 43, the feature candidate model may be expanded to include the pixels of potential foot feature 4333.

At step 4406 the one or more processors may determine whether there is another adjacent pixel to consider. If the determination is affirmative, then the one or more processors may select the next adjacent pixel at step 4402. Alternatively, if the determination is negative, then the one or more processors may determine whether another pixel is present within the image at step 4407. If this determination is affirmative, then processors may begin the next iteration by selecting the next pixel at step 4401.

When no further pixels are present, the determination at step 4407 may be negative, directing the one or more processors to step 4408. For example, at step 4408, the one or more processors may compare each feature candidate model with a predetermined reference model, such as a foot feature template. Step 4408 may complete the comparative process shown in FIG. 43. For example, if the process performed at step 4408 identifies similarities between the feature candidate model and the foot feature template, then the processors may designate potential foot feature 4333 as a candidate foot feature 4342 at step 4409. As shown in FIG. 43, on a further iteration, the processors also may designate a potential foot feature 4334 as a candidate foot feature 4343 at step 4409.

Other comparative processes are contemplated, including processes that do not require template matching. For example, the one or more processors may calculate a feature strength measure (e.g., based the probabilities described above) for every pixel in first image 4501, and then apply a predetermined threshold value to image 4501 to generate a finite number of feature points. In some aspects, the one or more processors may identify peaks in the thresholded image 4501, and submit those peaks to non-maximum suppression to ensure that neighbouring pixels are not counted as feature points. Once these points have been identified, the one or more processors may generate feature descriptor vectors therefrom, and apply the comparative process to the feature descriptor vectors.

The feature descriptor may be related to the quantities calculated in order to identify the feature points. For example, the one or more processors may identify an image patch (e.g., 5×5 pixels) centred on the feature points, and rearrange the RGB values into a vector (e.g., of length 25×3=75). In other examples, such as with SIFT, the one or more processors may use a local histogram of gradient orientations and normalize the histogram to make it rotation invariant. Either way, one or more processors may match the vectors and/or histograms across images, as shown in FIG. 45.

FIG. 45

Figure 45:
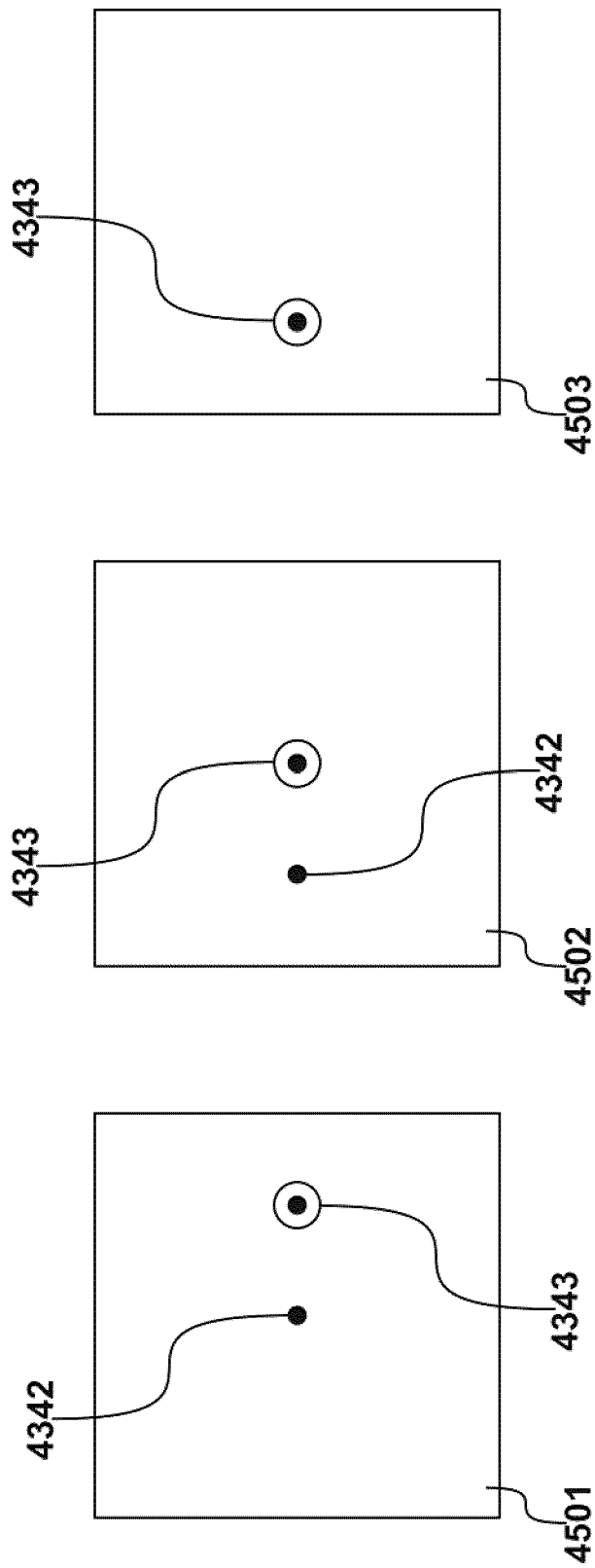
FIG. 45 shows examples of two-dimensional images with identified foot features.

Exemplary aspects of identifying foot features are detailed in FIG. 45 and now described.

It should be appreciated that, in various aspects, any number of foot features (including up to and including thousands of foot features or more) may be identified in each two-dimensional image, and then compared between images. For the purposes of illustration, FIG. 45 depicts a first two-dimensional image 4501 adjacent with a second two-dimensional image 4502 that is, in turn, adjacent with a third two-dimensional image 4503. In the first image 4501, a first foot feature 4342 and a second foot feature 4343 have been identified by the one or more processors.

Another first foot feature 4342 has also been identified by the one or more processors in the second image 4502. Similarly, another second feature 4343 has been identified in second image 4502 and third image 4503. As described above, the one or more processors may use a comparative process to determine whether the first feature 4342 of first image 4501 is the same as the first feature 4342 of second image 4502, but with a different camera position.

FIG. 46

Exemplary aspects of step 4104 of procedures 4002 (FIG. 41) are now described with reference to FIG. 46. At step 4104, the one or more processors may locate camera positions for camera 403 in each two-dimensional image. For example, having identified foot features within the first image 4501, the one or more processors may position image 4501 in a three-dimensional space by triangulating the identified foot features.

Figure 46:
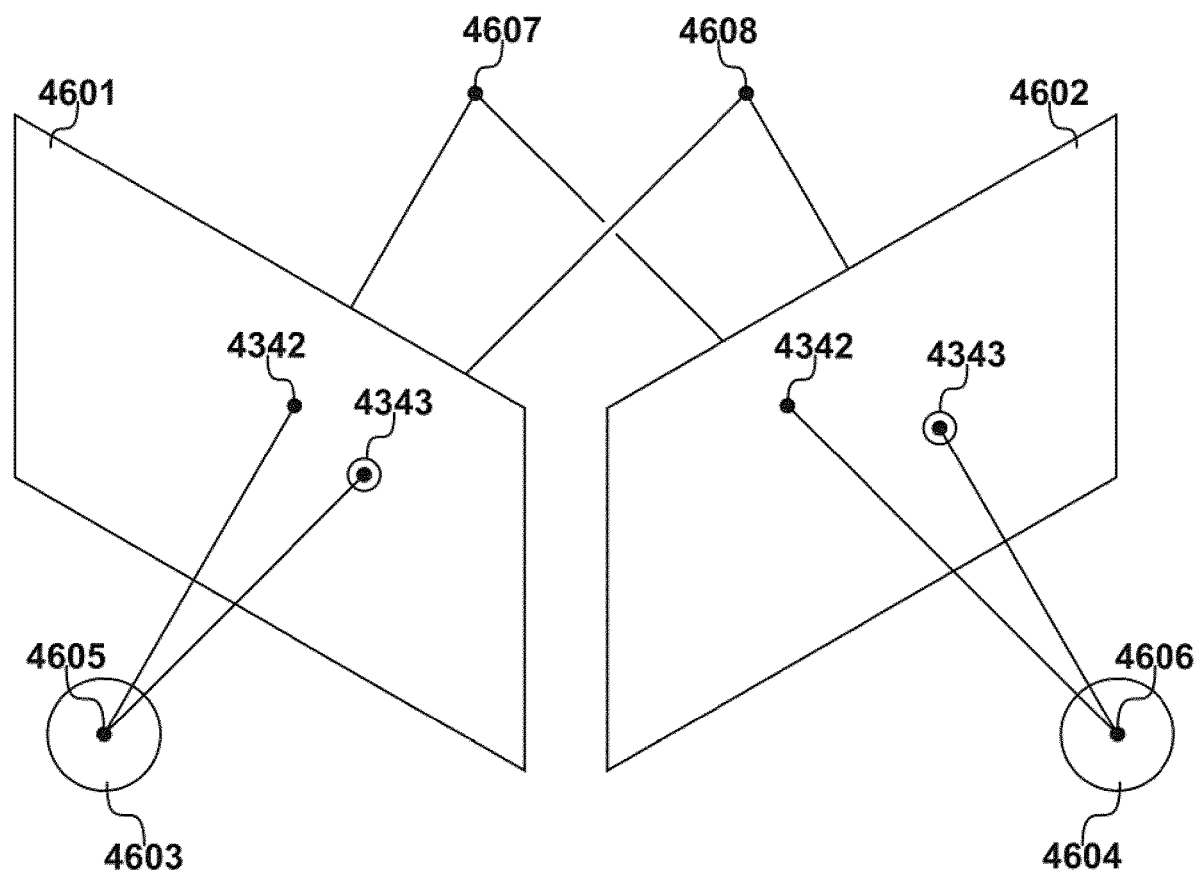
FIG. 46 shows an exemplary triangulation diagram, in which two-dimensional images are positioned in a three-dimensional space.

An exemplary triangulation diagram is shown in FIG. 46, identifying a first two-dimensional plane 4601 and a second two-dimensional plane 4602 in a three-dimensional space. First image 4501 of FIG. 45 may positioned in the three-dimensional space as first plane 4601; and second image 4502 of FIG. 45 may be positioned in three-dimensional space as second plane 4602. As shown in FIG. 46, the one or more processors may locate the respective first and second foot features 4342 and 4343 in each of the first and second planes 4601 and 4602. In this example, only two foot features 4342 and 4343 have been located, although many foot features of this type (e.g., hundreds or thousands) may exist in both of planes 4601 and 4602.

The camera positions of images 4501 and 4502 may be known to the one or more processors. For example, according to procedures described above, the position of camera 403 of apparatus 305 in the three-dimensional space may have been determined by processor 401 and/or IMU 409 for both of images 4501 and 4502, stored in storage device 409, and/or received by the one or more processors in the combined data file. Based on these positions, the one or more processors may determine that for image 4601, camera 403 must have been in a first approximate three-dimensional region 4603; and for image 4602, camera 403 must have been within a second approximate three-dimensional region 4604.

Additional accuracy may be required. Accordingly, a triangulation process may be performed by the one or more processors to determine further camera positions for each of the first and second planes 4601 and 4602. Any triangulation process may be used. As shown in FIG. 46, the one or more processors may perform the triangulation process to locate a first camera position 4605 for camera 403 when capturing the first image 4501 positioned as first plane 4601, and a second camera position 4606 for camera 403 when capturing the second image 4601 positioned as second plane 4602. As also shown in FIG. 46, the first camera position 4605 may be located within the first approximate three-dimensional region 4603, and the second camera position 4606 may be located within the second approximate three-dimensional region 4604.

As shown in FIG. 46, the same first foot feature 4342 is shown in both of the first and second images 4501 and 4502. Accordingly, once the first camera position 4605 is known (or approximately known as region 4603), the one or more processors may locate a position 4607 of the first feature 4342 in the three-dimensional space using the triangulation procedures set forth herein. As shown in FIG. 46, said processors may locate a position 4608 of the second foot feature 4343 in the three-dimensional space using the same procedures; and to repeat these procedures for each additional foot feature.

Once located in the three-dimensional model, the position (e.g., positions 4607 and 4608) of each foot feature (e.g., features 4342 and 4343) may represent a three-dimensional point on a surface of the recipient's feet. Accordingly, by locating positions for a sufficient number of foot features in the three-dimensional model using the procedures described herein, the one or more processors may generate a three-dimensional point cloud of the feet based on the positions of each foot feature. As described herein, the point cloud may include separate point clouds representing surfaces of a left foot, a right foot, a floor, and/or a combination thereof.

FIG. 47

Figure 47:
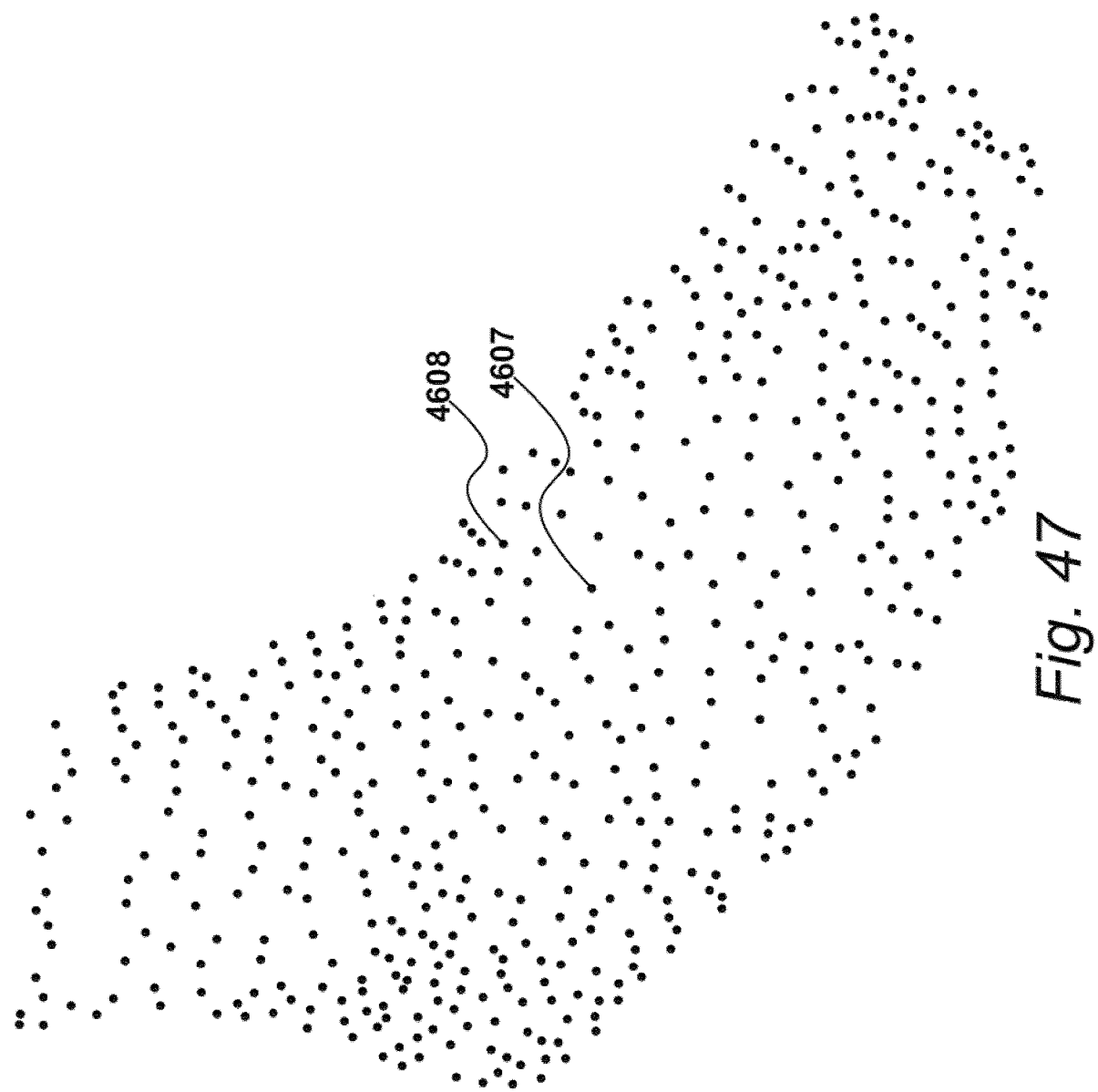
FIG. 47 shows an example of a point cloud.

Exemplary aspects of step 4105 of procedures 4002 (FIG. 41) are now described with reference to FIG. 47. An exemplary point cloud representing one of the recipient's feet is shown in FIG. 47 after being generated by the process illustrated in FIG. 46. As shown, the point cloud may include first feature 4342 at position 4607, and second feature 4343 at position 4608. In this example, aspects of the two-dimensional images 4501 and 4502 (FIG. 45) have been transformed into the depicted point cloud, which provides a three-dimensional representation of the foot, including representations of features 4342 and 4343. As described further below, the one or more processors may derive foot-related evaluations from this three-dimensional representation.

As shown in FIG. 46, step 4104 of procedures 4002 may be used to calculate camera positions for each two-dimensional image, including the first camera position 4605 for first image 4501 and the second camera position 4606 for second image 4502. At step 4105, based on these camera positions, the one or more processors may locate additional positions in the three-dimensional model by performing additional reconstruction operations, such as ray tracing operations that create a dense reconstruction.

In other aspects, the one or more processors may calculate a confidence level for each new point generated by the additional reconstruction procedures. For example, the comparative process performed at step 4408 above may identify similarities between the feature candidate model and the foot feature template. Based on these similarities, at step 4409, the processors may designate potential foot feature 4333 as a candidate foot feature 4342 with a high confidence level, suggesting that feature 4342 is most likely valid. In this example, the one or more processors may use the confidence level of feature 4342 to determine how many new points may be added to the point cloud based by performing additional reconstruction procedures on feature 4342, such as ray tracing.

At step 4105, the one or more processors may include new points from these additional procedures when there is a high level of confidence that the new points are valid; and exclude such points when it is not possible to obtain this level of confidence.

FIG. 48

Exemplary aspects of step 4106 of procedures 4002 (FIG. 41) are now described with reference to FIG. 48.

As shown, step 4106 may comprise segmenting the three-dimensional point cloud into a plurality of separate point clouds. As described above, the point cloud may be generated by the one or more processors at step 4105 of procedures 4002 after receiving two-dimensional images of the recipient's feet while standing on a substantially horizontal surface, such as a floor. Accordingly, the point cloud may include points representing the feet (or "foot points"), and points representing the horizontal surface (or "ground points". Step 4106 may be used to the foot points from the ground points.

Figure 48:
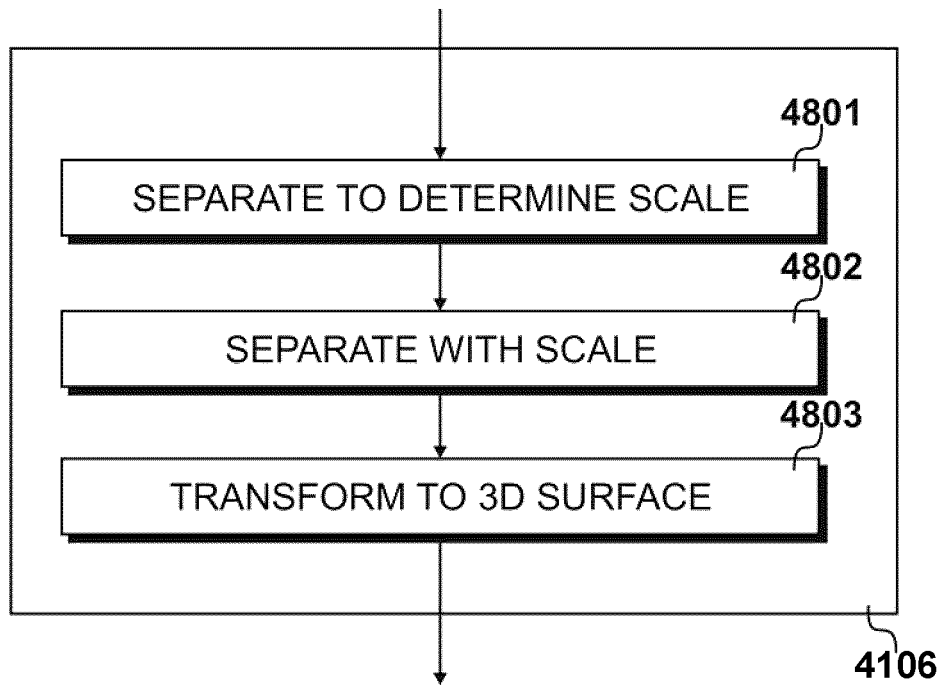
FIG. 48 shows exemplary processes performed upon the point cloud identified in FIG. 47.

An exemplary step 4106 for segmenting the point cloud is detailed in FIG. 48. At step 4801, the one more processors may perform a first segmentation to determine a scale of the point cloud. Thereafter, having determined the scale, the one or more processors may separate the foot points from the ground points at step 4802; and transform the foot points into a three-dimensional surface at step 4803.

Additional aspects of steps 4801, 4802, and 4802 are now described with reference to FIGS. 49 to 63.

FIG. 49

Figure 49:
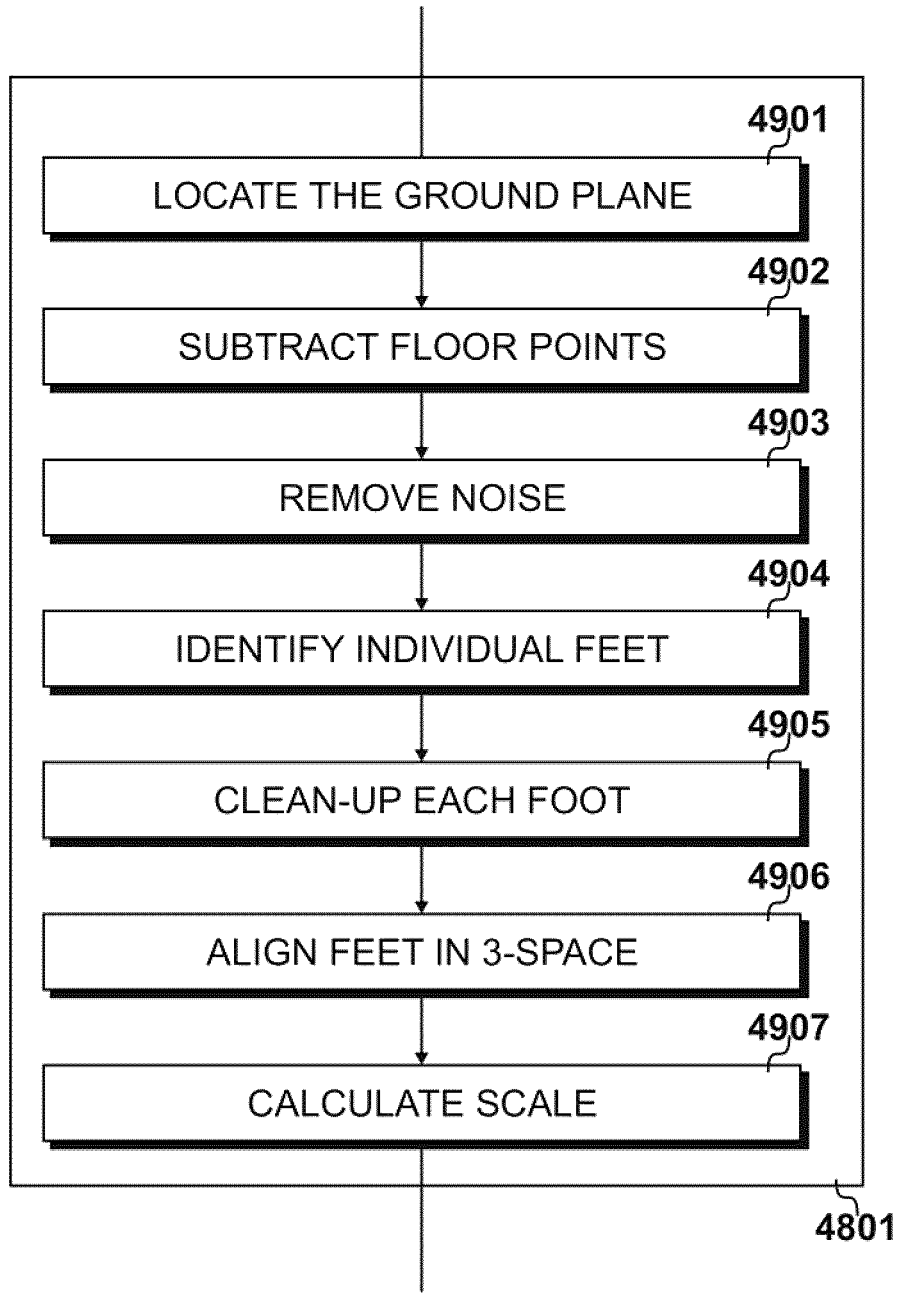
FIG. 49 details exemplary procedures for separating the feet in in the point cloud identified in FIG. 48.

Aspects of an exemplary step 4801 (FIG. 48) for segmenting and/or scaling the point cloud are detailed in FIG. 49.

At step 4901, the one or more processors may locate a ground plane in the three-dimensional space. For example, each of the aforementioned ground points may be contained within a horizontal zone, and the one or more processors may locate the ground plane within the zone. At step 4902, the one or more processors may subtract the ground points from the point cloud. For example, the processors may estimate a depth between the foot points and the ground points, and subtract the ground points by moving the ground plane based on the depth. Additional aspects of steps 4901 and 4902 are described below with reference to FIG. 50. For example, the maximum displacement may be based on a predetermined upper limit (e.g., approximately 5-10 millimetres); and/or determined by the one or more processors relative to the foot points (e.g., approximately 1-2 times an estimated maximum width of the point cloud). Either way, at this point, the one or more processors may not be able to distinguish between the foot points and noise At step 4903, the one or more processors may perform a first clean-up process to remove noise from the three-dimensional point cloud. For example, the first clean-up process may comprise applying a filter to identify points that are significantly displaced from the foot points, and removing the identified points from the clouds. The filter may be based on local statistics of the point cloud. For example, at a selected point, the one or more processors may compute an average spacing distance to its nearest neighbours, and compare the average distance to an average spacing distance of the cloud. If the selected point is isolated and/or separated from the cloud (e.g., an outlier), then the average spacing distance may be larger than the average spacing distance of the cloud. Other filter types may be used. For example, another filter may compute the number of points within a pre-defined 3D radius (e.g., of 5 millimetres) in the scaled metric cloud, and remove points with insufficient neighbours inside the radius. Some clumps of points (known as "structured outliers") may not be removed at step 4903 because they may have cohesion, making the statistics appear normal. As described below, these clumps may be removed by other methods.

At step 4904, the one or more processors may identify feet within the point cloud; and further segment the point cloud into separate point clouds for each foot. For example, step 4904 may comprise using the processors to identify at least two main clusters of points within the point cloud, and segment the point include into a left foot cluster and a right foot cluster.

At step 4905, the one or more processors may perform a second clean-up process to remove noise from each of the separate point clouds, such as the left foot cluster and the right foot cluster. For example, the second clean-up process may similarly comprise identifying points that are significantly displaced from the left foot and right foot clusters, and removing the identified points from the clusters.

At any time (e.g., during step 4801), the one or more processors may determine an orientation of the three-dimensional space with respect to a global set of intersecting axes. For comparison, the orientation of each separate point cloud with respect to the global axes may be unknown after step 4905 because each cloud is merely a collection of points at this point. Accordingly, at step 4906, the one or more processors may align the separate point clouds within the three-dimensional space. For example, the one or more processors may determine an orientation of the left foot cluster with respect to a first local set of intersecting axes; determine an orientation of the right foot cluster with respect to a second local set of intersecting axis; and align both of the first and second local axes with the global axes, thereby aligning the feet in the three-dimensional space.

At step 4907, the one or more processors may determine a scale of the three-dimensional space. For example, with reference to a scaling object (e.g., object 2302 of FIG. 23), the one or more processors may perform a scaling operation at step 4907 in order to calculate a scale for the three-dimensional model. Additional aspects of step 4907 are described below with reference to FIGS. 53 through 55.

According to these exemplary aspects of step 4801, at least two point clusters may be identified. Each cluster may represent an individual foot, such as the left foot cluster and right foot cluster described above. Additional steps may be performed by the processors to enhance the quality of the clusters. For example, various steps may be performed to increase the density of the clusters (e.g., at step 4104 of FIG. 41); remove noise from each cluster (e.g., steps 4903 and 4905 above); and/or confirm that each point with each cluster may contribute to defining the external surfaces of the feet in three-dimensional space (e.g., at step 4803 of FIG. 48).

FIG. 50

Figure 50:
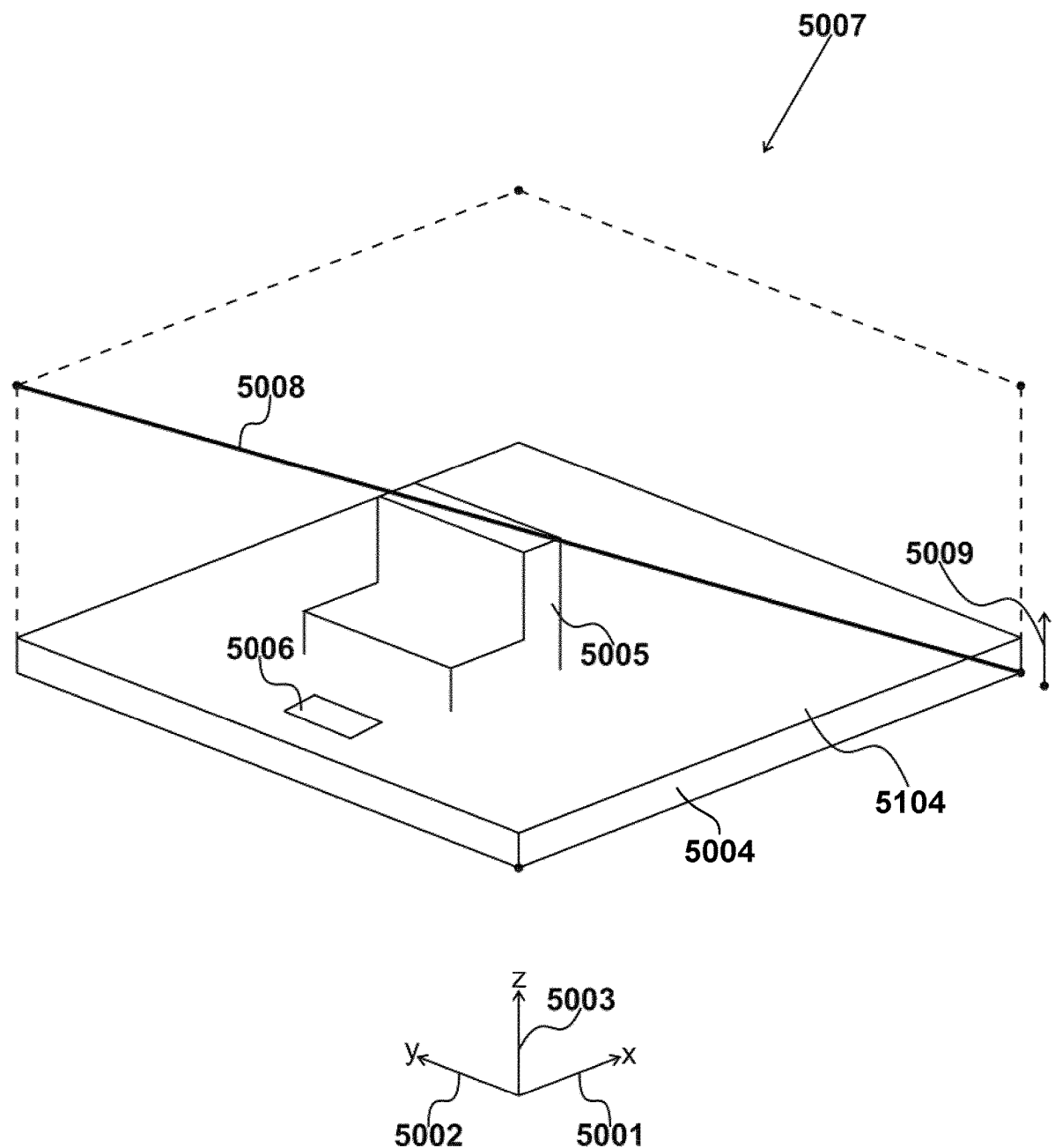
FIG. 50 shows an example of a three-dimensional space generated in accordance with the exemplary procedures identified in FIG. 40.

Additional aspects of steps 4901 and 4902 (FIG. 49) are detailed in FIG. 50, which depicts an exemplary three-dimensional space 5007 generated by the one or more processors with process 4002 of FIG. 41.

As shown in FIG. 50, the one or more processors may determine an orientation of three-dimensional space 5007 with respect to a global set of intersecting axes. The global set of axes may include a first axis having an "x" dimension 5001, a second axis having a "y" dimension 5002, and a third axis having a "z" dimension 5003. As shown in FIG. 50, the three-dimensional space 5007 may include: a ground cluster 5004 including points representing the ground surface (e.g., a floor); a foot cluster 5005 including points representing the feet; and a scaling object cluster 5006 including points representing the scaling object (e.g., object 2302 of FIG. 23).

Points may exist at an interface between ground cluster 5004 and foot cluster 5005, and the one or more processors may not be able to define this interface. For example, without additional information, a degree of ambiguity may exist at the interface, making it difficult for the processors to accurately distinguish between floor points and foot points. To resolve this ambiguity, at step 4901, the one or more processors may locate a ground plane in the three-dimensional space. As shown in FIG. 50, at step 4901, the one or more processors may locate the ground plane anywhere between clusters ground cluster 5004 and foot cluster 5005

Additional aspects of locating an exemplary ground plane 5104 at step 4901 (FIG. 49) are now described. As shown in FIG. 50, the one or more processors may locate a diagonal vector 5008 in three-dimensional space 5007, determine a length of vector 5008, and determine an offset distance 5009 based on vector 5008. Step 4907 may not have been performed yet, meaning that an actual length of vector 5008 cannot be determined from space 5007. Nonetheless, a proportion of the length of vector 5008 may be used to determine offset distance 5009. As shown in FIG. 50, for example, ground plane 5104 may be an "xy" plane that has been positioned in three-dimensional space 5007 based on the offset distance 5009. In some aspects, ground plane 5104 may be defined as a provisional ground plane in order to perform the scaling operation at step 4907, and subsequently redefined to more accurately define the interface between clusters 5004 and 5005 after step 4907 has been performed.

The orientation of ground plane 5104 may be known prior to step 4901. For example, the orientation of plane 5104 may be established by assuming that the feet are located on a substantially horizontal surface (e.g., the floor). Alternative, the orientation of plane 5104 may be determined by IMU 409 from position data that includes a vertical dimension (indicated by axis 5003) due to the detection of gravity when the two-dimensional image was captured. However, prior to step 4907, there may be no scale, meaning that the processors cannot yet use the three-dimensional space 5007 to distinguish between a big thing at a distance and a small thing close up.

Additional assumptions may be used to simplify step 4901. For example, when space 5007 is viewed from above (e.g., as in FIG. 52), a majority of the points may be part of ground cluster 5004, such as those near a periphery of ground plane 5104; and a minority of the points may be part of foot cluster 5005, such as those near a central region of the ground plane 5104. Accordingly, at step 4901, the one or more processors may perform a random sampling operation that identifies a majority of the points as ground cluster 5004; determines characteristics of the majority of points, such as their "z" values; and locates plane 5104 based on these characteristics.

At step 4902, the one more processors may the use ground plane 5104 to subtract points from foot cluster 5004. For example, plane 5104 may be used to determine whether each point contributes to ground cluster 5004 (i.e., is part of the floor), or foot cluster 5005 (i.e., is part of the feet). The one or more processors may use offset distance 5009 to guide the subtraction. For example, the one or more processors may locate ground plane 5104 at a "z" value that is greater than the "z" values of the majority of points identified by the random sampling operation.

FIG. 51

Figure 51:
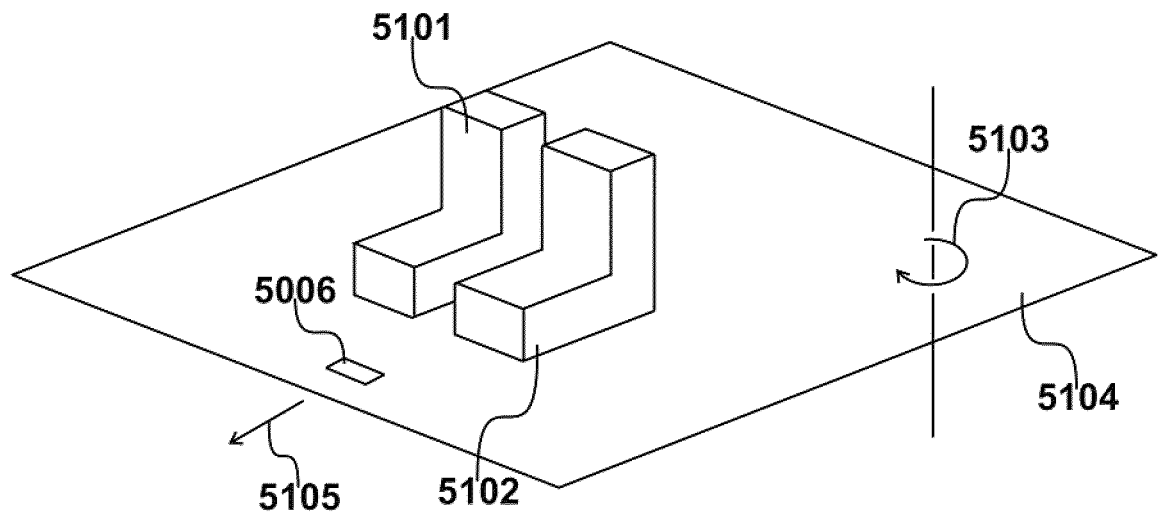
FIG. 51 illustrates an exemplary segmentation of the point cloud shown in FIG. 47 into a left foot cluster, a right foot cluster, a scaling object cluster, and a ground cluster.

Additional aspects of step 4906 (FIG. 49) are detailed in FIG. 51, which depicts the three-dimensional space 5007 of FIG. 50 after ground plane 5104 has been located at step 4901; the points from ground cluster 5004 have been subtracted at step 4902; noise has been removed at step 4903; foot cluster 5005 has been segmented into a right foot cluster 5101 and a left foot cluster 5102; and further noise has been removed from each cluster 5101 and 5102 at step 4905.

Prior to step 4906, the orientation of ground plane 5104 has not yet been determined. An exemplary orientation is represented by arrow 5103 in FIG. 51, which may be a rotational position or azimuth of plane 5104. Having separated the right foot cluster 5101 from the left foot cluster 5102, the one or more processors may determine the orientation of the ground plane 5104 based on clusters 5101 and 5102. For example, at step 4906, the one or more processors may locate a vector 5105 between clusters 5101 and 5102. As shown in FIG. 51, the vector 5105 may point substantially in "y" direction 5002. To locate vector 5105, the one or more processors may estimate an orientation of each cluster 5101 and 5102, and calculate the orientation of vector 5105 by averaging of the estimated orientations of clusters 5101 and 5102. Once the orientation of plane 5104 has been determined, the one or more processors may transform the point cloud (e.g., rotationally) so that the vector 5105 does point in the "y" direction of second axis 5001 (FIG. 50).

To estimate the orientation of clusters 5101 and 5102, the one or more processors may project their respective points onto ground plane 5104, and perform a principal component analysis to identify the major axes of each cluster, and a vector perpendicular to the major axes. The orientation of the major axes may be averaged to locate vector 5105. In some aspects, the one or more processors may use the vertical perpendicular to reduce processing power requirements by cutting the cloud in half. For example, the cloud may be cut into a front half including the toes, and a rear half including the leg portions. In this example, the front half may have a lower number of "z" values (i.e., vertical values) because it does not include the leg portions, making the front half easier to process.

FIG. 52

Figure 52:
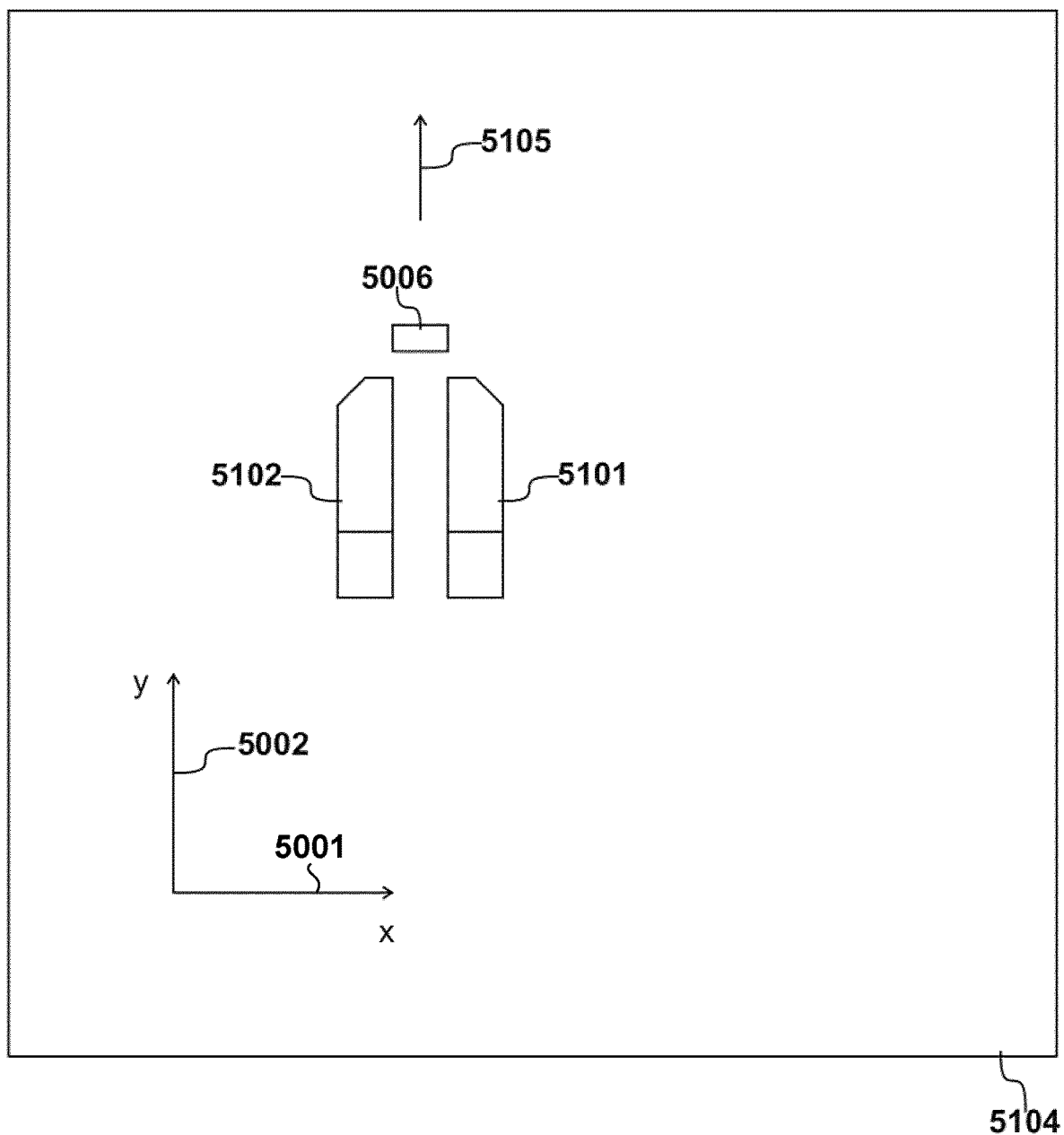
FIG. 52 illustrates an exemplary plan view of the clusters identified in FIG. 40.

A plan view of three-dimensional space 5007 is depicted in FIG. 52 as including ground plane 5104, left foot cluster 5101, right foot cluster 5102, and scaling object cluster 5006. As shown, clusters 5101 and 5102 have been aligned with an orientation of three-dimensional space 5007 according to step 4906 described above. For example, clusters 5101 and 5102 may have been rotated within the ground plane 5104 based on vector 5105, which is now pointing in the "y" direction of second axis 5001 (FIG. 50).

FIG. 53

Figure 53:
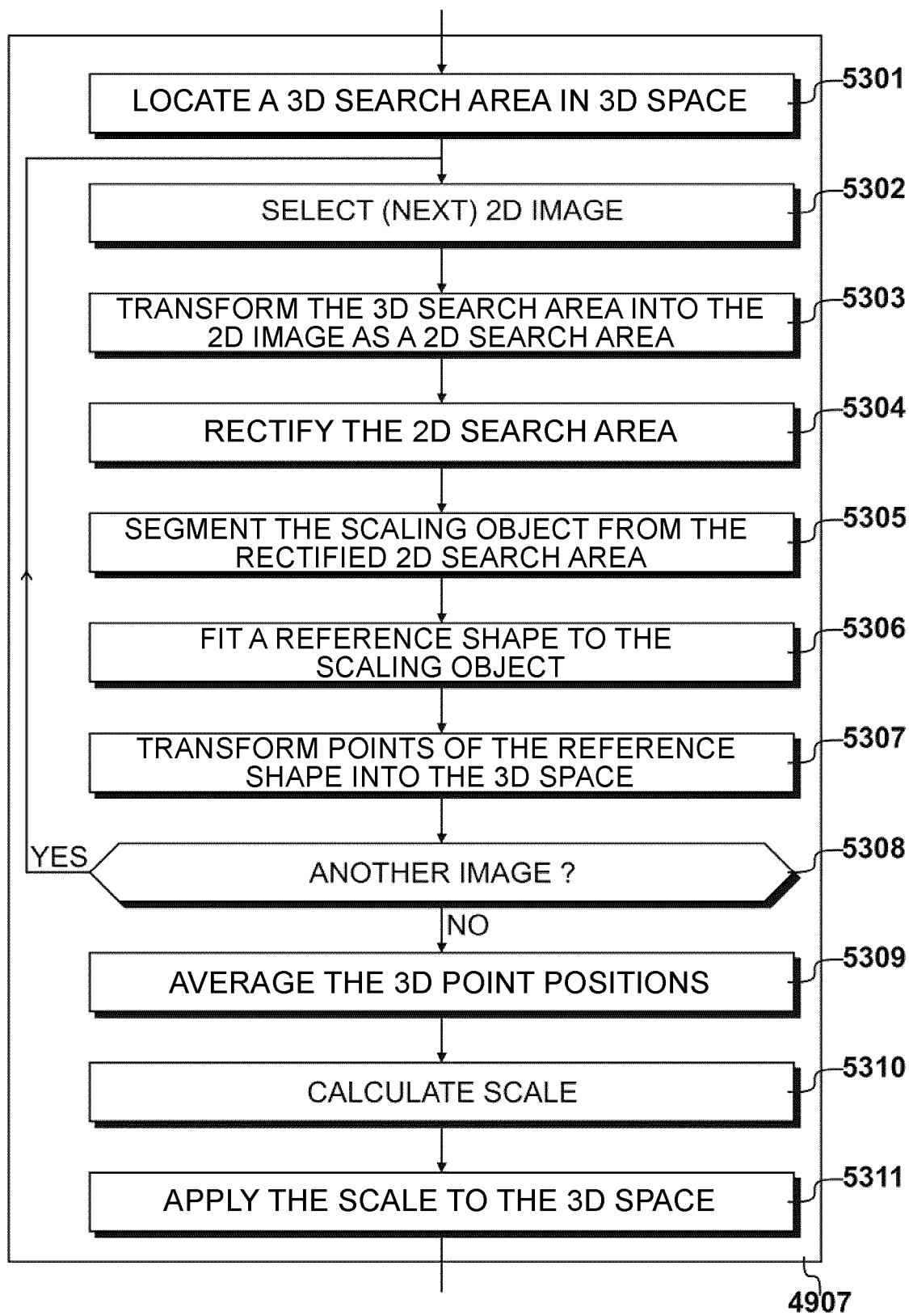
FIG. 53 details exemplary procedures for calculating a scale of the three-dimensional space identified in FIG. 50.
Figure 54:
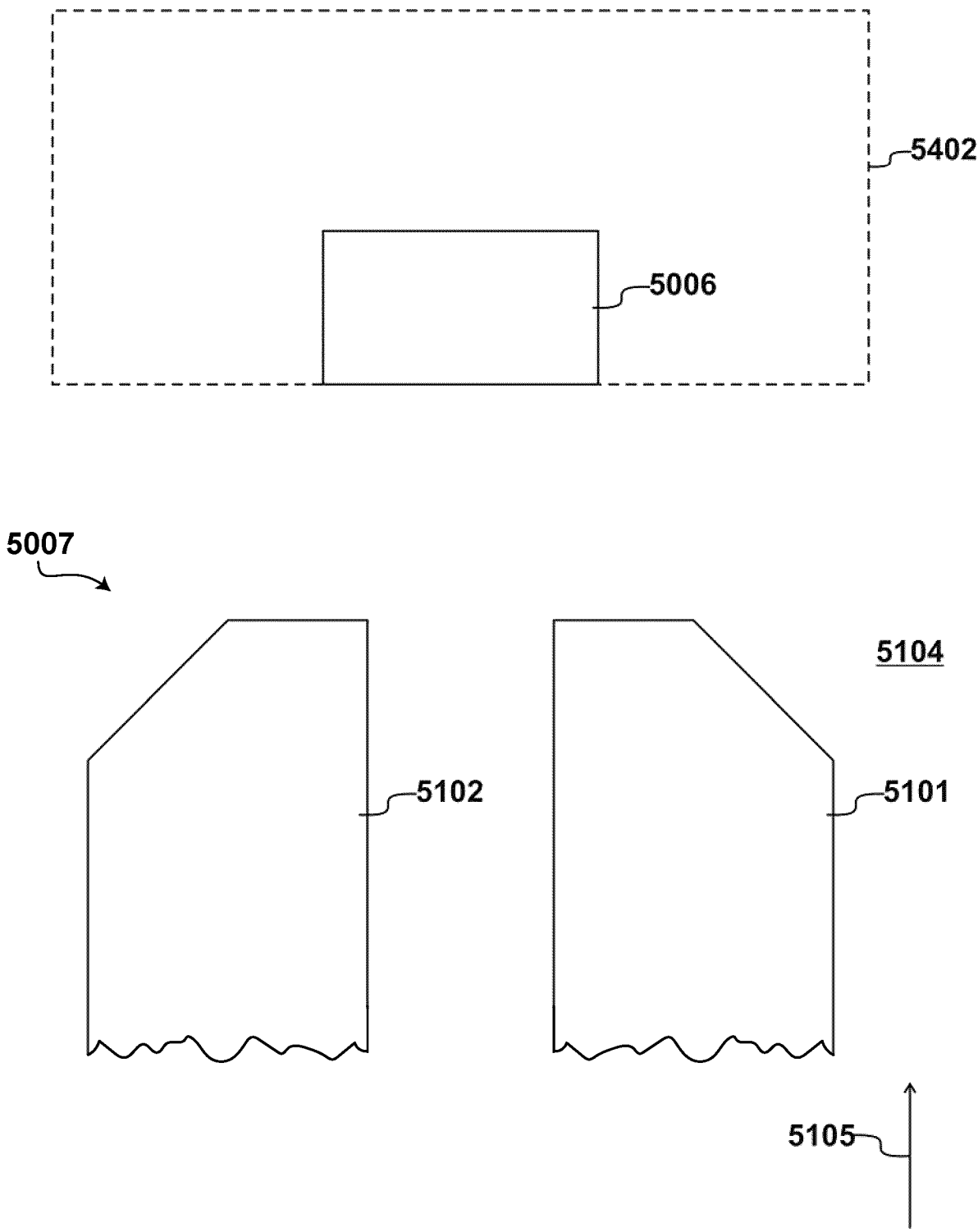
FIG. 54 shows an enlarged view of an exemplary two-dimensional ground plane identified in FIG. 51.
Figure 55:
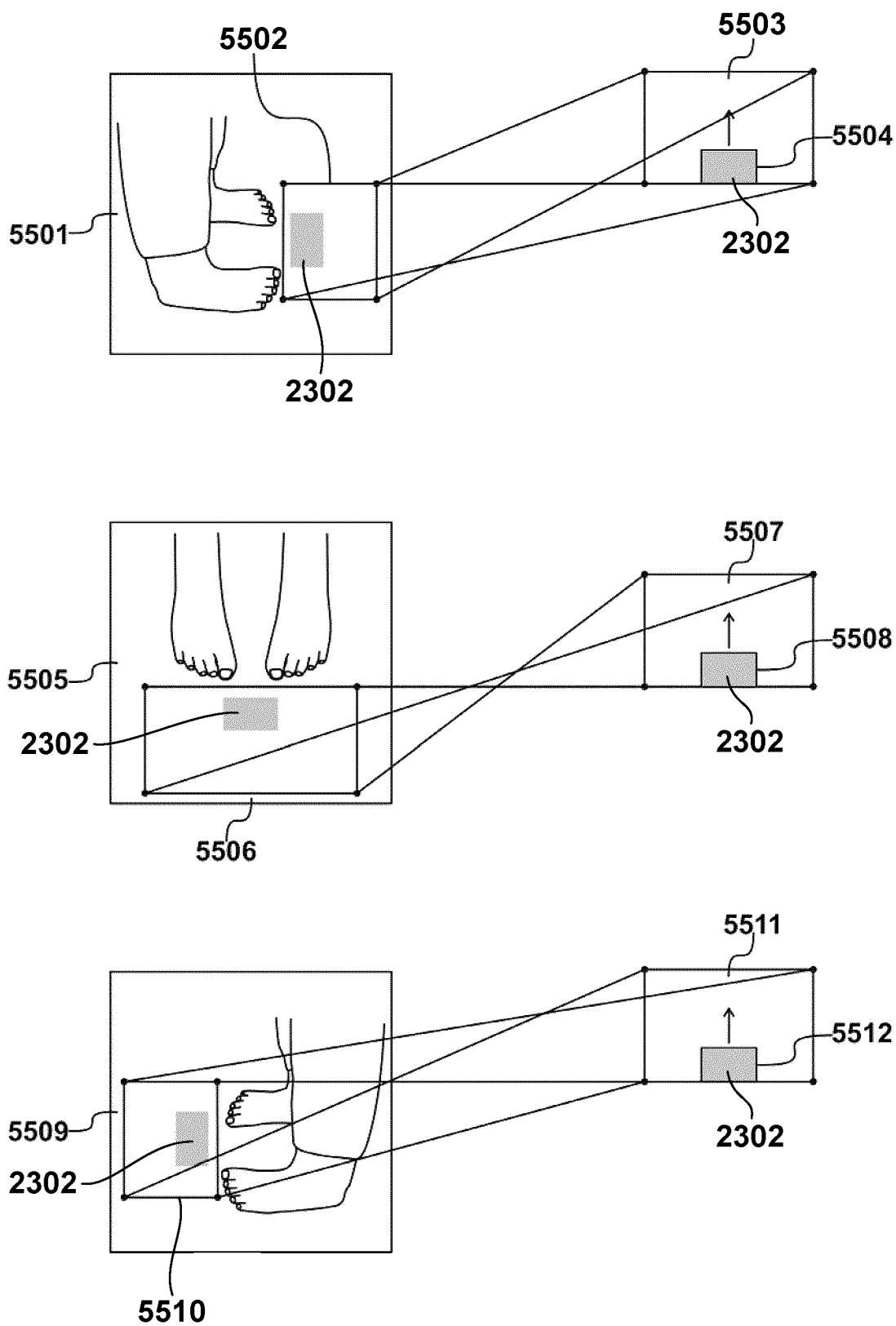
FIG. 55 shows an exemplary rectification of a scaling object in a plurality of two-dimensional images.

Exemplary aspects of step 4907 (FIG. 49) for calculating a scale of three-dimensional space 5007 based on a scaling object (e.g., scaling object 2302 of FIG. 23) are detailed in FIGS. 53 through 55. As a digital representation, numerical values may be added to the three-dimensional space 5007 to define locations in the space 5007. Prior to step 4907, these numerical values may not be scaled. For example, the three-dimensional space 5007 may represent a volume, and the volume may be divided into individual voxels, yet the actual size of each voxel may be unknown to the one or more processors. The scaling operations now described may be performed at step 4907 may resolve this issue.

At step 5301, the one or more processors may determine an approximate location of a three-dimensional search area 5402 of the three-dimensional space 5007. Additional aspects of locating the three-dimensional search area 5402 are described below with reference to FIG. 54.

At step 5302, the one or more processors may select a first two-dimensional image, such as the exemplary captured image 5501 shown at top in FIG. 55, which may have been captured at the start of a sweeping motion, similar to image 2301 of FIG. 24. The processors may determine a scale for the three-dimensional space 5007 based on the first two-dimensional image 5501. As shown in FIG. 55, and described below, steps 5302 through 5307 may be repeated in subsequent iterations of step 4907 so that a more accurate scale may be determined by the one or more processors based on a plurality of two-dimensional images selected at step 5302.

At step 5303, the one or more processors may transform the approximate location of the three-dimensional search area 5402 into the first two-dimensional image 5501. For example, procedures 4002 for generating the three-dimensional space 5007 from two-dimensional images may result in the derivation of a transform; and the processors may use transform to identify the approximate location of the three-dimensional search area 5402 in first two-dimensional image 5501 as a first two-dimensional search area 5502. As shown in FIG. 55, the scaling object 2302 may be located in first search area 5502.

At step 5304, the one or more processors may rectify the first two-dimensional search area 5502 to align with the first two-dimensional image 5501. For example, as shown in FIG. 55, the first image 5501 may have been taken from a non-top-down perspective. Accordingly, the two-dimensional search area 5502 may be rotated about one or more axes by the one or more processors at step 5304 so that the first two-dimensional search area 5402 achieves a top-down alignment with first two-dimensional image 5501, resulting in a first rectified search area 5503.

At step 5305, the one or more processors may segment the scaling object 2302 from the first rectified search area 5503. The segmentation may be performed with various graph-based methodologies based on contextual awareness. For example, at step 5305, the one or more processors may determine whether each pixel in the first rectified search area 5503 is a background pixel or a foreground pixel, and segment the scaling object 2302 from the first rectified search area 5503 based on the foreground/background determination.

A visual characteristic of the scaling-object 2302 may be applied to emphasise the background/foreground distinction. For example, the one or more processors may identify a background colour of the first two-dimensional image 5501 (e.g., white or other colour), assume that the rest of the first image 5501 is a similar colour, and set a border of the first rectified search area 5503 to the background colour, allowing the scaling object 2302 to be segmented from the first rectified search area 5303. In this example, the one or processors may identify the scaling object 2302 because it does not include the background colour. Additional steps may be required if the colours of the scaling object 2302 are similar to the colours of the background. As shown in FIGS. 24, 27, and 31, for example, the scaling object 2302 may be located on an optional sheet of paper 2301 (e.g., a white background) so that processors may use the contrast between object 2302 and paper 2301 to aid the foreground/background determination.

At step 5306, the one or more processors may fit a reference shape to the scaling object 2302. As shown at top right in FIG. 55, for example, the reference shape may be a first quadrilateral shape 5504 (e.g., a rectangle), and the processors may fit the first quadrilateral shape 5504 to exterior edges of the scaling-object 2302 based on the foreground/background determination. Any type of reference shape corresponding with scaling object 2302 may be used.

Step 5306 may comprise additional measurement and verification steps. For example, at step 5306, the processors may fit a plurality of reference shapes around of plurality of potential scaling objects 2302. To maintain accuracy, the processors may determine an aspect ratio of each reference shape, compare the determined aspect ratio to a known aspect ratio of scaling object 2302, and reject any reference shapes having the wrong aspect ratio. For example, the processors may determine an aspect ratio of the first quadrilateral shape 5504, compare the aspect ratio to a known aspect ratio of the scaling object 2302, and accept or reject the shape 5504 based on the comparison. Similar processes may be used for other types of reference shape. If none of the reference shapes have the correct aspect ratio, then the processors may reject the first two-dimensional image 5501.

In keeping with previous examples, at step 5307, the one or more processors may transform points of the first quadrilateral shape 5504 into vertices in the three-dimensional space 5007. For example, the first quadrilateral shape 5504 of FIG. 55 has four two-dimensional corner points, and the processors may locate each two-dimensional corner point in three-dimensional space 5007 as a three-dimensional corner point by intersecting a corresponding three-dimensional ray with ground plane 5104 (FIG. 54). Once step 5307 is complete, a position of each three-dimensional corner point of quadrilateral shape 5504 may have been located in the three-dimensional space 5007. Here again, similar processes may be used for other types of reference shape.

At step 5308, the one or more processors may determine whether another two-dimensional image is to be considered. If this question is answered in the affirmative, then the processors may return to step 5302, select the next image, and repeat the steps 5303 to 5307, as depicted in FIG. 55 and described below.

At step 5309, the one or more processors may average the positions of the three-dimensional corner points located in the three-dimensional space 5007 during step 5307. As described below, for example, the position of each three-dimensional corner point of the first, second, and third quadrilateral shapes 5504, 5508, and 5512 may be averaged to calculate four averaged three-dimensional corner point positions.

At step 5310, the one or more processors may calculate an average scale for the three-dimensional space 5007 based on the four averaged three-dimensional corner point positions. Because of the averaging process, the average scale calculated at step 5310 may be more accurate than a calculation of scale based on a single use of scaling object 2302 from a single two-dimensional image, such as the first two-dimensional image 5501. For example, the non-top-down perspective of scaling object 2302 in first image 5501 may cause distortions that would otherwise reduce the accuracy of the scale. However slight, these reductions may affect the accuracy of any evaluations based on upon the three-dimensional space 5007, and may be avoided by the average process of step 5309.

At step 5311, the one or more processors may apply the average scale calculated at step 5310 to three-dimensional space 5007, allowing subsequent evaluations to be made directly from space 5007.

FIG. 54

Additional aspects of step 5301 of step 4907 (FIG. 49) are detailed in FIG. 54, which includes an enlarged view of the two-dimensional ground plane 5104 of three-dimensional space 5007. In FIG. 54, for example, a preliminary segmentation may have been performed to produce right foot cluster 5101 and left foot cluster 5102; and the clusters 5101 and 5102 may have been aligned with an orientation of three-dimensional space 5007 according to step 4906 described above. As shown, clusters 5101 and 5102 have been aligned in ground plane 5104 with vector 5105.

At step 5301, the one or more processors may determine an approximate location of the three-dimensional search area 5402 in the three-dimensional space 5007 based on vector 5105. In keep with above examples, the approximate location may be determined by locating the three-dimensional search area 5402 relative to clusters 5101 and 5102. For example, the one or more processors may locate search area 5402 by: searching the three-dimensional space 5007 to identify the toes (e.g., based on foot features, such as the shape of the feet); moving forward in the "y" direction of vector 5105 a predetermined distance from the identified toes; and locating the three-dimensional search area 5402 within ground plane 5104 at the target area or position.

Accordingly, the three-dimensional search area 5402 may be located in the ground plane 5104 by the one or more processors so that the resulting two dimensional search area 5502 is likely to surround the scaling object 2302 in the first two-dimensional image 5501. For example, the one or more processors may instruct the recipient to locate the scaling object 2302 in front of the feet, allowing the processors to locate the three-dimensional search area 5402 by moving forward from the toes, in the "y" direction of vector 5105, a distance that is: equal to a length of clusters 5101 and 5102; and/or no nearer than a half a length from a centre of clusters 5101 and 5013 (e.g., no nearer than the tips of the toes).

In keeping with above examples, the actual size of scaling object 2302 may be known, and may be approximate to the size of a standard credit card. Accordingly, because of step 5301, at least one object may exist within the resulting two-dimensional search area of each two-dimensional image selected at step 5302 for which the actual size, based on physical measurements in the real world, may be known to the processors.

FIG. 55

Additional aspects of step 4907 are depicted in FIG. 55, which details calculating the scale based on multiple iterations. As shown, steps 5302 through 5307 may be repeated during each iteration.

In keeping with above examples, the one or more processors may select the first two-dimensional image 5501 at a first iteration of step 5302. As shown in FIG. 55, for example, the first image 5501 may have been captured at or near the start of a sweeping motion, similar to image 2301 of FIG. 24. On a second iteration of step 5302, the processors may select a second two-dimensional image 5505. As shown, the second image 5505 may have been selected at or near a midway point of the sweeping motion, similar to image 2301 of FIG. 27. On a third iteration of step 5302, the processors may select a third two-dimensional image 5509, shown in FIG. 55 as being selected at or near the end of the sweeping motion, similar to image 2301 of FIG. 31. The processors may perform these (and possibly other) iterations in order to improve the accuracy of the scale of the three-dimensional space 5007. Any number of iterations may be similarly performed.

At the first iteration of step 5303, the one or more processors may transform the three-dimensional search area 5402 (FIG. 54) into the first two-dimensional image 5501 to identify the first two-dimensional search area 5502. At the second iteration, the three-dimensional search area 5402 may be transformed into the second two dimensional image 5505 to identify a second two-dimensional search area 5506. And at the third iteration, search area 5402 may be transformed into the third two dimensional image 5509 to identify a third two-dimensional search area 5510.

At the first iteration of step 5304, the one or more processors may rectify the first two-dimensional search area 5502, resulting in the first rectified search area 5503. At the second iteration, the second two-dimensional search area 5506 of second image 5505 may be rectified, resulting in a second rectified search area 5507. And at the third iteration, the third two-dimensional search area 5510 of third image 5509 may be rectified, resulting in a third rectified search area 5511.

At the first iteration of step 5305, the one or more processors may segment the scaling object 2302 from the first rectified search area 5503. At the second iteration, the scaling object 2302 may be segmented from the second rectified search area 5507. And at the third iteration, the scaling object 2302 may be segmented from the third rectified search area 5511.

At the first iteration of step 5306, the one or more processors may fit the first quadrilateral shape 5504 (or other reference shape) to the scaling object 2302. At the second iteration, a second quadrilateral shape 5508 may be fit to the scaling object 2302. And at the third iteration, a third quadrilateral shape 5512 may be fit to the scaling object 2302.

At the first iteration of step 5307, the one or more processors may locate the two-dimensional corner points of the first quadrilateral shape 5504 in the three-dimensional space 5007 as a first set of three-dimensional corner points. At the second iteration, the two-dimensional corner points of the second quadrilateral shape 5508 may be located in space 5007 as a second set of three-dimensional corner points. And at the third iteration, the two-dimensional corner points of third quadrilateral shape 5512 may be located in space 5007 as a third set of three-dimensional corner points.

In this example, after the third iteration, the one or more processors may answer the question asked at step 5308 in the negative. At this point, a plurality of points may have been located in space 5007, including the first set of three-dimensional corner points from the first quadrilateral shape 5504, the second set of corner points from the second quadrilateral shape 5508, and the third set of corner points from the third shape 5512. Accordingly, at step 5309, the one or more processors may average the position of each three-dimensional corner point of the aforementioned first, second, and third sets, resulting in four averaged three-dimensional corner point positions.

At step 5310, the one or more processors may calculate an average scale for the three-dimensional space 5007 based on the four averaged corner point positions. While three iterations are shown in FIG. 55, and described above, any number of iterations may be performed to calculate the average scale prior to application in step 5311.

FIG. 56

In some aspects, when considering point clouds or clusters in three-dimensional space 5007 (e.g., as shown in FIG. 52), it may only be possible for the one or more processors to consider their sizes with respect to digital indications. As described above, prior to determining a scale for space 5007, these digital indications may or may not provide any real-world scaling information. After performing step 4907 (FIGS. 49 and 53 through 55), the processors may scale the digital indications so that the actual sizes of the point clouds may be determined.

Figure 56:
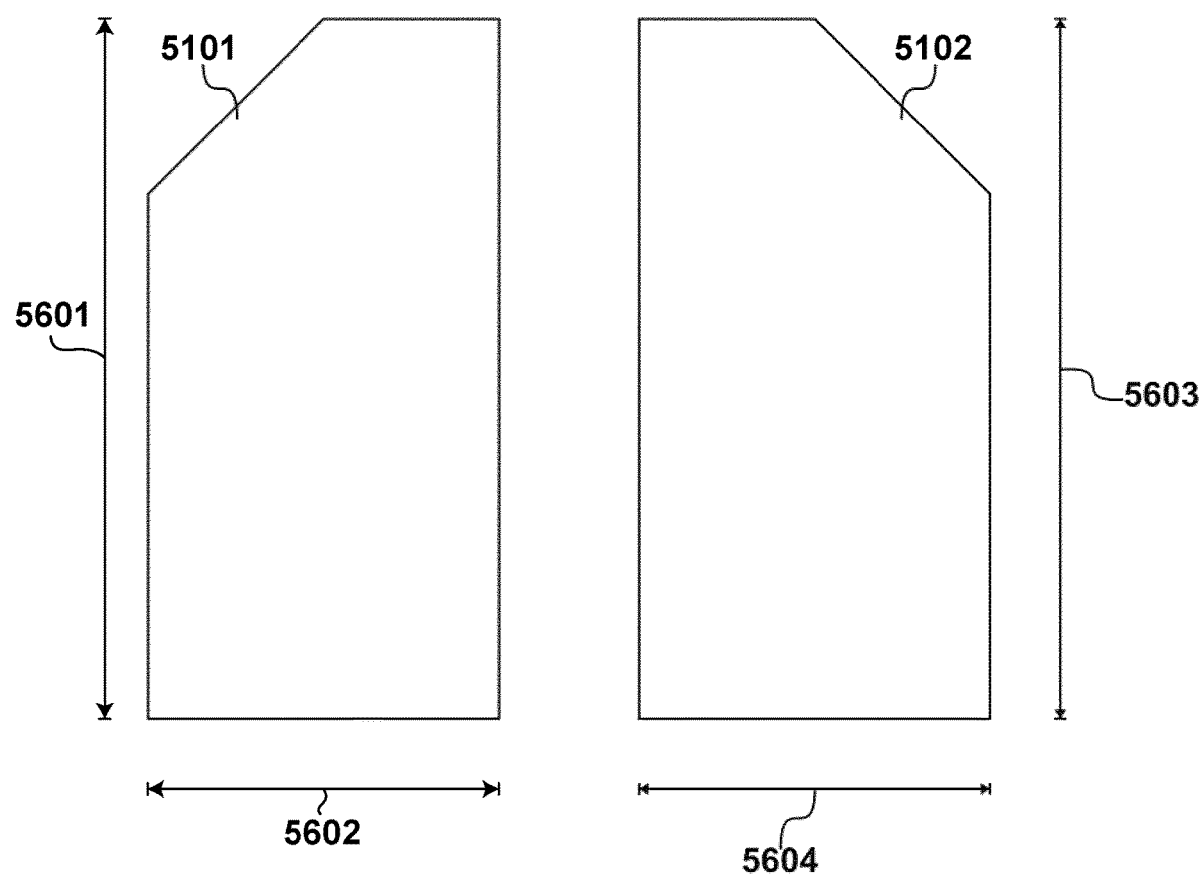
FIG. 56 shows examples of a scaled left foot cluster and a scaled right foot cluster of the type identified in FIG. 52.

Another example of three-dimensional space 5007 is shown in FIG. 56, which depicts a plan view left foot cluster 5101 and right foot cluster 5102 after being segmented and aligned according to the processes described above. Within three-dimensional space 5007, the one or more processors may assess a plurality of digital indications. As shown in FIG. 56, the digital indication may include a length indication 5601 and a width indication 5602 for cluster 5101, and a length indication 5603 and a width indication 5604 for cluster 5102. Furthermore, because of the processes shown in FIGS. 53 and 55, the one or more processors may scale indications 5601 to 5604 to determine evaluations that are scaled to, say, millimetre accuracy.

However, given that the scale of the three-dimensional space 5007 has been determined, it has been appreciated that a more accurate separation of the feet from the floor may be achieved with the one or more processors based on the determined scale. For example, an exemplary step 4106 for segmenting the point cloud is detailed in FIG. 48 as including further steps 4801 and 4802. As described above, the one or more processors may perform a first segmentation at step 4801 to determine a scale of the point cloud. At step 4802, after determining the scale, the one or more processors may repeat aspects of the segmentation process in order to separate the feet with reference to the newly derived scale.

FIG. 57

Figure 57:
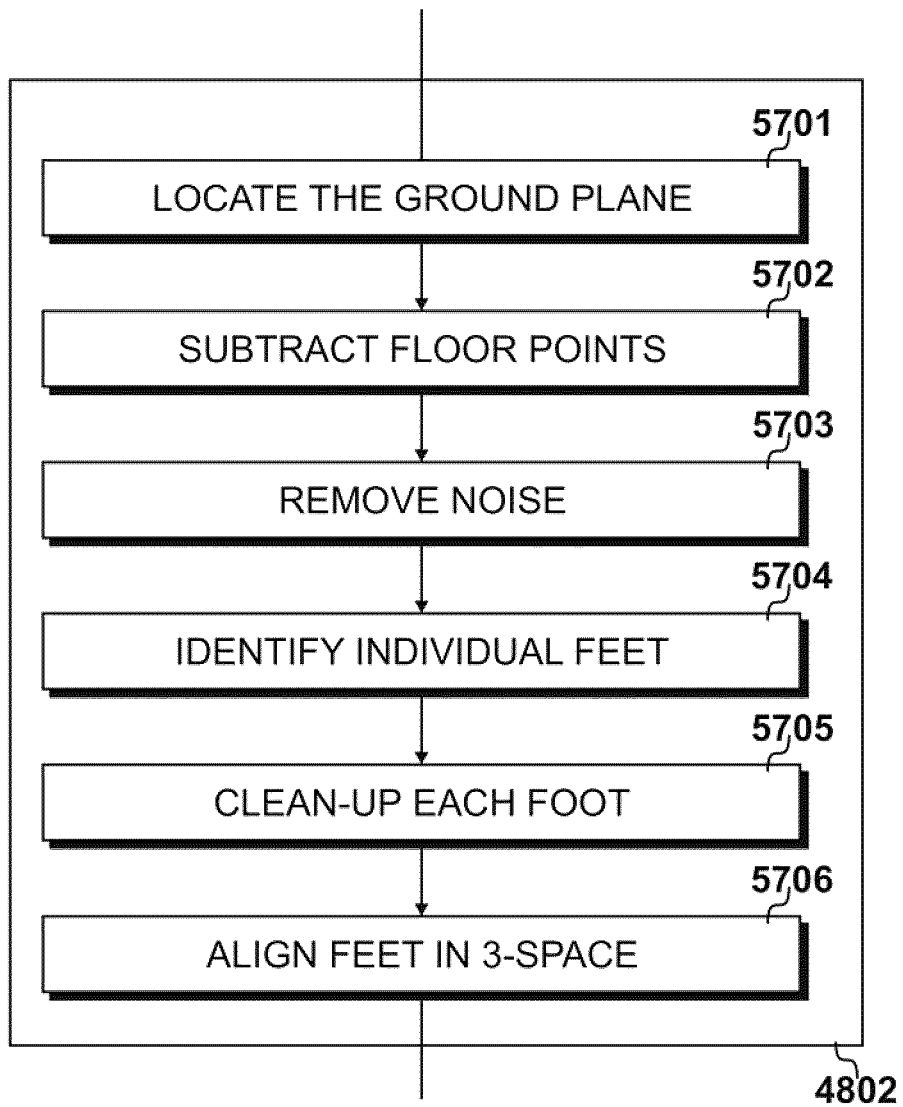
FIG. 57 illustrates exemplary procedures for separating the left foot and right foot clusters with reference to a determined scale.

An exemplary step 4802 for separating the feet clusters with the determined scale is detailed in FIG. 57.

At step 4901 described above, the one or more processors may have provisionally located ground plane 5104 based on an offset distance 5009. As shown in FIG. 50, offset distance 5009 may be provisionally determined as a proportion of a vector 5008, and used to locate ground plane 5104. A similar process may be performed at step 5701 with reference to the determined scale of three-dimensional space 5007.

For example, at step 5701, the one or more processors may locate the ground plane 5104 (e.g., FIG. 51) in the three-dimensional space 5007. As before, plane 5104 may define the interface between clusters 5101 and 5102 and a ground cluster; as in FIG. 50, in which plane 5104 defines an interface between ground cluster 5004 and foot cluster 5005.

At step 5702, the one or more processors may subtract the floor points from ground plane 5104. As described above with reference to FIGS. 49 and 50, a predetermined proportion of space 5007 (e.g., based on vector 5008) may have been used to subtract the floor points. At step 5702, now that the scale has been determined, the one or processors may specify a separation region based on real-world measurements. For example, a predetermined separation region (e.g., approximately three millimetres) may be specified by the processors at step 5702 as an alternative to determining offset distance 5009 based on vector 5008. Because it is based on real-world measurements, this approach may provide greater separation accuracy.

At step 5703, the one or more processors may perform a first clean-up process to remove noise from the three-dimensional point cloud. The first clean-up process performed at step 5703 may be similar to the first clean-up process performed at step 4903 above. For example, the first clean-up process at step 5703 may similarly comprise identifying points that are significantly displaced from the foot points, and removing the identified points from the clouds. As before, the maximum amount of displacement may vary and/or be specified by the one or more processors. At step 5703, the maximum displacement may be specific based on the real-world measurements (e.g., about one millimetre or less).

At step 5704, the one or more processors may identify the left foot cluster 5101 and right foot cluster 5102. In some aspects, for example, step 5704 may comprise performing additional segmentation processes on each cluster of points, similar to step 4904 above.

At step 5705, the one or more processors may perform a second clean-up process to remove noise from each of clusters 5101 and 5102 after being identified at step 5704. The second clean-up process at step 5705 may be similar to the second clean-up process at step 4905 above. For example, the second clean-up process may similarly comprise identifying points that are significantly displaced from clusters 5101 and 5102, and removing the identified points from the clusters.

At step 5706, the one or more processors may align the respective left foot and right foot clusters 5101 and 5102 with an orientation of three-dimensional space 5007. For example, step 5706 may comprise repeating aspects of step 4906 described above.

FIG. 58

Figure 58:
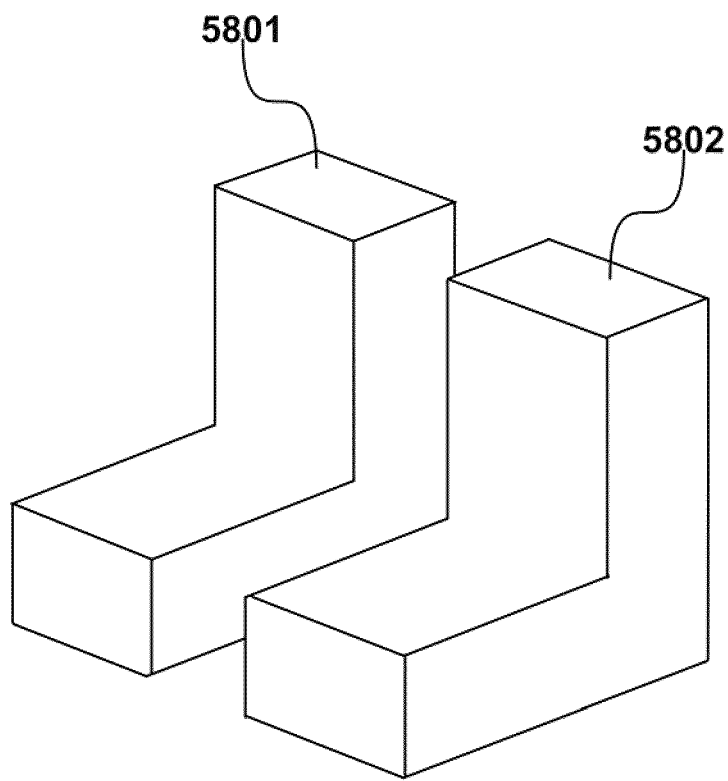
FIG. 58 illustrates examples of left foot and right foot clusters separated following the procedures identified in FIG. 57.

After performing the procedures detailed in FIG. 57, the one or more processors may have further refined the left foot cluster 5101 and right foot cluster 5102 by identifying a more-distinct cluster of points for the right foot, and a more-distinct cluster of points for the left foot. From these more-distinct clusters, the processors may establish a new right foot cluster 5801 and a new left foot cluster 5802, examples of which are depicted in FIG. 58. As described herein, three forms of three-dimensional representations may be established. Firstly, a sparse point cloud may be determined by the one or more processors based on camera positions. For example, each of the new foot clusters 5801 and 5802 shown in FIG. 58 may be considered a sparse point cloud. Additional procedures may be performed on the sparse point clouds by the processors to generate dense point clouds therefrom. Thereafter, the processors may fit a three-dimensional mesh to the dense point clouds to establish a complete three-dimensional surface.

FIG. 59

In some aspects, the one or more process may generate the dense point cloud by performing a multiple-stereo view process, in which the one or more processors generate a dense three-dimensional reconstruction of each point cloud. For example, this process may comprise generating a dense three-dimensional reconstruction for each of the new foot clusters 5801 and 5802 shown in FIG. 58.

In some aspects, gaps may be present within the dense reconstructions. The one or more processors may resolve these gaps by fitting a three-dimensional mesh over each dense reconstruction. An example is shown FIG. 59, in which an exemplary three-dimensional mesh 5901 has been fitted to the new right foot cluster 5801. Any process may be used to fit mesh 5901 to cluster 5801, including those described below. Although not shown in FIG. 59, a similar mesh may be fitted to the new left-right cluster 5802 using similar processes.

Figure 59:
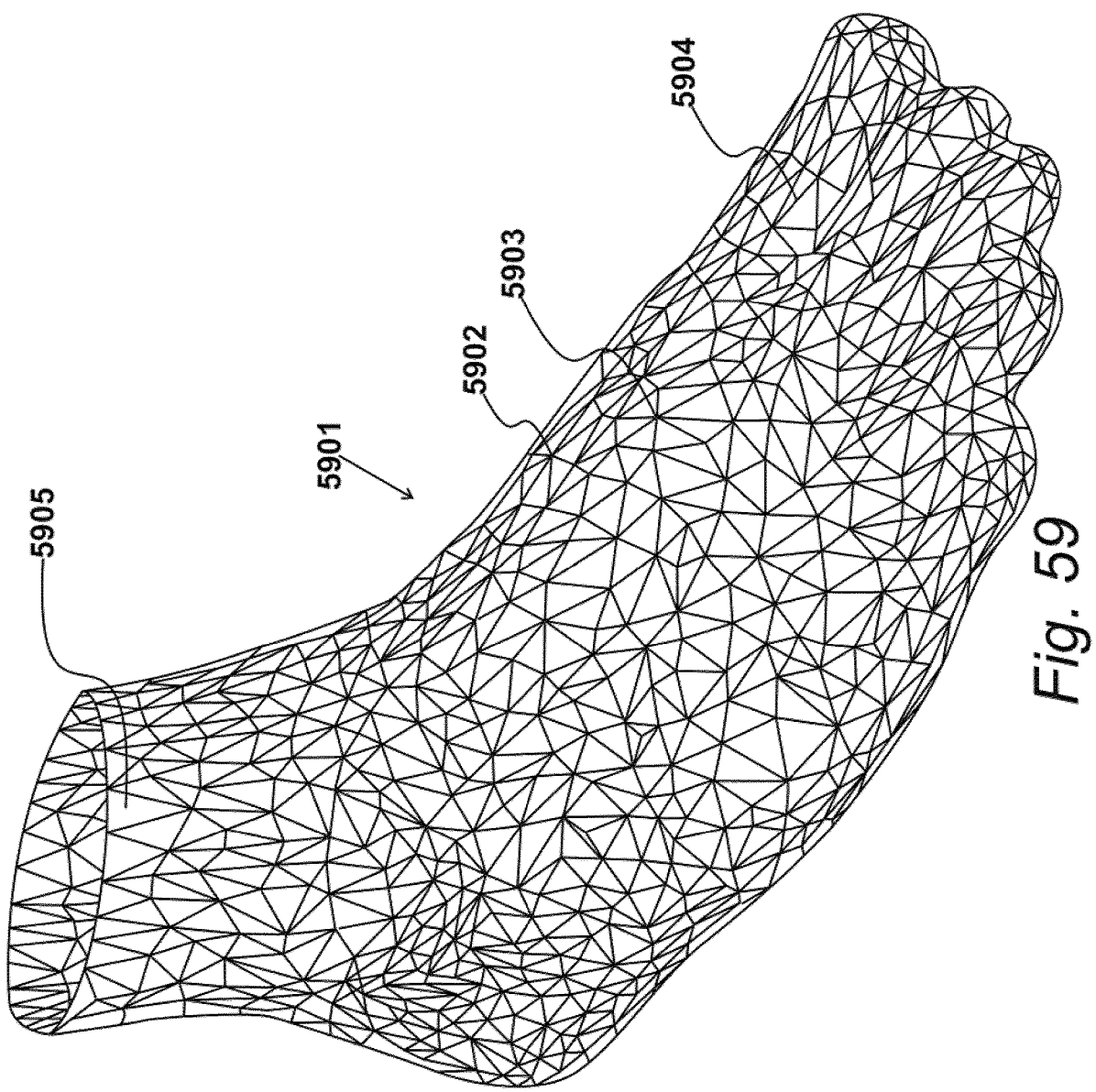
FIG. 59 illustrates an exemplary three-dimensional mesh for modelling a foot defined by a point cluster.

As shown in FIG. 59, the three-dimensional mesh 5901 may comprise a collection of vertices, including first vertex 5902 and a second vertex 5903. In this example, vertex 5902 and 5903 may be connected by edges, such as edge 5904. Mesh 5901 may comprise multiple connections of this type, forming triangular surfaces, such as triangular surface 5905 of FIG. 59. For example, the overall shape of an exterior surface of mesh 5901 may be tessellated with triangles, and the corner of each triangle may be defined by a vertex in three-dimensional space. In this example, the one or more processors may fit the mesh 5901 by iteratively moving the positions of these vertices in order to bring the exterior surface of mesh 5901 into a position where it closely surrounds each point within the new right foot cluster 5801. In some aspects, the one or more processors may perform the iteration on a loop alternating between an as-rigid-as-possible deformation followed by an iterative-closest-point procedure to supply constraints.

In addition to adopting the shape defined by a respective cluster, the one or more processors may use the exterior surface of three-dimensional mesh 5901 to fill in any gaps that were left incomplete by the dense-reconstruction process by, for example, utilizing the rigid-as-possible approach to maintain a realistic organic shape for mesh 5901.

FIG. 60

Figure 60:
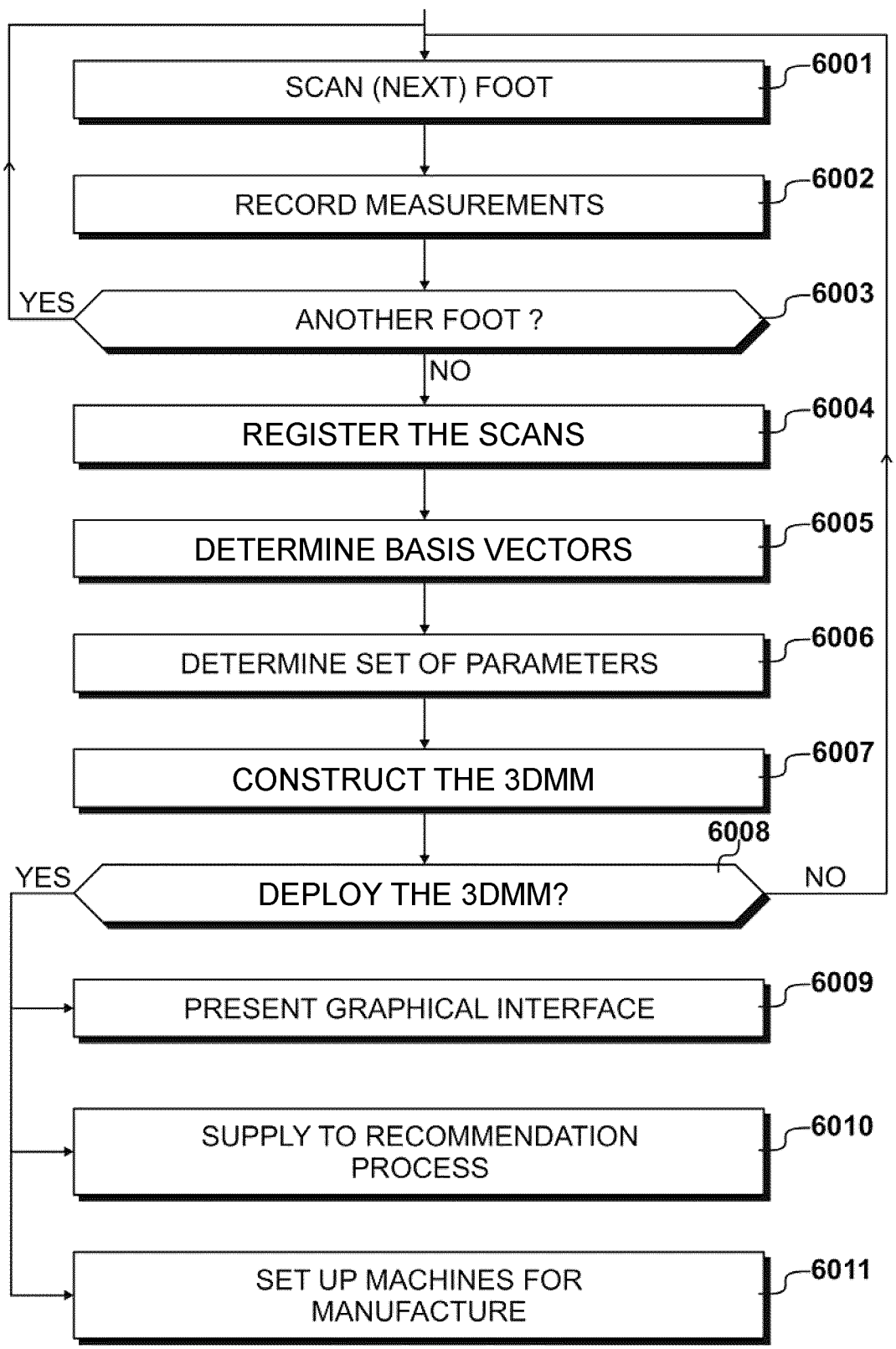
FIG. 60 details exemplary procedures for preparing a three-dimensional morphable model.

Exemplary processes for developing a three-dimensional morphable model (or "3DMM") of feet are now described with reference to FIG. 60. In sum, these processes may allow the one or more processors to determine a set of basis vectors (or shape components) offline based on a data set of observed shapes so that any new shape can be represented as a linear combination of these basis vectors using the following equation:

$$newShape = meanShape + sum\_i = 1 \ldots N$$
$$parameter\_i * shapeComponent\_i$$

Wherein: "parameter_i" is the i-th weighting, a scalar; "shapeComponent_i" is the i-th basis vector; and "MeanShape" is a vector containing the average of the input shapes. For a given shape, the one or more processors may project the shape into the basis vectors to compute the weightings (or foot parameters) according to the following equation:

$$parameter\_i = dotProduct[(someShape - meanShape), shapeComponent\_i]$$

Other types of decomposition and encoding also may be used. For example, sparse coding may be used to solve an optimisation to get the parameters rather than straight projection (dot product). The reconstructions may be linear or nonlinear. For example, one reconstruction may be nonlinear, such a kernel PCA.

Steps 6001 through 6003 may be used to collect scan data. For example, at step 6001, an exemplar foot may be scanned using a three-dimensional scanner, from which measurements may be recorded at step 6002. A question is asked at step 6003 as to whether another foot is to be scanned; and, when answered in the affirmative, the scanning process at step 6001 may be repeated. The one or more processors may be used to perform steps 6001 to 6003, using any technology for recording and three-dimensional scanning.

Many exemplar feet may be scanned and recorded by the one or more processors at steps 6001 and 6002. Additional steps may be performed by the processors to determine differences between each exemplar foot, and produce a set of axes that allow changes to be made from one exemplar foot to another. For example, during step 6002, the one or more processors may perform a principal component analysis of each exemplary foot; record the results together with any associated measurements; and identify from the results any first portions of 3DMM that change, and any second portions of the 3DMM that do not change.

In this example, the presence of a point in three-dimensional space 5007 that is difficult to accommodate (and possibly impossible to accommodate) by adapting allowed variable parameters only, may be rejected by the processors as an example of noise. Accordingly, various procedures for noise removal may be enhanced by performing steps 6001 to 6003. Furthermore, the number of iterations required to converge upon a solution may be reduced by incorporating the constraints of actual feet, rather than having a general purpose deformable model. Individually and/or together, these effects may reduce processing power requirements.

At step 6004, the one or more processors may register the 3D scans collected with steps 6001 through 6003. The input to step 6004 may be a set of 3D scans of feet. Each 3D scan may have many 3D points, and a different number. The 3D scans may not be in correspondence; such that, for a given point in a first scan, the processors may not know which point it corresponds to in second scan. A correspondence may not be possible considering that the points may be sampled differently over the foot. Nonetheless, an analysis of shapes may require the one or more processors to determine variations of the same point across all of the 3D scans.

Step 6004 may resolve these issues. For example, for each 3D scan, step 6004 may comprise: identifying a fixed template mesh; and deforming it to the fit the 3D scan, resulting in a deformed mesh for each 3D scan. In this example, the number of vertices in the template mesh may be N, and the fixed template mesh may be of any type, such as an artistic model and/or a model computed from data. Accordingly, each point on the registered scans may now correspond to the same location on the foot in each scan; and each registered scan may be a deformed mesh with N points.

At step 6005, the processors may determine the basis vectors based on the registered scans. The mesh edge connectivity may be the same for all scans, and of no use in assessing shape variations, meaning that it may discarded by the one or more processors at step 6005. The result is N 3D points per registered scan. For example, these points may be concatenated into a 1-D vector of length 3*N as follows:

[x1 y1 z1 x2 y2 z2 x3 y3 z3 . . . xN yN zN]

Accordingly, given the fixed edge connectivity, the one or more processors may translate foot shapes between a vector representation, a point cloud representation, and a mesh representation.

One way of modelling the distribution is to find basis vectors that span the foot subspace. Any modelling method may be used, such as principal components analysis ("PCA"), independent component analysis ("ICA"), sparse coding, or a combination thereof. For example, ICA may be used on the residual (orthogonal subspace) of the PCA to determine localised shape components as non-zero elements in the basis vectors that correspond to mesh vertices that are adjacent thereto in the mesh. The opposite of a localised component would be a global component affecting all vertices in the mesh. A combination of both may be used so that changes to the scale or width affect the whole foot, and changes to the length of one toe in isolation are localised. For example, PCA may determine the global components, and ICA may determine the complementary localised components.

Step 6006 may be optional. For example, at step 6006, the one or more processors may determine a set of graphical representation parameters based on the basis vectors. In this example, the resulting parameters may be used in optional step 6009 described below.

At step 6007, the processors may construct a 3DMM based on the registered scans. The 3DMM may include a set of basis vectors (or shape components) and a mean (average) shape. Step 6007 may comprise packaging this data together so that, when the model is fitted to a foot shape, or a foot shape is projected onto the model, you get a set of foot parameters (or weights) for that foot shape. The foot parameters may be for a specific foot; and the 3DMM (e.g., the shape components and mean shape) may exist independent of the foot parameters (but not vice versa).

Additional iterations may be performed. For example, in some aspects, the one or more processors may determine at step 6008 whether the 3DMM may be deployed. Various data sufficiency tests may be performed. If for some reason the model is seen as unacceptable based on these tests, then the one or more processors may receive more data by returning to step 6001 and scanning of additional feet.

If the question asked at step 6008 is answered affirmatively, then the one or more processors may deploy the 3DMM. At optional step 6009, the one or more processors may produce a graphical representation of the 3DMM based on the graphical representation parameters from optional step 6006. At step 6010, the processors may supply data including the 3DMM and/or the graphical representation (if optional steps 6006 and 6009 were performed) to recommendation process 310 for further processing.

An optional step 6011 for manufacturing footwear also may be performed. As shown in FIGS. 3 and 60, at step 6011, the one or more processors may supply the data to facilitate the setting up of machines 316 for the manufacture of footwear.

FIG. 61

Aspects of exemplary foot parameters are shown in FIG. 61. In some aspects, the foot parameters determined at step 6006 (FIG. 60) may correspond with foot measurements typically used in the manufacture of lasts, such as those depicted in FIG. 1. Any foot measurements may be used, including any measurements of foot length, foot width, instep height, arch height, and circumference. The foot parameters may include six different parameters. As shown in FIG. 61, for example, these six foot parameters may include a first parameter 6101 (e.g., corresponding with length measurement 101 of FIG. 1); a second parameter 6102 (e.g., corresponding with width measurement 102); a third parameter 6103 (e.g., corresponding with first circumferential measurement 103); a fourth parameter 6104 (e.g., corresponding with second circumferential measurement 104); a fifth parameter 6105 (e.g., corresponding with a third circumferential measurement 105); and a sixth parameter 6106 (e.g., corresponding with fourth circumferential measurement 106).

The one or more processors may use a different set of foot parameters. Any number of foot parameters may be used. For example, this different set may include significantly more foot parameters than shown in FIG. 61, such as twenty or more. The different parameters may or may not correspond with typical foot measurements. For example, by clustering certain values, the one or more processors may generate foot parameters having little or no correspondence with any known foot measurements, including measurements that cannot be performed by hand.

As a further example, each foot parameter may control a weighted distortion of all vertices in 3DMM. Put another way, each foot parameter may be a weighting on a shape component, defined as a perturbation applied to the 3DMM. For example, a shape component affecting foot width may magnify the x-ordinate of all points in the 3DMM, allowing the 3DMM to be reconstructed by adding a (parameter) weighted sum of shape components to the mean shape with the following equation:

$$y = m + \text{sum}\_iw\_i * C\_i$$

wherein: "m" is the mean shape; "w_i" is the "i-th" shape parameter (a scalar); and "C_i" is the "i-th" shape component (vector); and "y" is the reconstructed vector [x y z x y z x y z ...] that may be converted into a 3DMM with a fixed edge structure.

As a further example, the clustering of particular parameter values may facilitate the establishment of setting-up data, generated at optional step 6011, to improve the productivity of the machines for manufacture 316 identified in FIG. 3, by producing footwear having specific measurements that accommodate a greater number of recipients.

FIG. 62

Figure 62:
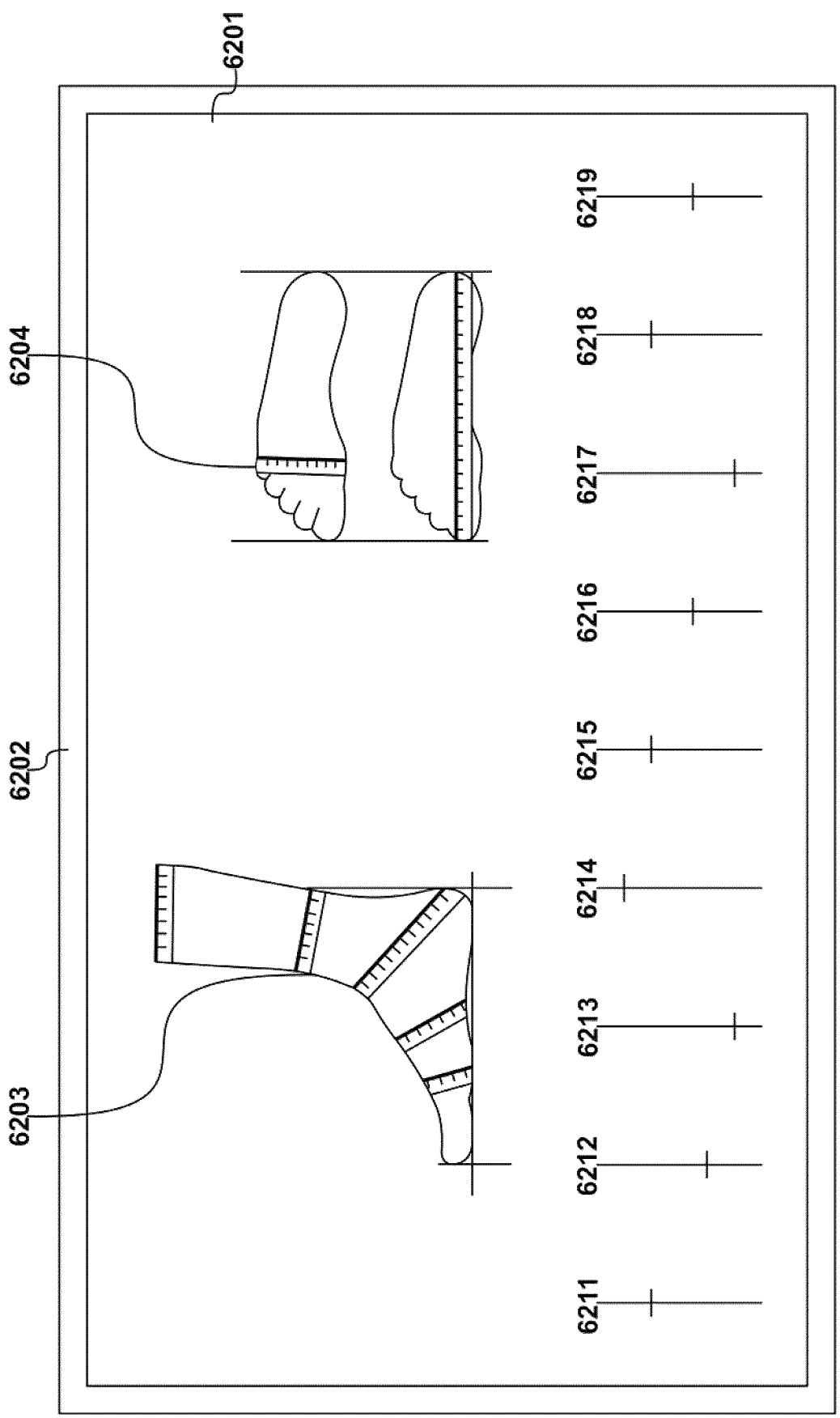
FIG. 62 illustrates an exemplary graphical interface for controlling the foot parameters identified in FIG. 61.

Exemplary aspects of optional step 6009 for producing a graphical representation of the 3DMM are shown in FIG. 62, which depicts a graphical interface 6201. Any configuration for interface 6201 may be used. In this example, the graphical interface 6201 shows a first two-dimensional image 6203 of the 3DMM, and a second two-dimensional image 6204 of the 3DMM. Images 6203 and 6204 may be similar to those identified in FIG. 61. Alternatively, a three-dimensional representation of the 3DMM may be shown in interface 6201. Similarly, interface 6201 may include both two-dimensional representations 6203 and 6204 alongside a three-dimensional representation; and/or a toggle for switching between these two- and three-dimensional representations.

As shown in FIG. 62, graphical interface 6201 may be displayed on a display device 6202 in communication with the one or more processors. Any display technology may be used. For example, display device 6202 may include a touchscreen, similar to display device 402 of apparatus 305.

As described with in more detail with reference to recommendation process 310, the one or more processors may determine a best fit by manipulating the 3DMM based on foot parameters. For example, to assist with the development of suitable 3DMMs and/or permit consideration of numerous input exemplar data, graphical user interface 6201 may allow for manual manipulation of these parameters with the one or more processors. As shown in FIG. 62, interface 6201 may include a plurality of sliders, and the manual manipulations may be achieved by operation of the sliders. Depending upon the capabilities of display device 6202, the sliders may be operated to generate a user input using a stylus, a mouse, or a manual application of a finger upon the slider. In turn, the one or more processors may manipulate one or more of the foot parameters based on the user input.

As shown in FIG. 62, for example, graphical interface 6201 may comprise: a first slider 6211 generating a first user input that controls orientation; a second slider 6212 generating a second user input that controls translation; and a third slider 6213 generating a third user input that controls overall scaling. The first, second, and third user inputs may be generated by operation of the respective first, second, and third sliders 6211, 6212, and 6213. For example, the one or more processors may use a combination of these inputs to locate an un-deformed 3DMM within a displayed space, align the 3DMM with the space, and/or overlay the 3DMM upon point clouds or other, similarly scanned input data.

Graphical interface 6201 may include other sliders for other purposes. As shown in FIG. 62, interface 6201 may include a plurality of additional sliders 6214 to 6219, each of which may be operable to generate a different user input. For example, having moved, positioned, and scaled the 3DMM in response to user inputs generated by operation of sliders 6211 to 6213; the one or more processors may manipulate parameters 6101 to 6106 in response to user inputs generated by operation of sliders 6214 to 6219. Any foot parameters may be manually manipulated in this manner. In some aspects, the sliders 6211 to 6219 may represent all of the adjustments that can be made to the 3DMM with the one or more processors to accommodate the size and shape of an actual foot.

FIG. 63

Figure 63:
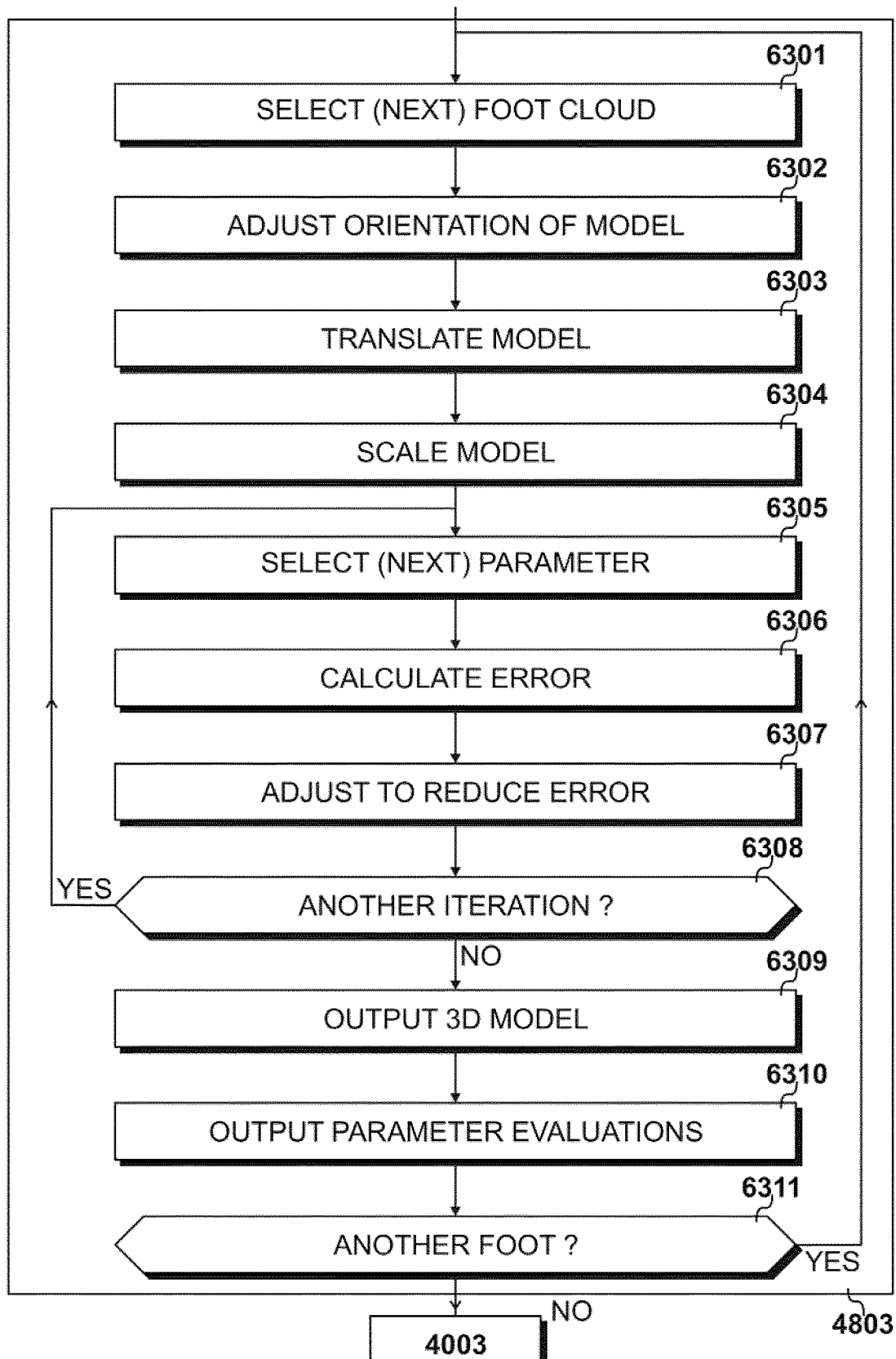
FIG. 63 details exemplary procedures for transforming a three-dimensional surface.

Exemplary procedures 4803 for transforming a three-dimensional surface of a 3DMM are detailed in FIG. 63.

At step 6301, the one or more processors may select a foot cloud. For example, either new right foot cluster 5801 or new left foot cluster 5802 of FIG. 58 may be selected. In the following example, it may be assumed that new right foot cluster 5801 has been selected first.

At step 6302, the one or more processors may adjust an orientation of the 3DMM to align with the orientation of new right foot cluster 5801. For example, the processors may align axes of the morphable model with similar axes of right foot cluster 5801, such as those described above with reference to FIG. 51. At step 6303, the one or more processors may translate the 3DMM in order to place it over cluster 5801. At step 6304, the one or more processors may scale the 3DMM to achieve a close fit with cluster 5801. In some aspects, the scaling may be achieved without deforming the 3DMM.

As shown in FIG. 63, procedures 4803 may include a series of iterations, during which the foot parameters may be modified to achieve a best fit between the 3DMM and one or more exemplar feet. At step 6305, for example, the one or more processors may select a first foot parameter, such as any one of the six foot parameters depicted in FIG. 61. At step 6306, the one or more processors may calculate an error value between cluster 5801 and the 3DMM. In some aspects, the error value may represent a difference between the first foot parameter in the cluster 5801 and the first foot parameter in the 3DMM.

At step 6307, the one or more processors may reduce the error value by adjusting the foot parameters based on the first foot parameter. The 3DMM may be constructed by the processors to constrain the way in which deformations may take place. For example, adjusting the first parameter at step 6307 may cause adjustments to other parameters in order to accommodate the constraints of the 3DMM. Given this approach, the adjustments made at step 6307 may not eradicate the error completely. However, on any particular iteration, these adjustments may reduce the error value significantly (e.g., by fifty percent), followed by further adjustments being made to other parameters of the 3DMM with similar result, until the error value approaches a lower limit. At step 6308, the one or more processors may determine whether a further iteration of the 3DMM is to be made. The determination may be based on the reduced error value from step 6307. If the question asked at step 6308 is answered in the affirmative, then the one or more processors may return to step 6305, select another foot parameter, and repeat steps 6306 to 6307 therewith.

Procedures 4803 may continue until all of the foot parameters have been adjusted at least once. In some aspects, given the interrelationship between the foot parameters, additional iterations may be required to further reduce the error value and/or achieve a better fit. For example, having considered all of the parameters at least once, and reduced the error value thereby, the one or more processors may again answer the question asked at step 6308 in the affirmative, returning to step 6305, resulting in the first parameter being selected again, and the process repeated.

Subsequent iterations may continue accordingly, resulting in a convergence towards a solution, such as an error value that approaches a lower limit. It is appreciated that subsequent iterations may result in smaller and smaller adjustments being made. To reduce processing power requirements, the one or more processors may use a counter with a predetermined maximum limit, such that only a predetermined maximum number of iterations may occur before answering the question asked at step 6308 in the negative, with or without consideration of the error value.

At step 6309, after answering the question at step 6308 in the negative, to the effect that no further interactions are to take place, the one or more processors may output the 3DMM. At step 6310, the one or more processors may perform evaluations on the 3DMM, and output the evaluations as first evaluation data. A step 6311, having now considered new right foot cluster 5801, the one or more processors may determine whether another foot is to be considered. In the ongoing example, the question asked at step 6311 may be answered in the affirmative. Accordingly, the one or more processors may select the new left foot cluster 5802 at step 6301, and repeat the following steps, until outputting second evaluation data at step 6310, and answering the question at step 6311 in the negative.

Accordingly, the input of procedures 4803 may include new right foot cluster 5801 and new left foot cluster 5802; and output of procedures 4803 may include first evaluation data derived from cluster 5801, and second evaluation data derived from cluster 5802.

FIG. 64

Figure 64:
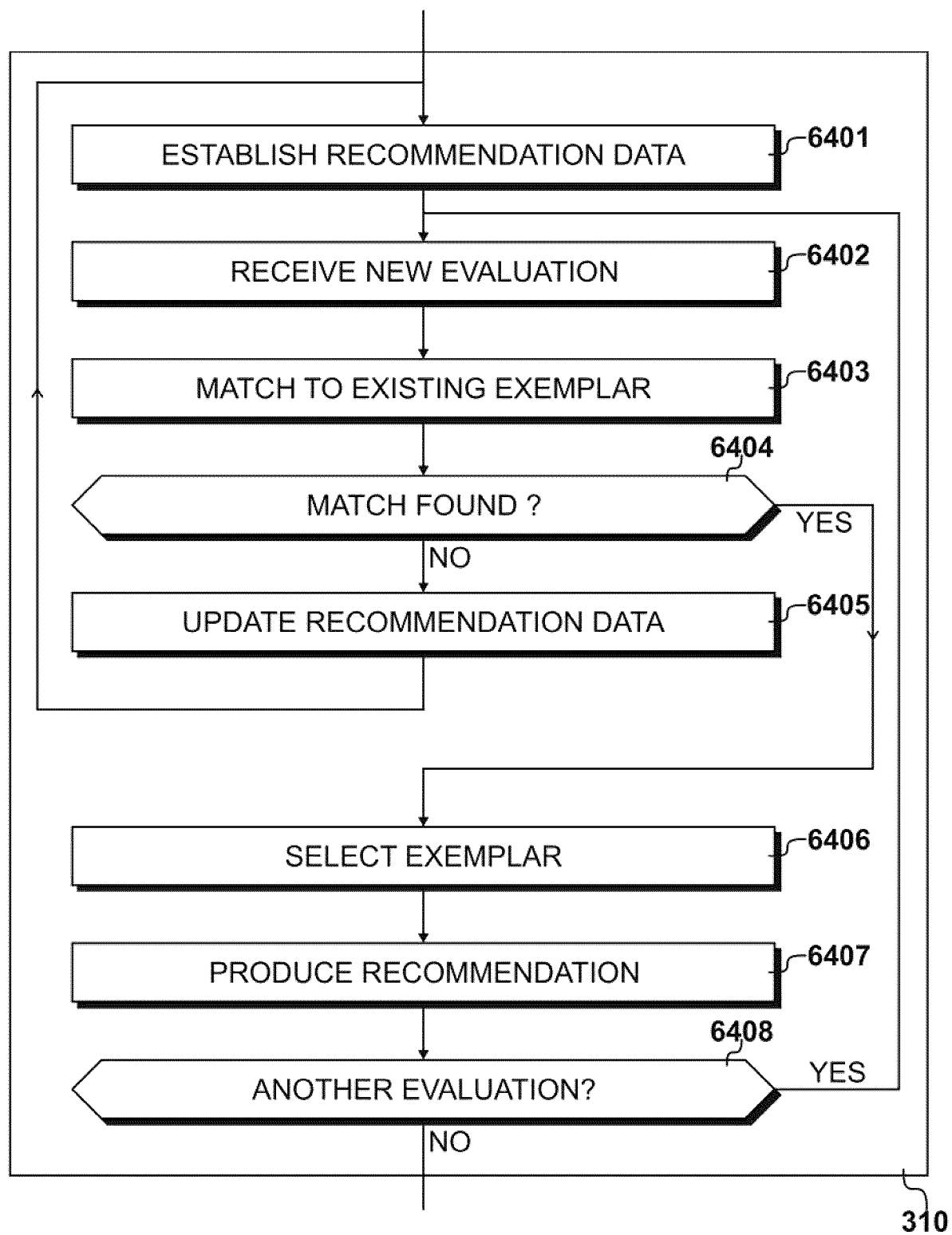
FIG. 64 details an example of the recommendation process identified in FIG. 3.

Additional aspects of an exemplary recommendation process 310 are depicted in FIG. 64. As now described, the one or more processors may use recommendation process 310 to analyse the evaluation data from step 6310 (FIG. 63), and output footwear recommendation data therefrom.

In some aspects, the one or more processors may identify foot-related dimensions and/or specify a plurality of values for an exemplar foot. For example, the one or more processors may measure a plurality of exemplar feet according to these dimensions, and produce multi-dimensional data for each exemplar foot. In this example, the one or more processors may analyse the multi-dimensional data in order to identify clusters of data locations in a multi-dimensional space; and the recommendation output data may be produced by identifying one of these clusters.

Accordingly, the recommendation process 310 may output recommendations as to which footwear to allocate to a particular recipient. Each recommendation may be an objective approach that removes any subjective contributions made by the recipient and/or other person responsible for the allocation process. In some aspects, any bias that may be present on the part of the recipient or such person may have been removed. The objective approach also may provide a recipient with an increased level of reassurance, to the effect that the footwear will be considered to fit and be comfortable. For example, when making allocations at a distance, the extent to which uncomfortable footwear is returned should be reduced and possibly eradicated. Furthermore, the data also may facilitate the generation of manufacturing recommendation data, such that machines 316 for the manufacture of footwear may be enhanced.

One possible approach to footwear selection may be to scan an interior portion of a plurality of footwear items using a three-dimensional scanner, resulting in a data model of the interior portion of each footwear item. However, due to manufacturing tolerances, many measurements of similar footwear items may be required to determine appropriate average measurements. Size and style may need to be accounted for. For example, multiple measurements of the same style of shoe may be required due to manufacturing tolerances; and repeated to accommodate the different sizes for men and women. Consequently, these operations may require significant burdens in the form of data entry, memory, and processing power.

Evaluation process 310 may reduce these burdens. For example, according to some aspects, size as such may not be identified, and process 310 may not generate an indication of size (in the conventional sense) for a particular recipient, except possibly as a fall-back position. Instead, evaluation process 310 may adopt a "proxy" approach, in which each foot of new recipient is matched to one or more exemplar feet. For example, with the proxy approach, each foot of the new recipient may be matched to an exemplar foot of an existing exemplar-recipient who has identified footwear that is considered to be of an appropriate fit.

Accordingly, if an exemplary-recipient has identified footwear that is of the correct fit, then the one or more processors may assume that other recipients, having substantially similar feet in multiple dimensions, will also find this same collection of footwear to be an appropriate fit. In this example, the actual measurements and/or standard notational size of the footwear may become unnecessary, provided that the individual examples of footwear selected by the exemplar-recipients are still available and have been produced by similar machines.

Additional aspects of recommendation process 310 are now described with reference to FIG. 64. For example, at step 6401, the one or more processors may establish recommendation data, and record the recommendation data as exemplar data. In some aspects, the exemplar data may be stored on a storage device 311 (FIG. 3). At step 6402, the one or processors may receive the evaluation data output from step 6310 described above. At step 6403, the one or more processors may make a comparison in an attempt to match the evaluation data to an exemplar from the exemplar data recorded at step 6401. At step 6404, the one or more processors may determine whether a match has been found.

As more and more data is added to the exemplar data, fewer and fewer instances will occur when the question asked at step 6404 may be answered in the negative. Should this situation arise, then the one or more processors may update the recommendation data at step 6405, such that there is a greater likelihood that a match will be found if a similar assessment is received later. With a sufficiently rich data-set of exemplar data, the one or more processors may answer the question asked at step 6404 in the affirmative, indicating that a match has been found by the one or more processors at step 6403.

At step 6406, after finding the match, the one or more processors may select an exemplar. At step 6407, the one or more processors may output recommendation data based on the selections that have been recorded for the exemplar. Thereafter, at step 6408, the one or more processors may determine whether additional evaluation data is to be considered. If answered in the affirmative, then the one or more processors may return to step 6402 to receive the additional data, and repeat the remaining steps 6403 to 6507 therewith. Alternatively, if the question at step 6408 is answered in the negative, then the processors may terminate the process.

FIG. 65

Figure 65:
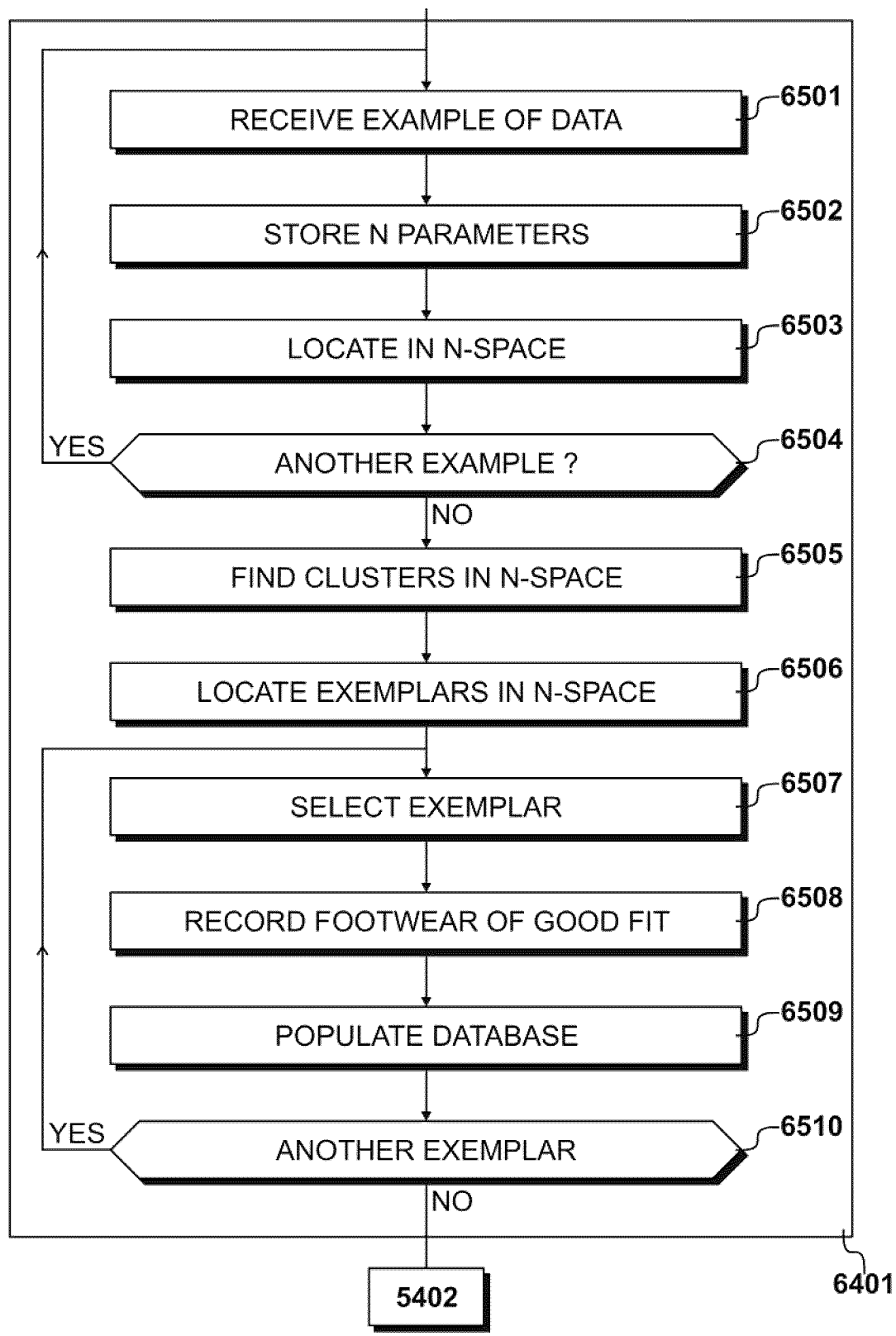
FIG. 65 details an example of the process identified in FIG. 64 for the establishment of recommendation data.

Aspects of an exemplary step 6401 for establishing recommendation data are detailed in FIG. 65.

At step 6501, the one or more processors may receive exemplar data. In some aspects, the exemplar data may be used to establish the existence of exemplars. For example, the exemplar data provide a diverse range of shapes and sizes of feet, as well as other information from an exemplar-recipient. Any information requested by the exemplar-recipient may be included in the exemplar data, including information that may provide the exemplar-recipient with motivation for undergoing many footwear allocations, determine what they consider to be a good fit, and/or determine what they consider to be an unacceptable fit. Thereafter, having established the exemplar database to an operational size, the processors may receive additional evaluation data received from new recipients during subsequent iterations of step 6501, and use the additional data to update the database.

At step 6502, the one or more processors may store "N" foot parameters for the exemplar data. In the following example, N may equal six, such that step 6502 involves storing six different foot parameters. At step 6503, these six foot parameters (or N parameters in the general case) may allow the one or more processors to define a point in a six-dimensional space, or N-dimensional space for the general case. At step 6504, the one or more processors may determine whether another exemplar data is to be received; and, when answered in the affirmative, the next example of data set may be received at step 6501.

When the question asked at step 6504 is answered in the negative, it is assumed that a sufficient number of exemplar data sets have been received. Each example point in N-dimensional space could be considered as an exemplar and some procedures could make use of all of this data. However, in an embodiment, an authoritative sample is sought for the grouping. Thus, from a large volume of example points in N-dimensional space, exemplars (also referred to as "fit leaders") are identified. Points in the N-dimensional space for these exemplars are considered close enough to each point in a cluster that the exemplar may be used for all points lying within the cluster.

At step 6505, the one or more processors may identify clusters of data points in the N-dimensional space. At step 6506, the one or more processors may locate exemplars in the N-dimensional space, with one exemplar being selected for each cluster. At step 6507, the one or more processors may select an exemplar; and at step 6508, the processors may record the allocated footwear (e.g., the footwear representing a good fit for the exemplar-recipient) is recorded. At step 6509, the one or more processors may populate the exemplary database. At step 6510, the one or more processors may determine whether another exemplar is to be selected. When answered in the affirmative, the next exemplar may be selected at step 6507, and further updating of the database continues.

Eventually, all of the exemplars will have been selected, such that the exemplar database is now considered to be operational.

FIG. 66

Figure 66:
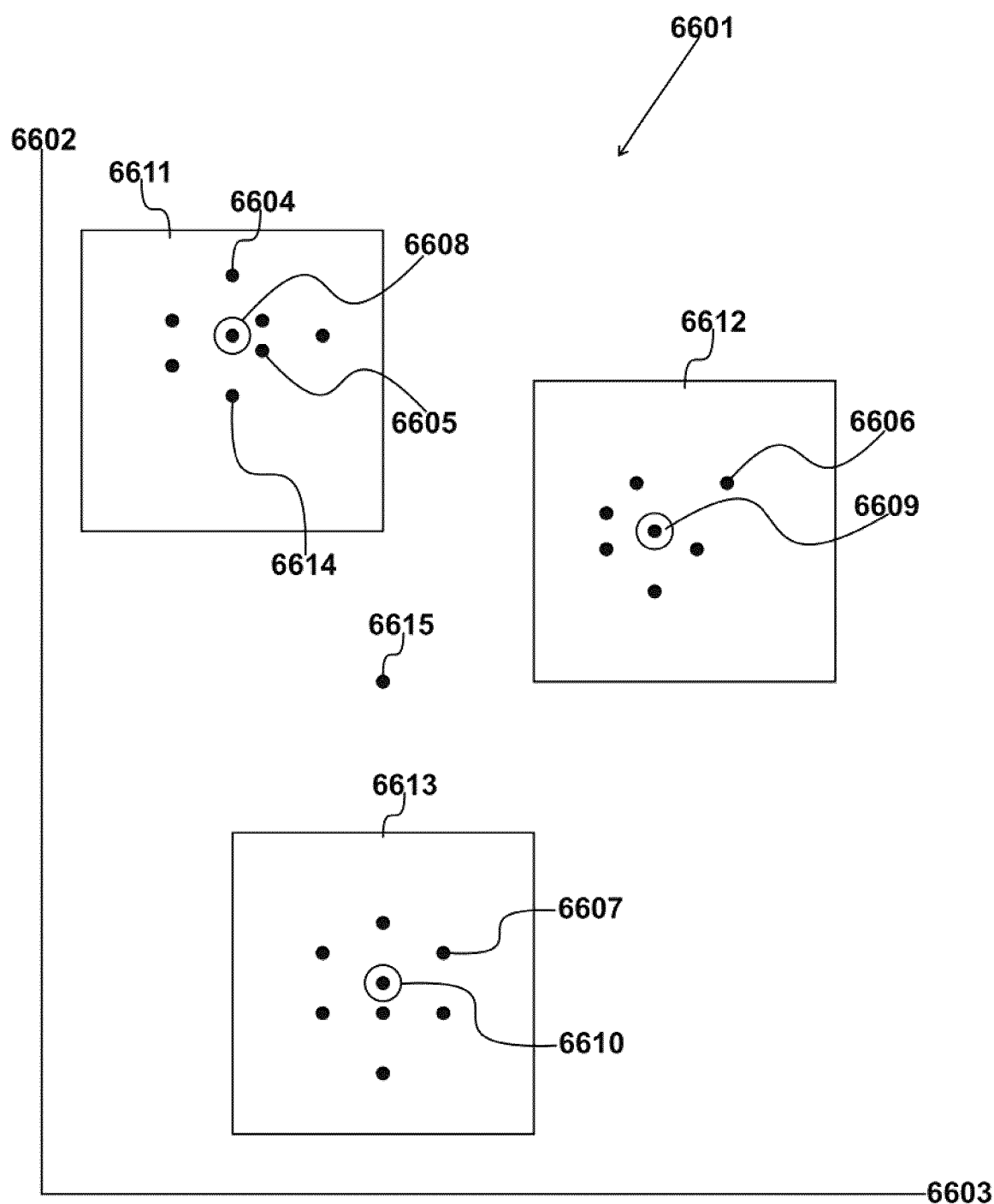
FIG. 66 shows an example of an N-dimensional space for assisting with the allocation of footwear.

An example of an N-dimensional space 6601, established by the procedures shown in FIG. 65, is illustrated in FIG. 66. For the purposes of this illustration, the diagram only shows two of these dimensions, consisting of a first dimension 6602 and a second dimension 6603. In this example, twenty-one examples of data have been received at step 6501. Each data set is plotted as a point in the N-dimensional space, such as point 6604, point 6605, point 6606 and point 6607. As illustrated in FIG. 66, the plotted points may establish clusters, and the one or more processors may identify a substantially central point based on the clusters. In this example, the one or more processors may select exemplars (fit-leaders) from the points that are found substantially centrally within each cluster. As shown in FIG. 66, point 6604 is not the exemplar and neither is point 6605; therefore, the exemplar is selected from circled point 6608. Similarly, point 6609 provides an exemplar and point 6610 provides an exemplar.

In some aspects, the one or more processors may define a bounding region around each exemplar. Each bounding region may be shown as a two-dimensional region, as in the two-dimensional representation of FIG. 66. In multi-dimensional examples, the bounding region may be appropriately dimensioned hyper-cubes or multi-dimensional entities of a different geometry. As shown in FIG. 66, for exemplar 6608, a boundary region 6611 may be defined; for exemplar 6609, a boundary region 6612 may be defined; and for exemplar 6610, a boundary region 6613 may be defined.

When a new assessment is received at step 6402, the one or more processors may use the assessment data to locate a point in the multi-dimensional space identified in FIG. 66. If a point is identified that falls within one of the established regions, then the one or more processors may select an exemplar at step 6406. Thus, if a new assessment results in the establishment of point 6614, exemplar 6608 may be selected, and recommendations may be produced at step 6407, based on the allocations that have been made to that particular exemplar-recipient. Similarly, if the point falls within region 6612, exemplar 6609 may be selected; and if the point falls within region 6613, exemplar 6610 may be selected.

If a new assessment results in a point being positioned at location 6615, then the one or more processors may be unable to make a match, meaning the question asked at step 6404 will be answered in the negative. Under these circumstances, the one or more processors may make a recommendation based on conventional shoe size (the fall-back position). In extreme cases, the one or more processors may recommend that the recipient should seek a bespoke solution.

If many points fall within a particular region for which it is not possible to make an allocation, the one or more processors may make manufacturing recommendations on the basis that a new and significant base of potential recipients has been identified. Thus, a set of recipients may be identified who, previously, were required to seek bespoke solutions and may thereafter receive appropriate footwear allocations.

As a result of the procedures described herein, it may possible for the one or more processors to develop a database of exemplars identifying footwear that they themselves consider to be very agreeable. The footwear may be identified in terms of its make, model, year of manufacture and conventional shoe size. However, in accordance with the principles described herein, the database may not specify a size as such. Instead, the one or more processors may use the allocation data to identify footwear that has been found agreeable by a particular exemplar-recipient, and therefore should also be found agreeable to other recipients. For example, this may be because the new recipient has foot parameters in the N-dimensional space that are relatively close to those of the exemplar.

It is also possible for the regions in N-dimensional space to be provided with layers of confidence surrounding the exemplar. Consequently, if a new point is close to the exemplar, then the one or more processors may make an allocation with a high degree of confidence. Similarly, it is accepted that the confidence level may be lower if the new point is identified at a position towards the edge of a cluster. From a distribution perspective, this suggests that footwear is much less likely to be returned as being unacceptable if the new recipient's point is close to the exemplar.

It is accepted that the exemplar-recipients may be required to try footwear for allocation purposes, on the basis that this is providing a subjective scan. The procedures thereafter may obtain a high dimensional assessment of the item, without actually being required to take physical measurements of the item. When a good fit is experienced, the dimensions are correct for that particular exemplar and the reasons as to why they are a good fit do not need to be investigated further. Thus, when a good fit is identified, the fit should also be correct for all users with similar feet; that is to say, with parameters close to those of the exemplar in the N-dimensional space.

In terms of providing manufacturing recommendations, a clustering pattern of the sort identified in FIG. 66 suggests that manufacturers could adjust their machines 316, such that part of their range falls within a first cluster, a part falls within a second cluster and the remainder falls within a third cluster. The manufacturer would then be in a position to achieve better fitting by producing different ranges, as distinct from producing just a single range that may be less than optimum for everyone.

EXEMPLARY ASPECTS

While principles of the present disclosure are disclosed herein with reference to illustrative aspects of particular applications, the disclosure is not limited thereto. Those having ordinary skill in the art and access to the teachings provided herein will recognize the additional modifications, applications, aspects, and substitution of equivalents may all fall in the scope of the aspects described herein. Accordingly, the present disclosure is not to be considered as limited by the foregoing descriptions.

A number of exemplary aspects are now described. Each aspect is fully supported by the present disclosure, and may provide additional examples in complement to the examples described above.

One exemplary aspect is a method of recording static images of feet, for the purpose of creating a three-dimensional machine-readable model of said feet and deriving evaluations from said machine-readable model. This method may comprise the steps of: receiving video image data from a camera; processing said video image data to distinguish foot-related pixels from non-foot-related pixels of a background; tracking said foot-related pixels during a manual sweep of said camera around a pair of feet; and intermittently capturing static images of said feet during said manual sweep and recording image data of said captured static images to a storage device.

Another exemplary aspect is a method of recording two-dimensional static images of feet, for the purpose of creating a three-dimensional machine-readable model of said feet. This method may comprise the steps of: receiving video image data from a camera; displaying said video image data on a video display during a manual sweep around said feet; recording image data for a plurality of captured two-dimensional static images during said manual sweep; overlaying a graphical representation of a required sweep over said displayed video image data of said feet; and providing indications upon said graphical representation to show where said static images have been recorded and where a recorded image is still required.

Another exemplary aspect is a method of recording two-dimensional static images of feet for remote image processing. This method may comprise the steps of: receiving video image data from a camera; identifying a region containing foot-related pixels; adjusting attributes of said camera for capturing said foot-related pixels; capturing a plurality of still images from different positions around said feet and recording image data; testing the quality of said recorded image data; and selectively rejecting or uploading said image data recorded during said recording step based on said testing step.

Another exemplary aspect is a method of uploading image data of feet to a remote data processing facility. This method may comprise the steps of: capturing a plurality of static images of feet from a camera, while manually sweeping said camera; receiving movement data from a movement detection device; recording position data calculated from said movement data each time an image is captured; storing image data for each captured image with respective position data indicating the position of the camera when the image was captured; and uploading said stored image data with said stored position data.

Another exemplary aspect is a method of processing foot-related image data to facilitate an allocation of footwear. This method may comprise the steps of: receiving two-dimensional image data, representing two-dimensional static images of a feet, each captured by an image capturing device that includes a camera, while said camera was swept around a pair of feet; identifying a plurality of similar features in two or more of said two-dimensional static images to locate camera orientations by triangulation; determining the position of said features in a modelled three-dimensional space; creating a three dimensional cloud of points in said modelled three-dimensional space based on said determined positions; and evaluating said three dimensional cloud of points to produce evaluation output data.

Another exemplary aspect is a method of processing three-dimensional data points derived from two-dimensional image data representing a plurality of two-dimensional images of feet standing on a floor to separate a first cluster of points derived from said feet from a second cluster of points derived from said floor. This method may comprise the steps of: locating a two-dimensional ground-plane in said three-dimensional space; estimating an initial clearance zone between said ground-plane and said first cluster of points; separating said first cluster of points from said ground-plane based on said initial clearance zone; analysing the orientation of said first cluster of points to locate a scaling-object in said three-dimensional space; scaling said three-dimensional space with reference to said located scaling-object; and repeating said separating step based on a scaled clearance zone.

Another exemplary aspect is a method of processing image data of feet to facilitate footwear allocation. This method may comprise the steps of: receiving a plurality of two-dimensional static images of feet standing on a floor with a visible scaling-object of known size at a substantially predetermined position relative to said feet; generating a three-dimensional representation of said feet, said floor and said scaling-object; identifying a search region for said scaling-object in said three-dimensional representation; locating said search region in one of said two-dimensional static images; rectifying said two-dimensional search region to restore an original shape; segmenting said scaling-object from a background in said rectified image; and transforming parameters of said segmented scaling-object back to said three-dimensional space.

Another exemplary aspect is a method of evaluating foot-related image data to facilitate an allocation of footwear. This method may comprise the steps of: receiving foot-related image data showing a plurality of static two-dimensional images; deriving a cloud of points in a modelled three-dimensional space representing positions on the surface of feet shown in said images; segmenting said cloud of points into a right-foot-cluster, a left-foot-cluster and a ground-plane cluster; manipulating a first three-dimensional mesh to substantially adopt the size and shape of said right-foot-cluster; and manipulating a second three-dimensional mesh to substantially adopt the size and shape of said left-foot-cluster.

Another exemplary aspect is a method of processing image data of feet to facilitate footwear allocation. This method may comprise the steps of: defining a three-dimensional model of feet, such that said model is only deformable in ways consistent with actual foot variations within a population by identifying model manipulation parameters from data representing examples of feet in said population; and manipulating said parameters in response to model manipulation data generated from two-dimensional image data representing two-dimensional images of a recipient's foot.

Another exemplary method is a method of analysing image data of feet to produce recommendation data for footwear allocation. This method may comprise the steps of: identifying parameters that specify foot variations within a population of footwear-wearing individuals; measuring a plurality of feet with respect to said parameters to produce a multi-dimensional data-set for each foot; analysing said multi-dimensional data-set to identify clusters of data locations in a multi-dimensional space, with a dimension of said multi-dimensional space allocated to each said identified parameter; receiving new input data from a foot of a recipient to whom footwear is to be allocated; matching said new input data to one of said identified clusters; and producing recommendation data based on said matching step.

The invention claimed is:

1. A computer-implemented method comprising:
receiving, from a camera, a video feed depicting a pair of feet and a scaling object;
capturing, with the camera, images of the feet and the scaling object based on the video feed;
identifying foot features in each captured image;
determining camera positions for each captured image by triangulating the foot features;
generating a point cloud in a three-dimensional space by positioning each foot feature in the three-dimensional space based on the camera positions;
scaling the point cloud based on the scaling object;
segmenting the point cloud into at least a right-foot cluster and a left-foot cluster;
fitting a first three-dimensional morphable model to the right-foot cluster according to first foot parameters by a first process comprising:
(i) placing the first three-dimensional morphable model over the right-foot cluster;
(ii) modifying the first three-dimensional morphable model without deformation to fit the right-foot cluster; and
(iii) modifying the first three-dimensional morphable model with deformation by iteratively adjusting the first foot parameters individually or in combination to reduce an error value between the first three-dimensional morphable model and the right-foot cluster;
fitting a second three-dimensional morphable model to the left-foot cluster according to second foot parameters by a second process comprising:
(i) placing the second three-dimensional morphable model over the left-foot cluster;
(ii) modifying the second three-dimensional morphable model without deformation to fit the left-foot cluster; and
(iii) modifying the second three-dimensional morphable model with deformation by iteratively adjusting the second foot parameters individually or in combination to reduce an error value between the second three-dimensional morphable model and the left-foot cluster; and outputting data comprising right-foot data and left-foot data.

2. The method of claim 1, further comprising processing the video feed to distinguish foot pixels from non-foot pixels.

3. The method of claim 2, wherein processing the video feed comprises:

generating a tracker model based on one of the captured images; and tracking the foot pixels in the video feed based on the tracker model.

4. The method of claim 3, wherein capturing the images comprises adjusting a setting of the camera based on the foot pixels.

5. The method of claim 1, further comprising:

matching the first three-dimensional morphable model with a first exemplar foot based on the first foot parameters, and matching the second three-dimensional morphable model with a second exemplar foot based on the second foot parameters.

6. The method of claim 5, further comprising selecting footwear based on at least one of the first exemplar foot and the second exemplar foot without reference to a standard notational size of the footwear.

7. The method of claim 1, wherein receiving the video feed further comprises moving the camera in a sweeping movement around the pair of feet, and capturing images during the sweeping movement.

8. The method of claim 7, wherein moving the camera in the sweeping movement comprises:

holding the camera with an outstretched arm;

orienting the camera towards the pair of feet and the scaling object; and rotating the camera around the pair of feet and the scaling object with the outstretched arm to maintain a distance between the camera and the pair of feet and the scaling object during the rotation.

9. The method of claim 8, wherein the sweeping movement comprises a plurality of rotational positions, and the method comprises determining whether an image has been captured for each rotational position.

10. The method of claim 9, further comprising receiving position data from a sensor, wherein determining whether the image has been captured for each rotational position is based on the position data.

11. The method of claim 1, further comprising receiving the first three-dimensional morphable model and the second three-dimensional morphable model from a remote data source.

12. The method of claim 1, further comprising segmenting the point cloud into a ground cluster and removing the ground cluster from the point cloud.

13. The method of claim 12, wherein scaling the point cloud comprises:

determining a scale from each captured image based on the scaling-object; and determining a point cloud scale by averaging the scale of each captured image.

14. The method of claim 10, further comprising segmenting the point cloud into a ground cluster and removing the ground cluster from the point cloud based on the point cloud scale.

15. A computer-implemented system comprising:

means for receiving, from a camera, a video feed depicting a pair of feet and a scaling object;

means for capturing, with the camera, images of the feet and the scaling object based on the video feed;

means for identifying foot features in each captured image;

means for determining camera positions for each captured image by triangulating the foot features;

means for generating a point cloud in a three-dimensional space by positioning the foot features in the three-dimensional space based on the camera positions;

means for scaling the point cloud based on the scaling object;

means for segmenting the point cloud into at least a right-foot cluster and a left-foot cluster;

means for fitting a first three-dimensional morphable model to the right-foot cluster according to first foot parameters by a first process comprising:

(i) placing the first three-dimensional morphable model over the right-foot cluster;

(ii) modifying the first three-dimensional morphable model without deformation to fit the right-foot cluster; and (iii) modifying the first three-dimensional morphable model with deformation by iteratively adjusting the first foot parameters individually or in combination to reduce an error value between the first three-dimensional morphable model and the right-foot cluster;

means for fitting a second three-dimensional morphable model to the left-foot cluster according to second foot parameters by a second process comprising:

(i) placing the second three-dimensional morphable model over the left-foot cluster;

(ii) modifying the second three-dimensional morphable model without deformation to fit the left-foot cluster; and (iii) modifying the second three-dimensional morphable model with deformation by iteratively adjusting the second foot parameters individually or in combination to reduce an error value between the second three-dimensional morphable model and the left-foot cluster; and means for outputting data comprising right-foot data and left-foot data.

* * * * *